(12) United States Patent
Jensen

(10) Patent No.: US 7,514,537 B2
(45) Date of Patent: Apr. 7, 2009

(54) CHIMERIC IMMUNORECEPTOR USEFUL IN TREATING HUMAN GLIOMAS

(75) Inventor: Michael Jensen, Sierra Madre, CA (US)

(73) Assignee: City of Hope, Duarte, CA (US)

( * ) Notice: Subject to any disclaimer, the term of this patent is extended or adjusted under 35 U.S.C. 154(b) by 37 days.

(21) Appl. No.: 11/274,344

(22) Filed: Nov. 16, 2005

(65) Prior Publication Data

US 2006/0067920 A1    Mar. 30, 2006

Related U.S. Application Data

(63) Continuation-in-part of application No. 10/134,645, filed on Apr. 30, 2002, now abandoned.

(60) Provisional application No. 60/286,981, filed on Apr. 30, 2001.

(51) Int. Cl.
  C07K 16/46    (2006.01)
  C12N 5/22     (2006.01)
  C12N 15/63    (2006.01)

(52) U.S. Cl. .............. 530/387.3; 424/93.21; 435/320.1; 435/372.3; 530/350

(58) Field of Classification Search .................. None
See application file for complete search history.

(56) References Cited

U.S. PATENT DOCUMENTS 5,359,046 A    10/1994  Capon et al.
6,410,319 B1    6/2002  Raubitschek et al.

FOREIGN PATENT DOCUMENTS

WO    WO 00/23573 A2    4/2000
WO    WO0023573         4/2000

OTHER PUBLICATIONS

Bonnerot et al, 1997. Immunology Letters. 47: 1-4.*
Ehtesham et al, 2004. Cancer Control. 11(3): 192-207.*
Campbell et al. (1997) Theriology 47(1): 63-72.*

(Continued)

Primary Examiner—Elizabeth C. Kemmerer
Assistant Examiner—Zachary C Howard
(74) Attorney, Agent, or Firm—Rothwell, Figg, Ernst & Manbeck

(57) ABSTRACT

The present invention relates to chimeric transmembrane immunoreceptors, named "zetakines," comprised of an extracellular domain comprising a soluble receptor ligand linked to a support region capable of tethering the extracellular domain to a cell surface, a transmembrane region and an intracellular signaling domain. Zetakines, when expressed on the surface of T lymphocytes, direct T cell activity to those specific cells expressing a receptor for which the soluble receptor ligand is specific. Zetakine chimeric immunoreceptors represent a novel extension of antibody-based immunoreceptors for redirecting the antigen specificity of T cells, with application to treatment of a variety of cancers, particularly via the autocrin/paracrine cytokine systems utilized by human maligancy. In a preferred embodiment is a glioma-specific immunoreceptor comprising the extracellular targeting domain of the IL-13Rα2-specific IL-13 mutant IL-13 (E13Y) linked to the Fc region of IgG, the transmembrane domain of human CD4, and the human CD3 zeta chain.

4 Claims, 24 Drawing Sheets

OTHER PUBLICATIONS

Lazovic et al, 2008. Clin Cancer Res. 14(2): 3832-3839.*

Altenschmidt, U. et al., "Cytolysis of Tumor Cells Expressing In the NEU/ERBB-2, ERBB-3, and ERBB-4 Receptors by Genetically Targeted Naive T Lymphocytes," Clinical Cancer Research, The American Association for Cancer Research, vol. 2, No. 6, Jun. 1996, pp. 1001-1008, US.

Ashkenazi et al., 1995, "Immunoadhesins: An Alternative to Human Monoclonal Antibodies," Methods: A Companion to Methods in Enzymology, 8:104-115 (1995).

Debinski W., Gibo DM, Puri RK, "Novel way to increase targeting specificity to a human glioblastoma-associated receptor for interleukin 13." Int J Cancer. 1998;76:547-551.

Kahlon, K. et al., "The IL-13 zetakine chimeric immunoreceptor: a novel approach to genetically engineer T cells for glioma immunotherapy," Neuro-Oncology, vol. 3, No. 4, Oct. 2001, pp. 315-316, Washington, D.C.

Kahlon, K. et al., "Redirecting T lymphocyte antigen specificity via engineered zetakine immonoreceptors: development of a prototype construct specific for the tumor-restricted IL-13alpha2 receptor," Molecular Therapy, vol. 3, No. 5, May 2001, p. S374, AB.

Kahlon et al., "Specific Recognition and Killing of Glioblastoma Multiforme by Interleukin 13-Zetakine Redirected Cytolytic T Cells," 2004, Cancer Res. 64(24):9160-9166.

Niederman, T.M.J. et al., "Antitumor activity of cytotoxic T lymphocute engineered to target vascular endothelial growth factor receptors," Proceedings of the National Academy of Sciences of USA, National Academy of Science, vol. 99, No. 10, May 14, 2002, pp. 7009-7014.

Obiri N.I. et al., "The IL-13 receptor structure differs on various cell types and may share more than one component with IL-4 receptor," J. Immun., (158):756-764, 1997.

Yamasaki T., Handa H., Yamashita J., Watanabe Y., Namba Y., Hanaoka M., "Specific adoptive immunotherapy of malignant glioma with long-term cytotoxic T lymphocyte line expanded in T-cell growth factor." Experimental study and future prospects, Neurosurg Rev. 1984;7:37-54.

Ashkenazi, A. et al., "Immunoadhesions: An alternative to Human Monoclonal Antibodies," *Methods: A Companion to Methods in Enzymology*, vol. 8, No. 2, Oct. 1995, pp. 104-115.

Debinski, W. et al., Human glioma cells overexpress receptors for interleukin 13 and are extremely sensitive to a novel chimeric protein composed of interleukin 13 and pseudomonas exotoxin, *Clinical Cancer Research* (1):1253-1258, 1995.

Debinski, W. et al., Novel way to increase targeting specificity to a human glioblastoma-associated receptor for interleukin 13, *Int. J. Cancer* (76):547-551, 1998.

Debinski, W. et al., Novel anti-brain tumor cytotoxins specific for cancer cells, *Nature Biotechnology* (16):449-453, 1998.

Debinski, W. et al., Receptor for interleukin 13 is a marker and therapeutic target for human high-grade gliomas, *Clinical Cancer Research* (5):985-990, 1999.

Debinski, W. et al., Retargeting 13 for radioimmunodetection and radioimmunotherapy of human high-grade gliomas, *Clin Cancer Res.* (5):3143s-3147s, 1999.

Debinski, W. et al., Receptor for interleukin 13 is abundantly and specifically over-expressed in patients with glioblastoma multiforme, *Int. J. Oncology* (15):481-486, 1999.

Debinski, W., Expression of a restrictive receptor for interleukin 13 is associated with glial transformation, *J. Neuro-Oncology* (48):103-111, 2000.

Jensen, M. et al., CD20 is a molecular target for scFvFc:zeta receptor redirected T cells: implications for cellular Immunotherapy of CD20+malignancy, *Biol. Blood Marrow Transplant* (4):75-83, 1998.

Joshi, B.H. et al., Interleukin-13 receptor α Chain: A novel tumor-associated transmembrane protein in primary explants of human malignant gliomas, *Cancer Research* (60):1168-1172, 2000.

Kahlon, K., et al., "Redirecting T lymphocyte antigen specificity via engineered zetakin immunoreceptors: development of a prototype construct specific for the tumor-restricted IL-13alpha2 receptor," *Molecular Therapy*, vol. 3, No. 5, May 2001, p. S374, AB.

Kahlon, K et al., "Specific recognition and killing of glioblastoma multiforme by interleukin 13-zetakine redirected cytolytic T cell," *Cancer Res.*, vol. 64, No. 24, Dec. 15, 2004, pp. 9160-9166.

Liu, H. et al., Interleukin-13 sensitivity and receptor phenotypes of human glial cell lines: Non-neoplastic glia and low-grade astrocytoma differ from malignant glioma, *Cancer Immunol. Immunother.* (49):319-324, 2000.

Minty, A. et al., Interleukin-13 is a new human lymphokine regulating inflammatory and immune responses, *Nature* (362):248-250, 1993.

Mintz, A. et al., Cancer genetics/epigenetics and the X chromosome: Possible new links for malignant glioma pathogenesis and immune-based therapies, *Crit. Rev. Oncog* (11)1:77-95, 2000.

Moeller, M. et al., "A functional role for CD28 costimulation in tumor recognition by single-chain receptor modified T cells," *Cancer Gene Therapy*, vol. 11, No. 5, May 2004, pp. 371-379.

Murata, T. et al., Structure of IL-13 receptor: analysis of subunit composition in cancer and immune cells, *Biochemical and Biophysical Research Communications* (238):90-94, 1997.

Niederman, T.M.J. et al., "Antitumor activity of cytotoxic T lymphocyte engineered to target vascular endothelial growth factor receptors," *Proceedings of the National Academy of Sciences of USA, National Academy of Science*, vol. 99, No. 19, May 14, 2002, pp. 7009-7014.

Obiri N.I. et al., The IL-13 receptor structure differs on various cell types and may share more than one component with IL-4 receptor, *J. Immun.*, (158):756-764, 1997.

Thompson J.P. et al., Mutants of interleukin 13 with altered reactivity toward interleukin 13 receptors, *J. Biol Chem.* (274)42:29944-29950, 1999.

Xu, X. et al., Targeting and therapy of carcinoembryonic antigen-expressing tumors in transgenic mice with an antibody-interleukin 2 fusion protein, *Cancer Research* (60):4475-4484, 2000.

* cited by examiner

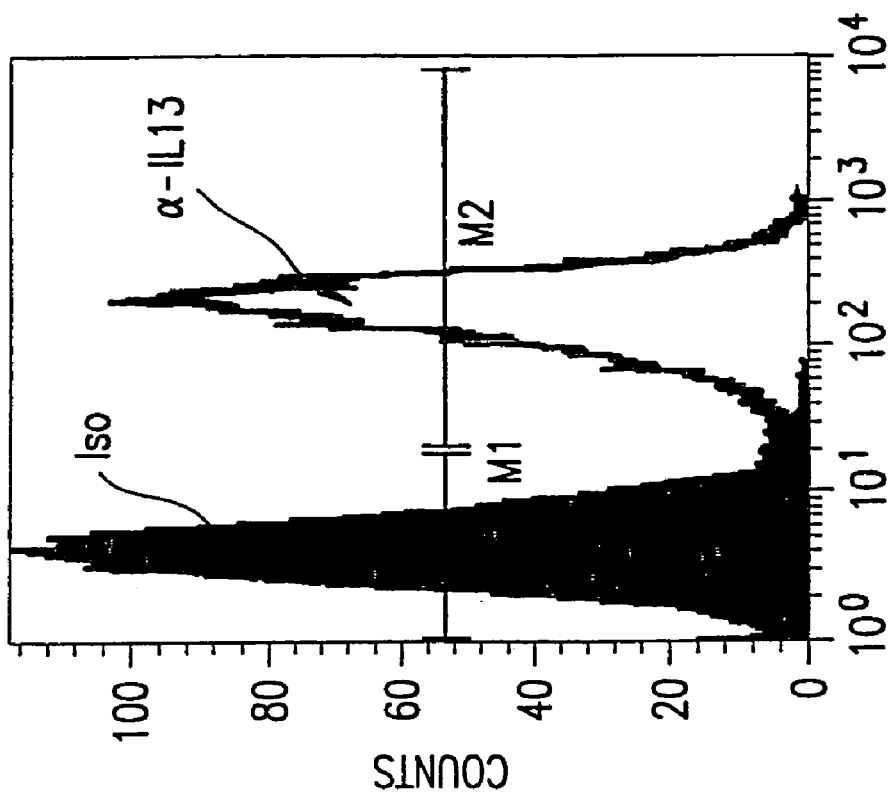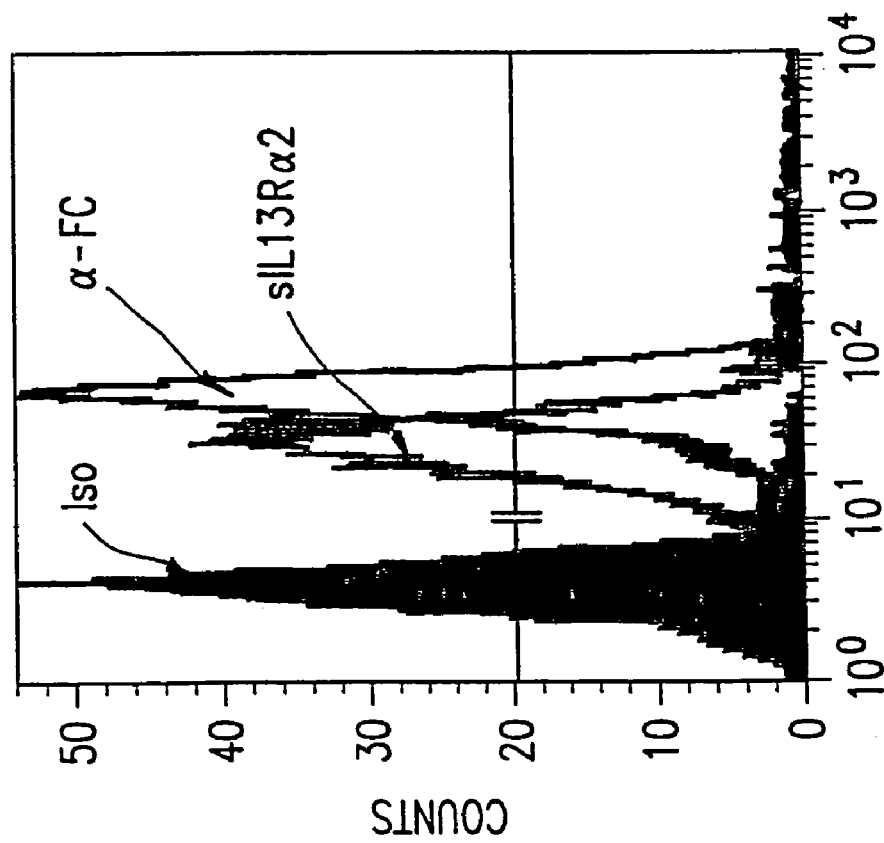
FIG. 2

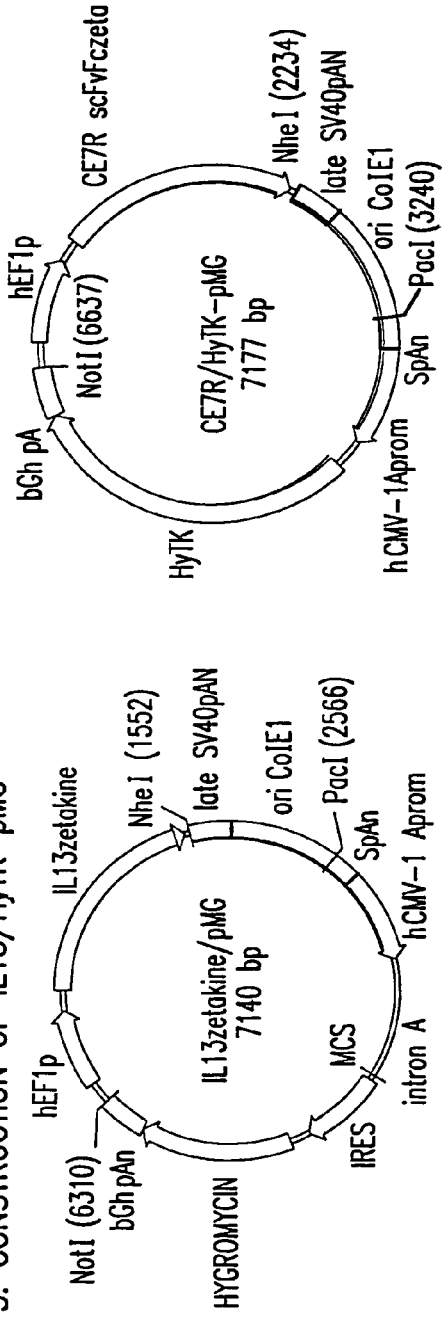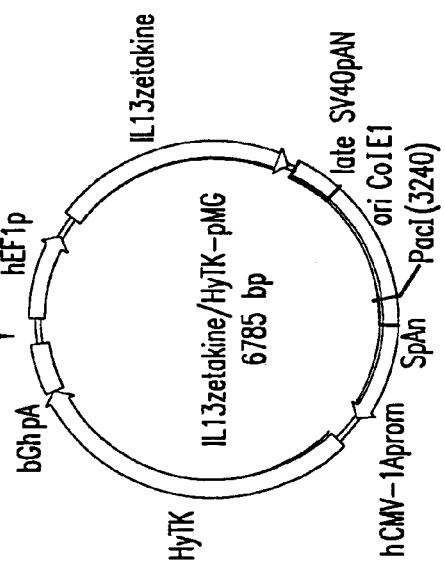
FIG. 8C

Figure 10

Plasmid DNA Vector Sequence

```
          (hEF1p →)
  1  TCGAAGGATC TGCGATCGCT CCGGTGCCCG TCAGTGGGCA GAGCGCACAT CGCCCACAGT  [SEQ ID NO: 14]
     AGCTTCCTAG ACGCTAGCGA GGCCACGGGC AGTCACCCGT CTCGCGTGTA GCGGGTGTCA  [SEQ ID NO: 16]

61  CCCCGAGAAG TTGGGGGGAG GGGTCGGCAA TTGAACCGGT GCCTAGAGAA GGTGGCGCGG
     GGGGCTCTTC AACCCCCCTC CCCAGCCGTT AACTTGGCCA CGGATCTCTT CCACCGCGCC

121  GGTAAACTGG GAAAGTGATG TCGTGTACTG GCTCCGCCTT TTTCCCGAGG GTGGGGGAGA
     CCATTTGACC CTTTCACTAC AGCACATGAC CGAGGCGGAA AAAGGGCTCC CACCCCCTCT

181  ACCGTATATA AGTGCAGTAG TCGCCGTGAA CGTTCTTTTT CGCAACGGGT TTGCCGCCAG
     TGGCATATAT TCACGTCATC AGCGGCACTT GCAAGAAAAA GCGTTGCCCA AACGGCGGTC

241  AACACAGCTG AAGCTTCGAG GGCTCGCAT CTCTCCTTCA CGCGCCCGCC GCCCTACCTG
     TTGTGTCGAC TTCGAAGCTC CCCGAGCGTA GAGAGGAAGT GCGCGGGCGG CGGGATGGAC

301  AGGCCGCCAT CCACGCCGGT TGAGTCGCGT TCTGCCGCCT CCCGCCTGTG GTGCCTCCTG
     TCCGGCGGTA GGTGCGGCCA ACTCAGCGCA AGACGGCGGA GGGCGGACAC CACGGAGGAC

361  AACTGCGTCC GCCGTCTAGG TAAGTTTAAA GCTCAGGTCG AGACCGGGCC TTTGTCCGGC
     TTGACGCAGG CGGCAGATCC ATTCAAATTT CGAGTCCAGC TCTGGCCCGG AAACAGGCCG

421  GCTCCCTTGG AGCCTACCTA GACTCAGCCG GCTCTCCACG CTTTGCCTGA CCCTGCTTGC
     CGAGGGAACC TCGGATGGAT CTGAGTCGGC CGAGAGGTGC GAAACGGACT GGGACGAACG

481  TCAACTCTAC GTCTTTGTTT CGTTTTCTGT TCTGCGCCGT TACAGATCCA AGCTGTGACC
     AGTTGAGATG CAGAAACAAA GCAAAAGACA AGACGCGGCA ATGTCTAGGT TCGACACTGG

541  GGCGCCTACG TAAGTGATAT CTACTAGATT TATCAAAAAG AGTGTTGACT TGTGAGCGCT
     CCGCGGATGC ATTCACTATA GATGATCTAA ATAGTTTTTC TCACAACTGA ACACTCGCGA

601  CACAATTGAT ACGGATTCAT CGAGAGGGAC ACGTCGACTA CTAACCTTCT TCTCTTTCCT
     GTGTTAACTA TGCCTAAGTA GCTCTCCCTG TGCAGCTGAT GATTGGAAGA AGAGAAAGGA (IL13 zetakine →)  [SEQ ID NO: 17]
                                         M  L  L    V  T  S    L  L  L
661  ACAGCTGAGA TCACCCTAGA GCCGCCACCA TGCTTCTCCT GGTGACAAGC CTTCTGCTCT
     TGTCGACTCT AGTGGGATCT CGGCGGTGGT ACGAAGAGGA CCACTGTTCG GAAGACGAGA C  E  L  P    H  P  A    F  L  L    I  P  G  P    V  P  P    S  T  A
721  GTGAGTTACC ACACCCAGCA TTCCTCCTGA TCCAGGCCC TGTGCCTCCC TCTACAGCCC
     CACTCAATGG TGTGGGTCGT AAGGAGGACT AGGGTCCGGG ACACGGAGGG AGATGTCGGG
```

Figure 10 (cont'd)

```
         L   R   Y   L      I   E   E      L   V   N      I   T   Q       N   Q   K   A      P   L   C
781    TCAGGTACCT CATTGAGGAG CTGGTCAACA TCACCCAGAA CCAGAAGGCT CCGCTCTGCA
       AGTCCATGGA GTAACTCCTC GACCAGTTGT AGTGGGTCTT GGTCTTCCGA GGCGAGACGT

N   G   S   M      V   W   S      I   N   L      T   A   G   M      Y   C   A      L   E
841    ATGGCAGCAT GGTATGGAGC ATCAACCTGA CAGCTGGCAT GTACTGTGCA GCCCTGGAAT
       TACCGTCGTA CCATACCTCG TAGTTGGACT GTCGACCGTA CATGACACGT CGGGACCTTA

S   L   I   N      V   S   G      C   S   A      I   E   K   T      Q   R   M      L   S   G
901    CCCTGATCAA CGTGTCAGGC TGCAGTGCCA TCGAGAAGAC CCAGAGGATG CTGAGCGGAT
       GGGACTAGTT GCACAGTCCG ACGTCACGGT AGCTCTTCTG GGTCTCCTAC GACTCGCCTA

F   C   P   H      K   V   S      A   G   Q      F   S   S   L      H   V   R      D   T   K
961    TCTGCCCGCA CAAGGTCTCA GCTGGGCAGT TTTCCAGCTT GCATGTCCGA GACACCAAAA
       AGACGGGCGT GTTCCAGAGT CGACCCGTCA AAAGGTCGAA CGTACAGGCT CTGTGGTTTT

I   E   V   A      Q   F   V      K   D   L      L   L   H   L      K   K   L      F   R   E
1021   TCGAGGTGGC CCAGTTTGTA AAGGACCTGC TCTTACATTT AAAGAAACTT TTTCGCGAGG
       AGCTCCACCG GGTCAAACAT TTCCTGGACG AGAATGTAAA TTTCTTTGAA AAAGCGCTCC

G   R   F   N      E   S   K      Y   G   P      P   C   P   P      C   P   A      P   E   F
1081   GACGGTTCAA CGAGTCCAAA TATGGTCCCC CATGCCCACC ATGCCCAGCA CCTGAGTTCC
       CTGCCAAGTT GCTCAGGTTT ATACCAGGGG GTACGGGTGG TACGGGTCGT GGACTCAAGG

L   G   G   P      S   V   F      L   F   P      P   K   P   K      D   T   L      M   I   S
1141   TGGGGGGACC ATCAGTCTTC CTGTTCCCCC CAAAACCCAA GGACACTCTC ATGATCTCCC
       ACCCCCCTGG TAGTCAGAAG GACAAGGGGG GTTTTGGGTT CCTGTGAGAG TACTAGAGGG

R   T   P   E      V   T   C      V   V   V      D   V   S   Q      E   D   P      E   V   Q
1201   GGACCCCTGA GGTCACGTGC GTGGTGGTGG ACGTGAGCCA GGAAGACCCC GAGGTCCAGT
       CCTGGGGACT CCAGTGCACG CACCACCACC TGCACTCGGT CCTTCTGGGG CTCCAGGTCA

F   N   W   Y      V   D   G      V   E   V      H   N   A   K      T   K   P      R   E   E
1261   TCAACTGGTA CGTGGATGGC GTGGAGGTGC ATAATGCCAA GACAAAGCCG CGGGAGGAGC
       AGTTGACCAT GCACCTACCG CACCTCCACG TATTACGGTT CTGTTTCGGC GCCCTCCTCG

Q   F   N   S      T   Y   R      V   V   S      V   L   T   V      L   H   Q      D   W   L
1321   AGTTCAACAG CACGTACCGT GTGGTCAGCG TCCTCACCGT CCTGCACCAG GACTGGCTGA
       TCAAGTTGTC GTGCATGGCA CACCAGTCGC AGGAGTGGCA GGACGTGGTC CTGACCGACT

N   G   K   E      Y   K   C      K   V   S      N   K   G   L      P   S   S      I   E   K
1381   ACGGCAAGGA GTACAAGTGC AAGGTCTCCA ACAAAGGCCT CCCGTCCTCC ATCGAGAAAA
       TGCCGTTCCT CATGTTCACG TTCCAGAGGT TGTTTCCGGA GGGCAGGAGG TAGCTCTTTT
```

Figure 10 (cont'd)

```
          T   I   S   K       A   K   G       Q   P   R       E   P   Q   V       Y   T   L       P   P   S
1441 CCATCTCCAA AGCCAAAGGG CAGCCCCGAG AGCCACAGGT GTACACCCTG CCCCCATCCC
     GGTAGAGGTT TCGGTTTCCC GTCGGGGCTC TCGGTGTCCA CATGTGGGAC GGGGGTAGGG

Q   E   E   M       T   K   N       Q   V   S       L   T   C   L       V   K   G       F   Y   P
1501 AGGAGGAGAT GACCAAGAAC CAGGTCAGCC TGACCTGCCT GGTCAAAGGC TTCTACCCCA
     TCCTCCTCTA CTGGTTCTTG GTCCAGTCGG ACTGGACGGA CCAGTTTCCG AAGATGGGGT

S   D   I   A       V   E   W       E   S   N       G   Q   P   E       N   N   Y       K   T   T
1561 GCGACATCGC CGTGGAGTGG GAGAGCAATG GGCAGCCGGA GAACAACTAC AAGACCACGC
     CGCTGTAGCG GCACCTCACC CTCTCGTTAC CCGTCGGCCT CTTGTTGATG TTCTGGTGCG

P   P   V   L       D   S   D       G   S   F       F   L   Y   S       R   L   T       V   D   K
1621 CTCCCGTGCT GGACTCCGAC GGCTCCTTCT TCCTCTACAG CAGGCTAACC GTGGACAAGA
     GAGGGCACGA CCTGAGGCTG CCGAGGAAGA AGGAGATGTC GTCCGATTGG CACCTGTTCT

S   R   W   Q       E   G   N       V   F   S       C   S   V   M       H   E   A       L   H   N
1681 GCAGGTGGCA GGAGGGGAAT GTCTTCTCAT GCTCCGTGAT GCATGAGGCT CTGCACAACC
     CGTCCACCGT CCTCCCCTTA CAGAAGAGTA CGAGGCACTA CGTACTCCGA GACGTGTTGG

H   Y   T   Q       K   S   L       S   L   S       L   G   K   M       A   L   I       V   L   G
1741 ACTACACACA GAAGAGCCTC TCCCTGTCCC TAGGTAAAAT GGCCCTGATT GTGCTGGGGG
     TGATGTGTGT CTTCTCGGAG AGGGACAGGG ATCCATTTTA CCGGGACTAA CACGACCCCC

G   V   A   G       L   L   L       F   I   G       L   G   I   F       F   R   V       K   F   S
1801 GCGTCGCCGG CCTCCTGCTT TTCATTGGGC TAGGCATCTT CTTCAGAGTG AAGTTCAGCA
     CGCAGCGGCC GGAGGACGAA AAGTAACCCG ATCCGTAGAA GAAGTCTCAC TTCAAGTCGT

R   S   A   D       A   P   A       Y   Q   Q       G   Q   N   Q       L   Y   N       E   L   N
1861 GGAGCGCAGA CGCCCCCGCG TACCAGCAGG GCCAGAACCA GCTCTATAAC GAGCTCAATC
     CCTCGCGTCT GCGGGGGCGC ATGGTCGTCC CGGTCTTGGT CGAGATATTG CTCGAGTTAG

L   G   R   R       E   E   Y       D   V   L       D   K   R   R       G   R   D       P   E   M
1921 TAGGACGAAG AGAGGAGTAC GATGTTTTGG ACAAGAGACG TGGCCGGGAC CCTGAGATGG
     ATCCTGCTTC TCTCCTCATG CTACAAAACC TGTTCTCTGC ACCGGCCCTG GGACTCTACC

G   G   K   P       R   R   K       N   P   Q       E   G   L   Y       N   E   L       Q   K   D
1981 GGGGAAAGCC GAGAAGGAAG AACCCTCAGG AAGGCCTGTA CAATGAACTG CAGAAAGATA
     CCCCTTTCGG CTCTTCCTTC TTGGGAGTCC TTCCGGACAT GTTACTTGAC GTCTTTCTAT

K   M   A   E       A   Y   S       E   I   G       M   K   G   E       R   R   R       G   K   G
2041 AGATGGCGGA GGCCTACAGT GAGATTGGGA TGAAAGGCGA GCGCCGGAGG GGCAAGGGGC
     TCTACCGCCT CCGGATGTCA CTCTAACCCT ACTTTCCGCT CGCGGCCTCC CCGTTCCCCG
```

Figure 10 (cont'd)

```
            H   D   G   L       Y   Q   G       L   S   T       A   T   K   D       T   Y   D       A   L   H
2101 ACGATGGCCT TTACCAGGGT CTCAGTACAG CCACCAAGGA CACCTACGAC GCCCTTCACA
     TGCTACCGGA AATGGTCCCA GAGTCATGTC GGTGGTTCCT GTGGATGCTG CGGGAAGTGT

M   Q   A   L       P   P   R   *
2161 TGCAGGCCCT GCCCCCTCGC TGAGCGGCCG GCGAAGGAGG CCTAGATCTA TCGATTGTAC
     ACGTCCGGGA CGGGGGAGCG ACTCGCCGGC CGCTTCCTCC GGATCTAGAT AGCTAACATG (late SV40pAN →)
2221 AGCTAGCTCG ACATGATAAG ATACATTGAT GAGTTTGGAC AAACCACAAC TAGAATGCAG
     TCGATCGAGC TGTACTATTC TATGTAACTA CTCAAACCTG TTTGGTGTTG ATCTTACGTC 2281 TGAAAAAAAT GCTTTATTTG TGAAATTTGT GATGCTATTG CTTTATTTGT GAAATTTGTG
     ACTTTTTTTA CGAAATAAAC ACTTTAAACA CTACGATAAC GAAATAAACA CTTTAAACAC 2341 ATGCTATTGC TTTATTTGTA ACCATTATAA GCTGCAATAA ACAAGTTAAC AACAACAATT
     TACGATAACG AAATAAACAT TGGTAATATT CGACGTTATT TGTTCAATTG TTGTTGTTAA 2401 GCATTCATTT TATGTTTCAG GTTCAGGGGG AGGTGTGGGA GGTTTTTTAA AGCAAGTAAA
     CGTAAGTAAA ATACAAAGTC CAAGTCCCCC TCCACACCCT CCAAAAAATT TCGTTCATTT (ori ColE1 →)
2461 ACCTCTACAA ATGTGGTAGA TCCATTTAAA TGTTAGCGAA GAACATGTGA GCAAAAGGCC
     TGGAGATGTT TACACCATCT AGGTAAATTT ACAATCGCTT CTTGTACACT CGTTTTCCGG 2521 AGCAAAAGGC CAGGAACCGT AAAAAGGCCG CGTTGCTGGC GTTTTTCCAT AGGCTCCGCC
     TCGTTTTCCG GTCCTTGGCA TTTTTCCGGC GCAACGACCG CAAAAAGGTA TCCGAGGCGG 2581 CCCCTGACGA GCATCACAAA AATCGACGCT CAAGTCAGAG GTGGCGAAAC CCGACAGGAC
     GGGGACTGCT CGTAGTGTTT TTAGCTGCGA GTTCAGTCTC CACCGCTTTG GGCTGTCCTG 2641 TATAAAGATA CCAGGCGTTT CCCCCTGGAA GCTCCCTCGT GCGCTCTCCT GTTCCGACCC
     ATATTTCTAT GGTCCGCAAA GGGGGACCTT CGAGGGAGCA CGCGAGAGGA CAAGGCTGGG 2701 TGCCGCTTAC CGGATACCTG TCCGCCTTTC TCCCTTCGGG AAGCGTGGCG CTTTCTCAAT
     ACGGCGAATG GCCTATGGAC AGGCGGAAAG AGGGAAGCCC TTCGCACCGC GAAAGAGTTA 2761 GCTCACGCTG TAGGTATCTC AGTTCGGTGT AGGTCGTTCG CTCCAAGCTG GGCTGTGTGC
     CGAGTGCGAC ATCCATAGAG TCAAGCCACA TCCAGCAAGC GAGGTTCGAC CCGACACACG 2821 ACGAACCCCC CGTTCAGCCC GACCGCTGCG CCTTATCCGG TAACTATCGT CTTGAGTCCA
     TGCTTGGGGG GCAAGTCGGG CTGGCGACGC GGAATAGGCC ATTGATAGCA GAACTCAGGT
```

Figure 10 (cont'd)

```
2881 ACCCGGTAAG ACACGACTTA TCGCCACTGG CAGCAGCCAC TGGTAACAGG ATTAGCAGAG
     TGGGCCATTC TGTGCTGAAT AGCGGTGACC GTCGTCGGTG ACCATTGTCC TAATCGTCTC

2941 CGAGGTATGT AGGCGGTGCT ACAGAGTTCT TGAAGTGGTG GCCTAACTAC GGCTACACTA
     GCTCCATACA TCCGCCACGA TGTCTCAAGA ACTTCACCAC CGGATTGATG CCGATGTGAT

3001 GAAGAACAGT ATTTGGTATC TGCGCTCTGC TGAAGCCAGT TACCTTCGGA AAAAGAGTTG
     CTTCTTGTCA TAAACCATAG ACGCGAGACG ACTTCGGTCA ATGGAAGCCT TTTTCTCAAC

3061 GTAGCTCTTG ATCCGGCAAA CAAACCACCG CTGGTAGCGG TGGTTTTTTT GTTTGCAAGC
     CATCGAGAAC TAGGCCGTTT GTTTGGTGGC GACCATCGCC ACCAAAAAAA CAAACGTTCG

3121 AGCAGATTAC GCGCAGAAAA AAAGGATCTC AAGAAGATCC TTTGATCTTT TCTACGGGGT
     TCGTCTAATG CGCGTCTTTT TTTCCTAGAG TTCTTCTAGG AAACTAGAAA AGATGCCCCA

PacI
                                                                  -------
3181 CTGACGCTCA GTGGAACGAA AACTCACGTT AAGGGATTTT GGTCATGGCT AGTTAATTAA
     GACTGCGAGT CACCTTGCTT TTGAGTGCAA TTCCCTAAAA CCAGTACCGA TCAATTAATT (SpAn)
3241 GCTGCAATAA ACAATCATTA TTTTCATTGG ATCTGTGTGT TGGTTTTTTG TGTGGGCTTG
     CGACGTTATT TGTTAGTAAT AAAAGTAACC TAGACACACA ACCAAAAAAC ACACCCGAAC

3301 GGGGAGGGGG AGGCCAGAAT GACTCCAAGA GCTACAGGAA GGCAGGTCAG AGACCCCACT
     CCCCTCCCCC TCCGGTCTTA CTGAGGTTCT CGATGTCCTT CCGTCCAGTC TCTGGGGTGA

3361 GGACAAACAG TGGCTGGACT CTGCACCATA ACACACAATC AACAGGGGAG TGAGCTGGAT
     CCTGTTTGTC ACCGACCTGA GACGTGGTAT TGTGTGTTAG TTGTCCCCTC ACTCGACCTA (h CMV-1Aprom →)
3421 CGAGCTAGAG TCCGTTACAT AACTTACGGT AAATGGCCCG CCTGGCTGAC CGCCCAACGA
     GCTCGATCTC AGGCAATGTA TTGAATGCCA TTTACCGGGC GGACCGACTG GCGGGTTGCT 3481 CCCCCGCCCA TTGACGTCAA TAATGACGTA TGTTCCCATA GTAACGCCAA TAGGGACTTT
     GGGGGCGGGT AACTGCAGTT ATTACTGCAT ACAAGGGTAT CATTGCGGTT ATCCCTGAAA 3541 CCATTGACGT CAATGGGTGG AGTATTTACG GTAAACTGCC CACTTGGCAG TACATCAAGT
     GGTAACTGCA GTTACCCACC TCATAAATGC CATTTGACGG GTGAACCGTC ATGTAGTTCA
```

Figure 10 (cont'd)

```
3601 GTATCATATG CCAAGTACGC CCCCTATTGA CGTCAATGAC GGTAAATGGC CCGCCTGGCA
     CATAGTATAC GGTTCATGCG GGGGATAACT GCAGTTACTG CCATTTACCG GGCGGACCGT

3661 TTATGCCCAG TACATGACCT TATGGGACTT TCCTACTTGG CAGTACATCT ACGTATTAGT
     AATACGGGTC ATGTACTGGA ATACCCTGAA AGGATGAACC GTCATGTAGA TGCATAATCA

3721 CATCGCTATT ACCATGGTGA TGCGGTTTTG GCAGTACATC AATGGGCGTG GATAGCGGTT
     GTAGCGATAA TGGTACCACT ACGCCAAAAC CGTCATGTAG TTACCCGCAC CTATCGCCAA

3781 TGACTCACGG GGATTTCCAA GTCTCCACCC CATTGACGTC AATGGGAGTT TGTTTTGGCA
     ACTGAGTGCC CCTAAAGGTT CAGAGGTGGG GTAACTGCAG TTACCCTCAA ACAAAACCGT

3841 CCAAAATCAA CGGGACTTTC CAAAATGTCG TAACAACTCC GCCCCATTGA CGCAAATGGG
     GGTTTTAGTT GCCCTGAAAG GTTTTACAGC ATTGTTGAGG CGGGGTAACT GCGTTTACCC

3901 CGGTAGGCGT GTACGGTGGG AGGTCTATAT AAGCAGAGCT CGTTTAGTGA ACCGTCAGAT
     GCCATCCGCA CATGCCACCC TCCAGATATA TTCGTCTCGA GCAAATCACT TGGCAGTCTA

3961 CGCCTGGAGA CGCCATCCAC GCTGTTTTGA CCTCCATAGA AGACACCGGG ACCGATCCAG
     GCGGACCTCT GCGGTAGGTG CGACAAAACT GGAGGTATCT TCTGTGGCCC TGGCTAGGTC

4021 CCTCCGCGGC CGGGAACGGT GCATTGGAAC GCGGATTCCC CGTGCCAAGA GTGACGTAAG
     GGAGGCGCCG GCCCTTGCCA CGTAACCTTG CGCCTAAGGG GCACGGTTCT CACTGCATTC

4081 TACCGCCTAT AGAGTCTATA GGCCCACCTA GTTGTGACCG GCGCCTAGTG TTGACAATTA
     ATGGCGGATA TCTCAGATAT CCGGGTGGAT CAACACTGGC CGCGGATCAC AACTGTTAAT

4141 ATCATCGGCA TAGTATATCG GCATAGTATA ATACGACTCA CTATAGGAGG CCACCATGT
     TAGTAGCCGT ATCATATAGC CGTATCATAT TATGCTGAGT GATATCCTCC CGGTGGTACA
                                                    [SEQ ID NO: 18] (HyTK →)
                                                                       M
4201 CGACTACTAA CCTTCTTCTC TTTCCTACAG CTGAGATCAC CGGTAGGAGG GCCATCATGA
     GCTGATGATT GGAAGAAGAG AAAGGATGTC GACTCTAGTG GCCATCCTCC CGGTAGTACT

K   K   P   E   L   T   A   T   S   V   A   K   F   L   I   E   K   F   D   S
4261 AAAAGCCTGA ACTCACCGCG ACGTCTGTCG CGAAGTTTCT GATCGAAAAG TTCGACAGCG
     TTTTCGGACT TGAGTGGCGC TGCAGACAGC GCTTCAAAGA CTAGCTTTTC AAGCTGTCGC
```

Figure 10 (cont'd)

```
           V  S  D  L     M  Q  L     S  E  G     E  E  S  R     A  F  S     F  D  V
4321 TCTCCGACCT GATGCAGCTC TCGGAGGGCG AAGAATCTCG TGCTTTCAGC TTCGATGTAG
     AGAGGCTGGA CTACGTCGAG AGCCTCCCGC TTCTTAGAGC ACGAAAGTCG AAGCTACATC

G  G  R  G     Y  V  L     R  V  N     S  C  A  D     G  F  Y     K  D  R
4381 GAGGGCGTGG ATATGTCCTG CGGGTAAATA GCTGCGCCGA TGGTTTCTAC AAAGATCGTT
     CTCCCGCACC TATACAGGAC GCCCATTTAT CGACGCGGCT ACCAAAGATG TTTCTAGCAA

Y  V  Y  R     H  F  A     S  A  A     L  P  I  P     E  V  L     D  I  G
4441 ATGTTTATCG GCACTTTGCA TCGGCCGCGC TCCCGATTCC GGAAGTGCTT GACATTGGGG
     TACAAATAGC CGTGAAACGT AGCCGGCGCG AGGGCTAAGG CCTTCACGAA CTGTAACCCC

E  F  S  E     S  L  T     Y  C  I     S  R  R  A     Q  G  V     T  L  Q
4501 AATTCAGCGA GAGCCTGACC TATTGCATCT CCCGCCGTGC ACAGGGTGTC ACGTTGCAAG
     TTAAGTCGCT CTCGGACTGG ATAACGTAGA GGGCGGCACG TGTCCCACAG TGCAACGTTC

D  L  P  E     T  E  L     P  A  V     L  Q  P  V     A  E  L     M  D  A
4561 ACCTGCCTGA AACCGAACTG CCCGCTGTTC TGCAACCCGT CGCGGAGCTC ATGGATGCGA
     TGGACGGACT TTGGCTTGAC GGGCGACAAG ACGTTGGGCA GCGCCTCGAG TACCTACGCT

I  A  A  A     D  L  S     Q  T  S     G  F  G  P     F  G  P     Q  G  I
4621 TCGCTGCGGC CGATCTTAGC CAGACGAGCG GGTTCGGCCC ATTCGGACCG CAAGGAATCG
     AGCGACGCCG GCTAGAATCG GTCTGCTCGC CCAAGCCGGG TAAGCCTGGC GTTCCTTAGC

G  Q  Y  T     T  W  R     D  F  I     C  A  I  A     D  P  H     V  Y  H
4681 GTCAATACAC TACATGGCGT GATTTCATAT GCGCGATTGC TGATCCCCAT GTGTATCACT
     CAGTTATGTG ATGTACCGCA CTAAAGTATA CGCGCTAACG ACTAGGGGTA CACATAGTGA

W  Q  T  V     M  D  D     T  V  S     A  S  V  A     Q  A  L     D  E  L
4741 GGCAAACTGT GATGGACGAC ACCGTCAGTG CGTCCGTCGC GCAGGCTCTC GATGAGCTGA
     CCGTTTGACA CTACCTGCTG TGGCAGTCAC GCAGGCAGCG CGTCCGAGAG CTACTCGACT

M  L  W  A     E  D  C     P  E  V     R  H  L  V     H  A  D     F  G  S
4801 TGCTTTGGGC CGAGGACTGC CCCGAAGTCC GGCACCTCGT GCACGCGGAT TTCGGCTCCA
     ACGAAACCCG GCTCCTGACG GGGCTTCAGG CCGTGGAGCA CGTGCGCCTA AAGCCGAGGT

N  N  V  L     T  D  N     G  R  I     T  A  V  I     D  W  S     E  A  M
4861 ACAATGTCCT GACGGACAAT GGCCGCATAA CAGCGGTCAT TGACTGGAGC GAGGCGATGT
     TGTTACAGGA CTGCCTGTTA CCGGCGTATT GTCGCCAGTA ACTGACCTCG CTCCGCTACA

F  G  D  S     Q  Y  E     V  A  N     I  F  F  W     R  P  W     L  A  C
4921 TCGGGGATTC CCAATACGAG GTCGCCAACA TCTTCTTCTG GAGGCCGTGG TTGGCTTGTA
     AGCCCCTAAG GGTTATGCTC CAGCGGTTGT AGAAGAAGAC CTCCGGCACC AACCGAACAT
```

Figure 10 (cont'd)

```
            M   E   Q   Q       T   R   Y       F   E   R       R   H   P       E   L   A   G       S   P   R
     4981   TGGAGCAGCA  GACGCGCTAC  TTCGAGCGGA  GGCATCCGGA  GCTTGCAGGA  TCGCCGCGGC
            ACCTCGTCGT  CTGCGCGATG  AAGCTCGCCT  CCGTAGGCCT  CGAACGTCCT  AGCGGCGCCG

L   R   A   Y       M   L   R       I   G   L       D   Q   L   Y       Q   S   L       V   D   G
     5041   TCCGGGCGTA  TATGCTCCGC  ATTGGTCTTG  ACCAACTCTA  TCAGAGCTTG  GTTGACGGCA
            AGGCCCGCAT  ATACGAGGCG  TAACCAGAAC  TGGTTGAGAT  AGTCTCGAAC  CAACTGCCGT

N   F   D   D       A   A   W       A   Q   G       R   C   D   A       I   V   R       S   G   A
     5101   ATTTCGATGA  TGCAGCTTGG  GCGCAGGGTC  GATGCGACGC  AATCGTCCGA  TCCGGAGCCG
            TAAAGCTACT  ACGTCGAACC  CGCGTCCCAG  CTACGCTGCG  TTAGCAGGCT  AGGCCTCGGC

G   T   V   G       R   T   Q       I   A   R       R   S   A   A       V   W   T       D   G   C
     5161   GGACTGTCGG  GCGTACACAA  ATCGCCCGCA  GAAGCGCGGC  CGTCTGGACC  GATGGCTGTG
            CCTGACAGCC  CGCATGTGTT  TAGCGGGCGT  CTTCGCGCCG  GCAGACCTGG  CTACCGACAC

V   E   V   A       S   A   F       D   Q   A       A   R   S   R       G   H   S       N   R   R
     5221   TAGAAGTCGC  GTCTGCGTTC  GACCAGGCTG  CGCGTTCTCG  CGGCCATAGC  AACCGACGTA
            ATCTTCAGCG  CAGACGCAAG  CTGGTCCGAC  GCGCAAGAGC  GCCGGTATCG  TTGGCTGCAT

T   A   L   R       P   R   R       Q   Q   E       A   T   E   V       R   P   E       Q   K   M
     5281   CGGCGTTGCG  CCCTCGCCGG  CAGCAAGAAG  CCACGGAAGT  CCGCCCGGAG  CAGAAAATGC
            GCCGCAACGC  GGGAGCGGCC  GTCGTTCTTC  GGTGCCTTCA  GGCGGGCCTC  GTCTTTTACG

P   T   L   L       R   V   Y       I   D   G       P   H   G   M       G   K   T       T   T   T
     5341   CCACGCTACT  GCGGGTTTAT  ATAGACGGTC  CCCACGGGAT  GGGGAAAACC  ACCACCACGC
            GGTGCGATGA  CGCCCAAATA  TATCTGCCAG  GGGTGCCCTA  CCCCTTTTGG  TGGTGGTGCG

Q   L   L   V       A   L   G       S   R   D       D   I   V   Y       V   P   E       P   M   T
     5401   AACTGCTGGT  GGCCCTGGGT  TCGCGCGACG  ATATCGTCTA  CGTACCCGAG  CCGATGACTT
            TTGACGACCA  CCGGGACCCA  AGCGCGCTGC  TATAGCAGAT  GCATGGGCTC  GGCTACTGAA

Y   W   R   V       L   G   A       S   E   T       I   A   N   I       Y   T   T       Q   H   R
     5461   ACTGGCGGGT  GCTGGGGGCT  TCCGAGACAA  TCGCGAACAT  CTACACCACA  CAACACCGCC
            TGACCGCCCA  CGACCCCCGA  AGGCTCTGTT  AGCGCTTGTA  GATGTGGTGT  GTTGTGGCGG

L   D   Q   G       E   I   S       A   G   D       A   A   V   V       M   T   S       A   Q   I
     5521   TCGACCAGGG  TGAGATATCG  GCCGGGACG   CGGCGGTGGT  AATGACAAGC  GCCCAGATAA
            AGCTGGTCCC  ACTCTATAGC  CGGCCCCTGC  GCCGCCACCA  TTACTGTTCG  CGGGTCTATT

T   M   G   M       P   Y   A       V   T   D       A   V   L   A       P   H   I       G   G   E
     5581   CAATGGGCAT  GCCTTATGCC  GTGACCGACG  CCGTTCTGGC  TCCTCATATC  GGGGGGGAGG
            GTTACCCGTA  CGGAATACGG  CACTGGCTGC  GGCAAGACCG  AGGAGTATAG  CCCCCCCTCC
```

Figure 10 (cont'd)

```
           A   G   S   S       H   A   P       P   P   A       L   T   L   I       F   D   R       H   P   I
      5641 CTGGGAGCTC ACATGCCCCG CCCCCGGCCC TCACCCTCAT CTTCGACCGC CATCCCATCG
           GACCCTCGAG TGTACGGGGC GGGGGCCGGG AGTGGGAGTA GAAGCTGGCG GTAGGGTAGC

A   A   L   L       C   Y   P       A   A   R       Y   L   M       G   S   M   T       P   Q   A
      5701 CCGCCCTCCT GTGCTACCCG GCCGCGCGGT ACCTTATGGG CAGCATGACC CCCCAGGCCG
           GGCGGGAGGA CACGATGGGC CGGCGCGCCA TGGAATACCC GTCGTACTGG GGGGTCCGGC

V   L   A   F       V   A   L       I   P   P       T   L   P       G   T   N   I       V   L   G
      5761 TGCTGGCGTT CGTGGCCCTC ATCCCGCCGA CCTTGCCCGG CACCAACATC GTGCTTGGGG
           ACGACCGCAA GCACCGGGAG TAGGGCGGCT GGAACGGGCC GTGGTTGTAG CACGAACCCC

A   L   P   E       D   R   H       I   D   R       L   A   K   R       Q   R   P       G   E   R
      5821 CCCTTCCGGA GGACAGACAC ATCGACCGCC TGGCCAAACG CCAGCGCCCC GGCGAGCGGC
           GGGAAGGCCT CCTGTCTGTG TAGCTGGCGG ACCGGTTTGC GGTCGCGGGG CCGCTCGCCG

L   D   L   A       M   L   A       A   I   R       R   V   Y   G       L   L   A       N   T   V
      5881 TGGACCTGGC TATGCTGGCT GCGATTCGCC GCGTTTACGG GCTACTTGCC AATACGGTGC
           ACCTGGACCG ATACGACCGA CGCTAAGCGG CGCAAATGCC CGATGAACGG TTATGCCACG

R   Y   L   Q       C   G   G       S   W   R       E   D   W   G       Q   L   S       G   T   A
      5941 GGTATCTGCA GTGCGGCGGG TCGTGGCGGG AGGACTGGGG ACAGCTTTCG GGGACGGCCG
           CCATAGACGT CACGCCGCCC AGCACCGCCC TCCTGACCCC TGTCGAAAGC CCCTGCCGGC

V   P   P   Q       G   A   E       P   Q   S       N   A   G   P       R   P   H       I   G   D
      6001 TGCCGCCCCA GGGTGCCGAG CCCCAGAGCA ACGCGGGCCC ACGACCCCAT ATCGGGGACA
           ACGGCGGGGT CCCACGGCTC GGGGTCTCGT TGCGCCCGGG TGCTGGGGTA TAGCCCCTGT

T   L   F   T       L   F   R       A   P   E       L   L   A   P       N   G   D       L   Y   N
      6061 CGTTATTTAC CCTGTTTCGG GCCCCCGAGT TGCTGGCCCC CAACGGCGAC CTGTATAACG
           GCAATAAATG GGACAAAGCC CGGGGGCTCA ACGACCGGGG GTTGCCGCTG GACATATTGC

V   F   A   W       A   L   D       V   L   A       K   R   L   R       S   M   H       V   F   I
      6121 TGTTTGCCTG GGCCTTGGAC GTCTTGGCCA AACGCCTCCG TTCCATGCAC GTCTTTATCC
           ACAAACGGAC CCGGAACCTG CAGAACCGGT TTGCGGAGGC AAGGTACGTG CAGAAATAGG

L   D   Y   D       Q   S   P       A   G   C       R   D   A   L       L   Q   L       T   S   G
      6181 TGGATTACGA CCAATCGCCC GCCGGCTGCC GGGACGCCCT GCTGCAACTT ACCTCCGGGA
           ACCTAATGCT GGTTAGCGGG CGGCCGACGG CCCTGCGGGA CGACGTTGAA TGGAGGCCCT

M   V   Q   T       H   V   T       T   P   G       S   I   P   T       I   C   D       L   A   R
      6241 TGGTCCAGAC CCACGTCACC ACCCCCGGCT CCATACCGAC GATATGCGAC CTGGCGCGCA
           ACCAGGTCTG GGTGCAGTGG TGGGGGCCGA GGTATGGCTG CTATACGCTG GACCGCGCGT

T   F   A   R       E   M   G       E   A   N       *   (bGh pA →)
      6301 CGTTTGCCCG GGAGATGGGG GAGGCTAACT GAGTCGAGAA TTCGCTAGAG GGCCCTATTC
           GCAAACGGGC CCTCTACCCC CTCCGATTGA CTCAGCTCTT AAGCGATCTC CCGGGATAAG
```

Figure 10 (last pg)

```
6361 TATAGTGTCA CCTAAATGCT AGAGCTCGCT GATCAGCCTC GACTGTGCCT TCTAGTTGCC
     ATATCACAGT GGATTTACGA TCTCGAGCGA CTAGTCGGAG CTGACACGGA AGATCAACGG

6421 AGCCATCTGT TGTTTGCCCC TCCCCCGTGC CTTCCTTGAC CCTGGAAGGT GCCACTCCCA
     TCGGTAGACA ACAAACGGGG AGGGGGCACG GAAGGAACTG GGACCTTCCA CGGTGAGGGT

6481 CTGTCCTTTC CTAATAAAAT GAGGAAATTG CATCGCATTG TCTGAGTAGG TGTCATTCTA
     GACAGGAAAG GATTATTTTA CTCCTTTAAC GTAGCGTAAC AGACTCATCC ACAGTAAGAT

6541 TTCTGGGGGG TGGGGTGGGG CAGGACAGCA AGGGGGAGGA TTGGGAAGAC AATAGCAGGC
     AAGACCCCCC ACCCCACCCC GTCCTGTCGT TCCCCCTCCT AACCCTTCTG TTATCGTCCG

6601 ATGCGCAGGG CCCAATTGCT CGAGCGGCCG CAATAAAATA TCTTTATTTT CATTACATCT
     TACGCGTCCC GGGTTAACGA GCTCGCCGGC GTTATTTTAT AGAAATAAAA GTAATGTAGA

6661 GTGTGTTGGT TTTTTGTGTG AATCGTAACT AACATACGCT CTCCATCAAA ACAAAACGAA
     CACACAACCA AAAAACACAC TTAGCATTGA TTGTATGCGA GAGGTAGTTT TGTTTTGCTT

6721 ACAAAACAAA CTAGCAAAAT AGGCTGTCCC CAGTGCAAGT GCAGGTGCCA GAACATTTCT
     TGTTTTGTTT GATCGTTTTA TCCGACAGGG GTCACGTTCA CGTCCACGGT CTTGTAAAGA

6781 CTA
     GAT
```

IL13-IgG4-CD4tm-CD28-41BB-Z 1520 bp

SEQUENCE LISTING

<160> NUMBER OF SEQ ID NOS: 18

<210> SEQ ID NO 1
<211> LENGTH: 102
<212> TYPE: DNA
<213> ORGANISM: Homo sapiens
<220> FEATURE:
<221> NAME/KEY: misc_feature
<222> LOCATION: (4)..(9)
<223> OTHER INFORMATION: EcoRI restriction site

<400> SEQUENCE: 1
tatgaattca tggcgctttt gttgaccacg gtcattgctc tcacttgcct tggcggcttt    60
gcctccccag gccctgtgcc tccctctaca gccctcaggt ac                        102

<210> SEQ ID NO 2
<211> LENGTH: 101
<212> TYPE: DNA
<213> ORGANISM: Homo sapiens

<400> SEQUENCE: 2
gttgatgctc cataccatgc tgccattgca gagcggagcc ttctggttct gggtgatgtt    60
gaccagctcc tcaatgaggt acctgagggc tgtagaggga g                         101

<210> SEQ ID NO 3
<211> LENGTH: 100
<212> TYPE: DNA
<213> ORGANISM: Homo sapiens

<400> SEQUENCE: 3
ctctgggtct tctcgatggc actgcagcct gacacgttga tcagggattc cagggctgca    60
cagtacatgc cagctgtcag gttgatgctc cataccatgc                          100

<210> SEQ ID NO 4
<211> LENGTH: 100
<212> TYPE: DNA
<213> ORGANISM: Homo sapiens

<400> SEQUENCE: 4
cctcgatttt ggtgtctcgg acatgcaagc tggaaaactg cccagctgag accttgtgcg    60
ggcagaatcc gctcagcatc ctctgggtct tctcgatggc                          100

<210> SEQ ID NO 5
<211> LENGTH: 96
<212> TYPE: DNA
<213> ORGANISM: Homo sapiens
<220> FEATURE:
<221> NAME/KEY: misc_feature
<222> LOCATION: (3)..(8)
<223> OTHER INFORMATION: BamHI restriction site

<400> SEQUENCE: 5
tcggatcctc agttgaaccg tccctcgcga aaaagtttct ttaaatgtaa gagcaggtcc    60
tttacaaact gggccacctc gattttggtg tctcgg                                   96

<210> SEQ ID NO 6
<211> LENGTH: 39
<212> TYPE: DNA
<213> ORGANISM: Homo sapiens

<400> SEQUENCE: 6
caacctgaca gctggcatgt actgtgcagc cctggaatc                                39

<210> SEQ ID NO 7
<211> LENGTH: 39
<212> TYPE: DNA
<213> ORGANISM: Homo sapiens

<400> SEQUENCE: 7
gattccaggg ctgcacagta catgccagct gtcaggttg                                39

<210> SEQ ID NO 8
<211> LENGTH: 43
<212> TYPE: DNA
<213> ORGANISM: Homo sapiens
<220> FEATURE:
<221> NAME/KEY: misc_feature
<222> LOCATION: (4)..(9)
<223> OTHER INFORMATION: XbaI restriction site

<400> SEQUENCE: 8
atctctagag ccgccaccat gcttctcctg gtgacaagcc ttc                           43

<210> SEQ ID NO 9
<211> LENGTH: 34
<212> TYPE: DNA
<213> ORGANISM: Homo sapiens

<400> SEQUENCE: 9
gagggaggca cagggcctgg gatcaggagg aatg                                     34

<210> SEQ ID NO 10
<211> LENGTH: 34
<212> TYPE: DNA
<213> ORGANISM: Homo sapiens

<400> SEQUENCE: 10
cattcctcct gatcccaggc cctgtgcctc cctc                                     34

<210> SEQ ID NO 11
<211> LENGTH: 35
<212> TYPE: DNA
<213> ORGANISM: Homo sapiens

<400> SEQUENCE: 11
gggaccatat ttggactcgt tgaaccgtcc ctcgc                                    35

<210> SEQ ID NO 12
<211> LENGTH: 35
<212> TYPE: DNA
<213> ORGANISM: Homo sapiens

<400> SEQUENCE: 12
gcgagggacg gttcaacgag tccaaatatg gtccc                                    35

<210> SEQ ID NO 13

```
<211> LENGTH: 26
<212> TYPE: DNA
<213> ORGANISM: Homo sapiens
<220> FEATURE:
<221> NAME/KEY: misc_feature
<222> LOCATION: (3)..(10)
<223> OTHER INFORMATION: NotI restriction site

<400> SEQUENCE: 13
atgcggccgc tcagcgaggg ggcagg                                          26

<210> SEQ ID NO 14
<211> LENGTH: 6783
<212> TYPE: DNA
<213> ORGANISM: Artificial Sequence
<220> FEATURE:
<223> OTHER INFORMATION: plasmid DNA vector incorporating human, simian
      virus 40, E. coli, cytomegalovirus and bovine sequences

<400> SEQUENCE: 14
tcgaaggatc tgcgatcgct ccggtgcccg tcagtgggca gagcgcacat cgcccacagt     60
ccccgagaag ttggggggag gggtcggcaa ttgaaccggt gcctagagaa ggtggcgcgg    120
ggtaaactgg gaaagtgatg tcgtgtactg gctccgcctt tttcccgagg gtgggggaga    180
accgtatata agtgcagtag tcgccgtgaa cgttcttttt cgcaacgggt ttgccgccag    240
aacacagctg aagcttcgag gggctcgcat ctctccttca cgcgcccgcc gccctacctg    300
aggccgccat ccacgccggt tgagtcgcgt tctgccgcct ccgcctgtg gtgcctcctg     360 aactgcgtcc gccgtctagg taagtttaaa gctcaggtcg agaccgggcc tttgtccggc    420
gctcccttgg agcctaccta gactcagccg gctctccacg cttgtgctga ccctgcttgc    480
tcaactctac gtctttgttt cgttttctgt tctgcgccgt tacagatcca agctgtgacc    540
ggcgcctacg taagtgatat ctactagatt tatcaaaaag agtgttgact tgtgagcgct    600
cacaattgat acggattcat cgagagggac acgtcgacta ctaaccttct tctctttcct    660
acagctgaga tcaccctaga gccgccacca tgcttctcct ggtgacaagc cttctgctct    720
gtgagttacc acacccagca ttcctcctga tcccaggccc tgtgcctccc tctacagccc    780
tcaggtacct cattgaggag ctggtcaaca tcacccagaa ccagaaggct ccgctctgca    840
atggcagcat ggtatggagc atcaacctga gctggcat gtactgtgca gccctggaat      900
ccctgatcaa cgtgtcaggc tgcagtgcca tcgagaagac ccagaggatg ctgagcggat    960
tctgcccgca caaggtctca gctgggcagt tttccagctt gcatgtccga gacaccaaaa   1020
tcgaggtggc ccagtttgta aaggacctgc tcttacattt aaagaaactt tttcgcgagg   1080
gacggttcaa cgagtccaaa tatggtcccc catgcccacc atgcccagca cctgagttcc   1140
tggggggacc atcagtcttc ctgttccccc caaaacccaa ggacactctc atgatctccc   1200
ggacccctga ggtcacgtgc gtggtggtgg acgtgagcca ggaagacccc gaggtccagt   1260
tcaactggta cgtggatggc gtggaggtgc ataatgccaa gacaaagccg cgggaggagc   1320
agttcaacag cacgtaccgt gtggtcagcg tcctcaccgt cctgcaccag gactggctga   1380
acggcaagga gtacaagtgc aaggtctcca acaaaggcct cccgtcctcc atcgagaaaa   1440
ccatctccaa agccaagggg cagccccgag agccacaggt gtacaccctg cccccatccc   1500
aggaggagat gaccaagaac caggtcagcc tgacctgcct ggtcaaaggc ttctacccca   1560
gcgacatcgc cgtggagtgg gagagcaatg ggcagccgga gaacaactac aagaccacgc   1620
ctcccgtgct ggactccgac ggctccttct tcctctacag caggctaacc gtggacaaga   1680
```

```
gcaggtggca ggaggggaat gtcttctcat gctccgtgat gcatgaggct ctgcacaacc    1740
actacacaca gaagagcctc tccctgtccc taggtaaaat ggccctgatt gtgctggggg    1800
gcgtcgccgg cctcctgctt ttcattgggc taggcatctt cttcagagtg aagttcagca    1860
ggagcgcaga cgcccccgcg taccagcagg gccagaacca gctctataac gagctcaatc    1920
taggacgaag agaggagtac gatgttttgg acaagagacg tggccgggac cctgagatgg    1980
ggggaaagcc gagaaggaag aaccctcagg aaggcctgta caatgaactg cagaaagata    2040
agatggcgga ggcctacagt gagattggga tgaaaggcga gcgccggagg ggcaaggggc    2100
acgatggcct ttaccagggt ctcagtacag ccaccaagga cacctacgac gcccttcaca    2160
tgcaggccct gccccctcgc tgagcggccg gcgaaggagg cctagatcta tcgattgtac    2220
agctagctcg acatgataag atacattgat gagtttggac aaaccacaac tagaatgcag    2280
tgaaaaaaat gctttatttg tgaaatttgt gatgctattg ctttatttgt gaaatttgtg    2340
atgctattgc tttatttgta accattataa gctgcaataa acaagttaac aacaacaatt    2400
gcattcattt tatgtttcag gttcagggg aggtgtggga ggttttttaa agcaagtaaa    2460
acctctacaa atgtggtaga tccatttaaa tgttagcgaa gaacatgtga gcaaaaggcc    2520
agcaaaaggc caggaaccgt aaaaaggccg cgttgctggc gttttttccat aggctccgcc    2580 ccctgacga gcatcacaaa aatcgacgct caagtcagag gtggcgaaac ccgacaggac    2640
tataaagata ccaggcgttt ccccctggaa gctccctcgt gcgctctcct gttccgaccc    2700
tgccgcttac cggatacctg tccgcctttc tcccttcggg aagcgtggcg ctttctcaat    2760
gctcacgctg taggtatctc agttcggtgt aggtcgttcg ctccaagctg gctgtgtgc    2820 acgaaccccc cgttcagccc gaccgctgcg ccttatccgg taactatcgt cttgagtcca    2880
acccggtaag acacgactta tcgccactgg cagcagccac tggtaacagg attagcagag    2940
cgaggtatgt aggcggtgct acagagttct tgaagtggtg gcctaactac ggctacacta    3000
gaagaacagt atttggtatc tgcgctctgc tgaagccagt taccttcgga aaaagagttg    3060
gtagctcttg atccggcaaa caaaccaccg ctggtagcgg tggttttttt gtttgcaagc    3120
agcagattac gcgcagaaaa aaaggatctc aagaagatcc tttgatcttt tctacggggt    3180
ctgacgctca gtggaacgaa aactcacgtt aagggatttt ggtcatggct agttaattaa    3240
gctgcaataa acaatcatta ttttcattgg atctgtgtgt tggttttttg tgtgggcttg    3300 ggggagggg aggccagaat gactccaaga gctacaggaa ggcaggtcag agaccccact    3360
ggacaaacag tggctggact ctgcaccata acacacaatc aacaggggag tgagctggat    3420
cgagctagag tccgttacat aacttacggt aaatggcccg cctggctgac cgcccaacga    3480
cccccgccca ttgacgtcaa taatgacgta tgttcccata gtaacgccaa tagggacttt    3540
ccattgacgt caatgggtgg agtatttacg gtaaactgcc cacttggcag tacatcaagt    3600
gtatcatatg ccaagtacgc ccccctattga cgtcaatgac ggtaaatggc ccgcctggca    3660
ttatgcccag tacatgacct tatgggactt tcctacttgg cagtacatct acgtattagt    3720
catcgctatt accatggtga tgcggttttg gcagtacatc aatgggcgtg gatagcggtt    3780
tgactcacgg ggatttccaa gtctccaccc cattgacgtc aatgggagtt tgttttggca    3840
ccaaaatcaa cgggactttc caaaatgtcg taacaactcc gccccattga cgcaaatggg    3900
cggtaggcgt gtacggtggg aggtctatat aagcagagct cgtttagtga accgtcagat    3960
cgcctggaga cgccatccac gctgttttga cctccataga agacaccggg accgatccag    4020
cctccgcggc cgggaacggt gcattggaac gcggattccc cgtgccaaga gtgacgtaag    4080
```

-continued

```
taccgcctat agagtctata ggcccaccta gttgtgaccg gcgcctagtg ttgacaatta      4140
atcatcggca tagtatatcg gcatagtata atacgactca ctataggagg gccaccatgt      4200
cgactactaa ccttcttctc tttcctacag ctgagatcac cggtaggagg gccatcatga      4260
aaaagcctga actcaccgcg acgtctgtcg cgaagtttct gatcgaaaag ttcgacagcg      4320
tctccgacct gatgcagctc tcggagggcg aagaatctcg tgctttcagc ttcgatgtag      4380
gagggcgtgg atatgtcctg cgggtaaata gctgcgccga tggtttctac aaagatcgtt      4440
atgtttatcg gcactttgca tcggccgcgc tcccgattcc ggaagtgctt gacattgggg      4500
aattcagcga gagcctgacc tattgcatct cccgccgtgc acagggtgtc acgttgcaag      4560
acctgcctga aaccgaactg cccgctgttc tgcaacccgt cgcggagctc atggatgcga      4620
tcgctgcggc cgatcttagc cagacgagcg ggttcggccc attcggaccg caaggaatcg      4680
gtcaatacac tacatggcgt gatttcatat gcgcgattgc tgatccccat gtgtatcact      4740
ggcaaactgt gatggacgac accgtcagtg cgtccgtcgc gcaggctctc gatgagctga      4800
tgctttgggc cgaggactgc cccgaagtcc ggcacctcgt gcacgcggat ttcggctcca      4860
acaatgtcct gacggacaat ggccgcataa cagcggtcat tgactggagc gaggcgatgt      4920
tcggggattc ccaatacgag gtcgccaaca tcttcttctg gaggccgtgg ttggcttgta      4980
tggagcagca gacgcgctac ttcgagcgga ggcatccgga gcttgcagga tcgccgcggc      5040
tccgggcgta tatgctccgc attggtcttg accaactcta tcagagcttg gttgacggca      5100
atttcgatga tgcagcttgg gcgcagggtc gatgcgacgc aatcgtccga tccggagccg      5160
ggactgtcgg gcgtacacaa atcgcccgca gaagcgcggc cgtctggacc gatggctgtg      5220
tagaagtcgc gtctgcgttc gaccaggctg cgcgttctcg cggccatagc aaccgacgta      5280
cggcgttgcg ccctcgccgg cagcaagaag ccacggaagt ccgcccggag cagaaaatgc      5340
ccacgctact gcgggtttat atagacggtc cccacgggga ggggaaaacc accaccacgc      5400
aactgctggt ggccctgggt tcgcgcgacg atatcgtcta cgtacccgag ccgatgactt      5460
actggcgggt gctgggggct tccgagacaa tcgcgaacat ctacaccaca caacaccgcc      5520
tcgaccaggg tgagatatcg gccggggacg cggcggtggt aatgacaagc gcccagataa      5580
caatgggcat gccttatgcc gtgaccgacg ccgttctggc tcctcatatc gggggggagg      5640
ctgggagctc acatgccccg cccccggccc tcaccctcat cttcgaccgc catcccatcg      5700
ccgccctcct gtgctacccg gccgcgcggt accttatggg cagcatgacc ccccaggccg      5760
tgctggcgtt cgtggccctc atcccgccga ccttgcccgg caccaacatc gtgcttgggg      5820
cccttccgga ggacagacac atcgaccgcc tggccaaacg ccagcgcccc ggcgagcggc      5880
tggacctggc tatgctggct gcgattcgcc gcgtttacgg gctacttgcc aatacggtgc      5940
ggtatctgca gtgcggcggg tcgtggcggg aggactgggg acagcttttcg gggacggccg      6000 tgccgcccca gggtgccgag ccccagagca acgcgggccc acgaccccat atcggggaca      6060
cgttatttac cctgtttcgg gcccccgagt tgctggcccc caacggcgac ctgtataacg      6120
tgtttgcctg ggccttggac gtcttggcca aacgcctccg ttccatgcac gtctttatcc      6180
tggattacga ccaatcgccc gccggctgcc gggacgccct gctgcaactt acctccggga      6240
tggtccagac ccacgtcacc accccggct ccataccgac gatatgcgac ctggcgcgca      6300
cgtttgcccg ggagatgggg gaggctaact gagtcgagaa ttcgctagag ggccctattc      6360
tatagtgtca cctaaatgct agagctcgct gatcagcctc gactgtgcct tctagttgcc      6420
```

```
agccatctgt tgtttgcccc tccccgtgc cttccttgac cctggaaggt gccactccca    6480
ctgtcctttc ctaataaaat gaggaaattg catcgcattg tctgagtagg tgtcattcta    6540
ttctgggggg tggggtgggg caggacagca aggggagga ttgggaagac aatagcaggc    6600
atgcgcaggg cccaattgct cgagcggccg caataaaata tctttatttt cattacatct    6660
gtgtgttggt tttttgtgtg aatcgtaact aacatacgct ctccatcaaa acaaaacgaa    6720
acaaaacaaa ctagcaaaat aggctgtccc cagtgcaagt gcaggtgcca aacatttct    6780 cta                                                                  6783

<210> SEQ ID NO 15
<211> LENGTH: 1491
<212> TYPE: DNA
<213> ORGANISM: Homo sapiens

<400> SEQUENCE: 15
atgcttctcc tggtgacaag ccttctgctc tgtgagttac cacacccagc attcctcctg     60
atcccaggcc ctgtgcctcc ctctacagcc ctcaggtacc tcattgagga gctggtcaac    120
atcacccaga accagaaggc tccgctctgc aatggcagca tggtatggag catcaacctg    180
acagctggca tgtactgtgc agccctggaa tccctgatca acgtgtcagg ctgcagtgcc    240
atcgagaaga cccagaggat gctgagcgga ttctgcccgc acaaggtctc agctgggcag    300
ttttccagct gcatgtccg agacaccaaa atcgaggtgg cccagtttgt aaaggacctg    360
ctcttacatt taaagaaact ttttcgcgag ggacggttca acgagtccaa atatggtccc    420
ccatgcccac catgcccagc acctgagttc ctgggggac catcagtctt cctgttcccc    480 caaaaccca aggacactct catgatctcc cggacccctg aggtcacgtg cgtggtggtg    540
gacgtgagcc aggaagaccc cgaggtccag ttcaactggt acgtggatgg cgtggaggtg    600
cataatgcca agacaaagcc gcgggaggag cagttcaaca gcacgtaccg tgtggtcagc    660
gtcctcaccg tcctgcacca ggactggctg aacggcaagg agtacaagtg caaggtctcc    720
aacaaaggcc tcccgtcctc catcgagaaa accatctcca agccaaagg gcagccccga    780 gagccacagg tgtacaccct gccccccatcc caggaggaga tgaccaagaa ccaggtcagc    840
ctgacctgcc tggtcaaagg cttctacccc agcgacatcg ccgtggagtg ggagagcaat    900
gggcagccgg agaacaacta caagaccacg cctcccgtgc tggactccga cggctccttc    960
ttcctctaca gcaggctaac cgtggacaag agcaggtggc aggagggaa tgtcttctca   1020 tgctccgtga tgcatgaggc tctgcacaac cactacacac agaagagcct ctccctgtct   1080
ctgggtaaaa tggccctgat tgtgctgggg ggcgtcgccg gcctcctgct tttcattggg   1140
ctaggcatct tcttcagagt gaagttcagc aggagcgcag acgcccccgc gtaccagcag   1200
ggccagaacc agctctataa cgagctcaat ctaggacgaa gagaggagta cgatgttttg   1260
gacaagagac gtggccggga ccctgagatg ggggaaagc cgagaaggaa gaaccctcag   1320
gaaggcctgt acaatgaact gcagaaagat aagatggcgg aggcctacag tgagattggg   1380
atgaaaggcg agcgccggag gggcaagggg cacgatggcc tttaccaggg tctcagtaca   1440
gccaccaagg acacctacga cgcccttcac atgcaggccc tgcccctcg c             1491

<210> SEQ ID NO 16
<211> LENGTH: 6783
<212> TYPE: DNA
<213> ORGANISM: Artificial Sequence
<220> FEATURE:
<223> OTHER INFORMATION: plasmid DNA vector incorporating human, simian
``` virus 40, E. coli, cytomegalovirus and bovine sequences

<400> SEQUENCE: 16

```
tagagaaatg ttctggcacc tgcacttgca ctggggacag cctatttgc tagtttgttt      60
tgtttcgttt tgttttgatg gagagcgtat gttagttacg attcacacaa aaaaccaaca    120
cacagatgta atgaaaataa agatatttta ttgcggccgc tcgagcaatt gggccctgcg    180
catgcctgct attgtcttcc caatcctccc ccttgctgtc ctgccccacc ccaccccca     240
gaatagaatg acacctactc agacaatgcg atgcaatttc ctcattttat taggaaagga    300
cagtgggagt ggcaccttcc agggtcaagg aaggcacggg ggaggggcaa caacagatg     360
gctggcaact agaaggcaca gtcgaggctg atcagcgagc tctagcattt aggtgacact    420
atagaatagg gccctctagc gaattctcga ctcagttagc ctcccccatc tcccgggcaa    480
acgtgcgcgc caggtcgcat atcgtcggta tggagccggg ggtggtgacg tgggtctgga    540
ccatcccgga ggtaagttgc agcagggcgt cccggcagcc ggcgggcgat tggtcgtaat    600
ccaggataaa gacgtgcatg aacggaggc gtttggccaa gacgtccaag gcccaggcaa     660
acacgttata caggtcgccg ttgggggcca gcaactcggg ggcccgaaac agggtaaata    720
acgtgtcccc gatatggggt cgtgggcccg cgttgctctg gggctcggca ccctggggcg    780
gcacggccgt ccccgaaagc tgtccccagt cctcccgcca cgaccgccg cactgcagat     840
accgcaccgt attggcaagt agcccgtaaa cgcggcgaat cgcagccagc atagccaggt    900
ccagccgctc gccggggcgc tggcgtttgg ccaggcggtc gatgtgtctg tcctccggaa    960
gggccccaag cacgatgttg gtgccgggca aggtcggcgg gatgagggcc acgaacgcca   1020
gcacggcctg gggggtcatg ctgcccataa ggtaccgcgc ggccgggtag cacaggaggg   1080
cggcgatggg atggcggtcg aagatgaggg tgagggccgg gggcggggca tgtgagctcc   1140
cagcctcccc cccgatatga ggagccagaa cggcgtcggt cacggcataa ggcatgccca   1200
ttgttatctg ggcgcttgtc attaccaccg ccgcgtcccc ggccgatatc tcaccctggt   1260
cgaggcggtg ttgtgtggtg tagatgttcg cgattgtctc ggaagccccc agcacccgcc   1320
agtaagtcat cggctcgggt acgtagacga tatcgtcgcg cgaacccagg gccaccagca   1380
gttgcgtggt ggtggttttc cccatcccgt ggggaccgtc tatataaacc cgcagtagcg   1440
tgggcatttt ctgctccggg cggacttccg tggcttcttg ctgccggcga gggcgcaacg   1500
ccgtacgtcg gttgctatgg ccgcgagaac cgcagcctg gtcgaacgca gacgcgactt    1560
ctacacagcc atcggtccag acggccgcgc ttctgcgggc gatttgtgta cgcccgacag   1620
tcccggctcc ggatcggacg attgcgtcgc atcgaccctg cgcccaagct gcatcatcga   1680
aattgccgtc aaccaagctc tgatagagtt ggtcaagacc aatgcggagc atatacgccc   1740
ggagccgcgg cgatcctgca agctccggat gcctccgctc gaagtagcgc gtctgctgct   1800
ccatacaagc caaccacggc ctccagaaga agatgttggc gacctcgtat tgggaatccc   1860
cgaacatcgc ctcgctccag tcaatgaccg ctgttatgcg gccattgtcc gtcaggacat   1920
tgttggagcc gaaatccgcg tgcacgaggt gccggacttc ggggcagtcc tcggcccaaa   1980
gcatcagctc atcgagagcc tgcgcgacgg acgcactgac ggtgtcgtcc atcacagttt   2040
gccagtgata cacatgggga tcagcaatcg cgcatatgaa atcacgccat gtagtgtatt   2100
gaccgattcc ttgcggtccg aatgggccga accgctcgt ctggctaaga tcggccgcag    2160
cgatcgcatc catgagctcc gcgacgggtt gcagaacagc gggcagttcg gtttcaggca   2220
ggtcttgcaa cgtgacaccc tgtgcacggc gggagatgca ataggtcagg ctctcgctga   2280
```

```
attcccccaat gtcaagcact tccggaatcg ggagcgcggc cgatgcaaag tgccgataaa    2340
cataacgatc tttgtagaaa ccatcggcgc agctatttac ccgcaggaca tatccacgcc    2400
ctcctacatc gaagctgaaa gcacgagatt cttcgccctc cgagagctgc atcaggtcgg    2460
agacgctgtc gaacttttcg atcagaaact tcgcgacaga cgtcgcggtg agttcaggct    2520
ttttcatgat ggccctccta ccggtgatct cagctgtagg aaagagaaga aggttagtag    2580
tcgacatggt ggccctccta tagtgagtcg tattatacta tgccgatata ctatgccgat    2640
gattaattgt caacactagg cgccggtcac aactaggtgg gcctatagac tctataggcg    2700
gtacttacgt cactcttggc acggggaatc cgcgttccaa tgcaccgttc ccggccgcgg    2760
aggctggatc ggtcccggtg tcttctatgg aggtcaaaac agcgtggatg gcgtctccag    2820
gcgatctgac ggttcactaa acgagctctg cttatataga cctcccaccg tacacgccta    2880
ccgcccattt cgtcaatggg gcggagttg ttacgacatt ttggaaagtc ccgttgattt    2940
tggtgccaaa acaaactccc attgacgtca atggggtgga gacttggaaa tccccgtgag    3000
tcaaaccgct atccacgccc attgatgtac tgccaaaacc gcatcaccat ggtaatagcg    3060
atgactaata cgtagatgta ctgccaagta ggaaagtccc ataaggtcat gtactgggca    3120
taatgccagg cgggccattt accgtcattg acgtcaatag ggggcgtact ggcatatga    3180 tacacttgat gtactgccaa gtgggcagtt taccgtaaat actccaccca ttgacgtcaa    3240
tggaaagtcc ctattggcgt tactatggga acatacgtca ttattgacgt caatgggcgg    3300
gggtcgttgg gcggtcagcc aggcgggcca tttaccgtaa gttatgtaac ggactctagc    3360
tcgatccagc tcactcccct gttgattgtg tgttatggtg cagagtccag ccactgtttg    3420
tccagtgggg tctctgacct gccttcctgt agctcttgga gtcattctgg cctccccctc    3480
ccccaagccc acacaaaaaa ccaacacaca gatccaatga aaataatgat tgtttattgc    3540
agcttaatta actagccatg accaaaatcc cttaacgtga gttttcgttc cactgagcgt    3600
cagaccccgt agaaaagatc aaaggatctt cttgagatcc ttttttttctg cgcgtaatct    3660 gctgcttgca acaaaaaaa ccaccgctac cagcggtggt ttgtttgccg gatcaagagc    3720
taccaactct ttttccgaag gtaactggct tcagcagagc gcagatacca aatactgttc    3780
ttctagtgta gccgtagtta ggccaccact tcaagaactc tgtagcaccg cctacatacc    3840
tcgctctgct aatcctgtta ccagtggctg ctgccagtgg cgataagtcg tgtcttaccg    3900
ggttggactc aagacgatag ttaccggata aggcgcagcg gtcgggctga acggggggtt    3960
cgtgcacaca gcccagcttg gagcgaacga cctacaccga actgagatac ctacagcgtg    4020
agcattgaga aagcgccacg cttcccgaag ggagaaaggc ggacaggtat ccggtaagcg    4080
gcagggtcgg aacaggagag cgcacgaggg agcttccagg gggaaacgcc tggtatcttt    4140
atagtcctgt cgggtttcgc cacctctgac ttgagcgtcg attttttgtga tgctcgtcag    4200 gggggcggag cctatggaaa aacgccagca acgcggcctt tttacggttc ctggccttt    4260 gctggccttt tgctcacatg ttcttcgcta acatttaaat ggatctacca catttgtaga    4320
ggttttactt gctttaaaaa acctcccaca cctccccctg aacctgaaac ataaaatgaa    4380
tgcaattgtt gttgttaact tgtttattgc agcttataat ggttacaaat aaagcaatag    4440
catcacaaat ttcacaaata aagcaatagc atcacaaatt tcacaaataa agcatttttt    4500
tcactgcatt ctagttgtgg tttgtccaaa ctcatcaatg tatcttatca tgtcgagcta    4560
gctgtacaat cgatagatct aggcctcctt cgccggccgc tcagcgaggg ggcagggcct    4620
```

-continued

```
gcatgtgaag ggcgtcgtag gtgtccttgg tggctgtact gagaccctgg taaaggccat    4680 cgtgccccet tgcccctccgg cgctcgcctt tcatcccaat ctcactgtag gcctccgcca    4740
tcttatcttt ctgcagttca ttgtacaggc cttcctgagg gttcttcctt ctcggctttc    4800
cccccatctc agggtcccgg ccacgtctct tgtccaaaac atcgtactcc tctcttcgtc    4860
ctagattgag ctcgttatag agctggttct ggccctgctg gtacgcgggg gcgtctgcgc    4920
tcctgctgaa cttcactctg aagaagatgc ctagcccaat gaaaagcagg aggccggcga    4980
cgccccccag cacaatcagg gccatttttac ctagggacag ggagaggctc ttctgtgtgt    5040
agtggttgtg cagagcctca tgcatcacgg agcatgagaa acattcccc tcctgccacc    5100 tgctcttgtc cacggttagc ctgctgtaga ggaagaagga gccgtcggag tccagcacgg    5160
gaggcgtggt cttgtagttg ttctccggct gcccattgct ctcccactcc acggcgatgt    5220 cgctgggta aagccttttg accaggcagg tcaggctgac ctggttcttg gtcatctcct    5280
cctgggatgg gggcagggtg tacacctgtg gctctcgggg ctgcccttttg gctttggaga    5340 tggttttctc gatggaggac gggaggcctt tgttggagac cttgcacttg tactccttgc    5400
cgttcagcca gtcctggtgc aggacggtga ggacgctgac cacacggtac gtgctgttga    5460
actgctcctc ccgcggcttt gtcttggcat tatgcacctc cacgccatcc acgtaccagt    5520
tgaactggac ctcggggtct tcctggctca cgtccaccac cacgcacgtg acctcagggg    5580
tccgggagat catgagagtg tccttgggtt ttgggggaa caggaagact gatggtcccc    5640
ccaggaactc aggtgctggg catggtgggc atggggacc atatttggac tcgttgaacc    5700
gtccctcgcg aaaaagtttc tttaaatgta agagcaggtc ctttacaaac tgggccacct    5760
cgattttggt gtctcggaca tgcaagctgg aaaactgccc agctgagacc ttgtgcgggc    5820
agaatccgct cagcatcctc tgggtcttct cgatggcact gcagcctgac acgttgatca    5880
gggattccag ggctgcacag tacatgccag ctgtcaggtt gatgctccat accatgctgc    5940
cattgcagag cggagccttc tggttctggg tgatgttgac cagctcctca atgaggtacc    6000
tgagggctgt agagggaggc acagggcctg ggatcaggag gaatgctggg tgtggtaact    6060
cacagagcag aaggcttgtc accaggagaa gcatggtggc ggctctaggg tgatctcagc    6120
tgtaggaaag agaagaaggt tagtagtcga cgtgtccctc tcgatgaatc cgtatcaatt    6180
gtgagcgctc acaagtcaac actcttttttg ataaatctag tagatatcac ttacgtaggc    6240
gccggtcaca gcttggatct gtaacggcgc agaacagaaa acgaaacaaa gacgtagagt    6300
tgagcaagca gggtcaggca aagcgtggag agccggctga gtctaggtag gctccaaggg    6360
agcgccggac aaaggcccgg tctcgacctg agctttaaac ttacctagac ggcggacgca    6420
gttcaggagg caccacaggc gggaggcggc agaacgcgac tcaacggcg tggatggcgg    6480 cctcaggtag ggcggcgggc gcgtgaagga gagatgcgag ccctcgaag cttcagctgt    6540 gttctggcgg caaacccgtt gcgaaaaaga acgttcacgg cgactactgc acttatatac    6600
ggttctcccc cacccctcggg aaaaaggcgg agccagtaca cgacatcact ttcccagttt    6660
accccgcgcc accttctcta ggcaccggtt caattgccga cccctccccc caacttctcg    6720 ggactgtgg gcgatgtgcg ctctgcccac tgacgggcac cggagcgatc gcagatcctt    6780
cga                                                                 6783
```

<210> SEQ ID NO 17
<211> LENGTH: 497
<212> TYPE: PRT
<213> ORGANISM: Homo sapiens

<400> SEQUENCE: 17

```
Met Leu Leu Leu Val Thr Ser Leu Leu Leu Cys Glu Leu Pro His Pro
1               5                   10                  15

Ala Phe Leu Leu Ile Pro Gly Pro Val Pro Pro Ser Thr Ala Leu Arg
            20                  25                  30

Tyr Leu Ile Glu Glu Leu Val Asn Ile Thr Gln Asn Gln Lys Ala Pro
            35                  40                  45

Leu Cys Asn Gly Ser Met Val Trp Ser Ile Asn Leu Thr Ala Gly Met
    50                  55                  60

Tyr Cys Ala Ala Leu Glu Ser Leu Ile Asn Val Ser Gly Cys Ser Ala
65                  70                  75                  80

Ile Glu Lys Thr Gln Arg Met Leu Ser Gly Phe Cys Pro His Lys Val
                85                  90                  95

Ser Ala Gly Gln Phe Ser Ser Leu His Val Arg Asp Thr Lys Ile Glu
            100                 105                 110

Val Ala Gln Phe Val Lys Asp Leu Leu Leu His Leu Lys Lys Leu Phe
            115                 120                 125

Arg Glu Gly Arg Phe Asn Glu Ser Lys Tyr Gly Pro Pro Cys Pro Pro
            130                 135                 140

Cys Pro Ala Pro Glu Phe Leu Gly Gly Pro Ser Val Phe Leu Phe Pro
145                 150                 155                 160

Pro Lys Pro Lys Asp Thr Leu Met Ile Ser Arg Thr Pro Glu Val Thr
                165                 170                 175

Cys Val Val Val Asp Val Ser Gln Glu Asp Pro Glu Val Gln Phe Asn
            180                 185                 190

Trp Tyr Val Asp Gly Val Glu Val His Asn Ala Lys Thr Lys Pro Arg
            195                 200                 205

Glu Glu Gln Phe Asn Ser Thr Tyr Arg Val Val Ser Val Leu Thr Val
            210                 215                 220

Leu His Gln Asp Trp Leu Asn Gly Lys Glu Tyr Lys Cys Lys Val Ser
225                 230                 235                 240

Asn Lys Gly Leu Pro Ser Ser Ile Glu Lys Thr Ile Ser Lys Ala Lys
                245                 250                 255

Gly Gln Pro Arg Glu Pro Gln Val Tyr Thr Leu Pro Pro Ser Gln Glu
            260                 265                 270

Glu Met Thr Lys Asn Gln Val Ser Leu Thr Cys Leu Val Lys Gly Phe
            275                 280                 285

Tyr Pro Ser Asp Ile Ala Val Glu Trp Glu Ser Asn Gly Gln Pro Glu
            290                 295                 300

Asn Asn Tyr Lys Thr Thr Pro Pro Val Leu Asp Ser Asp Gly Ser Phe
305                 310                 315                 320

Phe Leu Tyr Ser Arg Leu Thr Val Asp Lys Ser Arg Trp Gln Glu Gly
                325                 330                 335

Asn Val Phe Ser Cys Ser Val Met His Glu Ala Leu His Asn His Tyr
            340                 345                 350

Thr Gln Lys Ser Leu Ser Leu Ser Leu Gly Lys Met Ala Leu Ile Val
            355                 360                 365

Leu Gly Gly Val Ala Gly Leu Leu Leu Phe Ile Gly Leu Gly Ile Phe
            370                 375                 380

Phe Arg Val Lys Phe Ser Arg Ser Ala Asp Ala Pro Ala Tyr Gln Gln
385                 390                 395                 400
```

```
Gly Gln Asn Gln Leu Tyr Asn Glu Leu Asn Leu Gly Arg Arg Glu Glu
                405                 410                 415

Tyr Asp Val Leu Asp Lys Arg Arg Gly Arg Asp Pro Glu Met Gly Gly
            420                 425                 430

Lys Pro Arg Arg Lys Asn Pro Gln Glu Gly Leu Tyr Asn Glu Leu Gln
            435                 440                 445

Lys Asp Lys Met Ala Glu Ala Tyr Ser Glu Ile Gly Met Lys Gly Glu
        450                 455                 460

Arg Arg Arg Gly Lys Gly His Asp Gly Leu Tyr Gln Gly Leu Ser Thr
465                 470                 475                 480

Ala Thr Lys Asp Thr Tyr Asp Ala Leu His Met Gln Ala Leu Pro Pro
                485                 490                 495

Arg

<210> SEQ ID NO 18
<211> LENGTH: 691
<212> TYPE: PRT
<213> ORGANISM: Artificial Sequence
<220> FEATURE:
<223> OTHER INFORMATION: selection/ suicide fusion coding region
      containing herpes simplex virus and E.coli sequences

<400> SEQUENCE: 18

Met Lys Lys Pro Glu Leu Thr Ala Thr Ser Val Ala Lys Phe Leu Ile
1               5                   10                  15

Glu Lys Phe Asp Ser Val Ser Asp Leu Met Gln Leu Ser Glu Gly Glu
            20                  25                  30

Glu Ser Arg Ala Phe Ser Phe Asp Val Gly Gly Arg Gly Tyr Val Leu
        35                  40                  45

Arg Val Asn Ser Cys Ala Asp Gly Phe Tyr Lys Asp Arg Tyr Val Tyr
    50                  55                  60

Arg His Phe Ala Ser Ala Ala Leu Pro Ile Pro Glu Val Leu Asp Ile
65                  70                  75                  80

Gly Glu Phe Ser Glu Ser Leu Thr Tyr Cys Ile Ser Arg Arg Ala Gln
                85                  90                  95

Gly Val Thr Leu Gln Asp Leu Pro Glu Thr Glu Leu Pro Ala Val Leu
            100                 105                 110

Gln Pro Val Ala Glu Leu Met Asp Ala Ile Ala Ala Ala Asp Leu Ser
        115                 120                 125

Gln Thr Ser Gly Phe Gly Pro Phe Gly Pro Gln Gly Ile Gly Gln Tyr
    130                 135                 140

Thr Thr Trp Arg Asp Phe Ile Cys Ala Ile Ala Asp Pro His Val Tyr
145                 150                 155                 160

His Trp Gln Thr Val Met Asp Asp Thr Val Ser Ala Ser Val Ala Gln
                165                 170                 175

Ala Leu Asp Glu Leu Met Leu Trp Ala Glu Asp Cys Pro Glu Val Arg
            180                 185                 190

His Leu Val His Ala Asp Phe Gly Ser Asn Asn Val Leu Thr Asp Asn
        195                 200                 205

Gly Arg Ile Thr Ala Val Ile Asp Trp Ser Glu Ala Met Phe Gly Asp
    210                 215                 220

Ser Gln Tyr Glu Val Ala Asn Ile Phe Phe Trp Arg Pro Trp Leu Ala
225                 230                 235                 240

Cys Met Glu Gln Gln Thr Arg Tyr Phe Glu Arg Arg His Pro Glu Leu
                245                 250                 255
```

```
Ala Gly Ser Pro Arg Leu Arg Ala Tyr Met Leu Arg Ile Gly Leu Asp
        260                 265                 270

Gln Leu Tyr Gln Ser Leu Val Asp Gly Asn Phe Asp Ala Ala Trp
        275                 280                 285

Ala Gln Gly Arg Cys Asp Ala Ile Val Arg Ser Gly Ala Gly Thr Val
        290                 295                 300

Gly Arg Thr Gln Ile Ala Arg Arg Ser Ala Ala Val Trp Thr Asp Gly
305                 310                 315                 320

Cys Val Glu Val Ala Ser Ala Phe Asp Gln Ala Ala Arg Ser Arg Gly
                325                 330                 335

His Ser Asn Arg Arg Thr Ala Leu Arg Pro Arg Gln Gln Glu Ala
                340                 345                 350

Thr Glu Val Arg Pro Glu Gln Lys Met Pro Thr Leu Leu Arg Val Tyr
                355                 360                 365

Ile Asp Gly Pro His Gly Met Gly Lys Thr Thr Thr Gln Leu Leu
        370                 375                 380

Val Ala Leu Gly Ser Arg Asp Asp Ile Val Tyr Val Pro Glu Pro Met
385                 390                 395                 400

Thr Tyr Trp Arg Val Leu Gly Ala Ser Glu Thr Ile Ala Asn Ile Tyr
                405                 410                 415

Thr Thr Gln His Arg Leu Asp Gln Gly Glu Ile Ser Ala Gly Asp Ala
                420                 425                 430

Ala Val Val Met Thr Ser Ala Gln Ile Thr Met Gly Met Pro Tyr Ala
                435                 440                 445

Val Thr Asp Ala Val Leu Ala Pro His Ile Gly Gly Glu Ala Gly Ser
        450                 455                 460

Ser His Ala Pro Pro Ala Leu Thr Leu Ile Phe Asp Arg His Pro
465                 470                 475                 480

Ile Ala Ala Leu Leu Cys Tyr Pro Ala Ala Arg Tyr Leu Met Gly Ser
                485                 490                 495

Met Thr Pro Gln Ala Val Leu Ala Phe Val Ala Leu Ile Pro Pro Thr
                500                 505                 510

Leu Pro Gly Thr Asn Ile Val Leu Gly Ala Leu Pro Glu Asp Arg His
                515                 520                 525

Ile Asp Arg Leu Ala Lys Arg Gln Arg Pro Gly Glu Arg Leu Asp Leu
        530                 535                 540

Ala Met Leu Ala Ala Ile Arg Arg Val Tyr Gly Leu Leu Ala Asn Thr
545                 550                 555                 560

Val Arg Tyr Leu Gln Cys Gly Gly Ser Trp Arg Glu Asp Trp Gly Gln
                565                 570                 575

Leu Ser Gly Thr Ala Val Pro Pro Gln Gly Ala Glu Pro Gln Ser Asn
                580                 585                 590

Ala Gly Pro Arg Pro His Ile Gly Asp Thr Leu Phe Thr Leu Phe Arg
                595                 600                 605

Ala Pro Glu Leu Leu Ala Pro Asn Gly Asp Leu Tyr Asn Val Phe Ala
        610                 615                 620

Trp Ala Leu Asp Val Leu Ala Lys Arg Leu Arg Ser Met His Val Phe
625                 630                 635                 640

Ile Leu Asp Tyr Asp Gln Ser Pro Ala Gly Cys Arg Asp Ala Leu Leu
                645                 650                 655

Gln Leu Thr Ser Gly Met Val Gln Thr His Val Thr Thr Pro Gly Ser
                660                 665                 670
```

```
-continued

Ile Pro Thr Ile Cys Asp Leu Ala Arg Thr Phe Ala Arg Glu Met Gly
        675                 680                 685

Glu Ala Asn
    690
```

CHIMERIC IMMUNORECEPTOR USEFUL IN TREATING HUMAN GLIOMAS

This application is a continuation-in-part of U.S. application Ser. No. 10/134,645, filed Apr. 30, 2002, now abandoned, which claims the benefit of U.S. Provisional application Ser. No. 60/286,981, filed Apr. 30, 2001.

TECHNICAL FIELD

This invention relates to cancer therapy, and the use of genetically-modified T-lymphocytes expressing chimeric immunoreceptors in the treatment of human brain tumors and other cancers.

BACKGROUND OF THE INVENTION

Primary brain tumors are the third leading contributor to cancer-related mortality in young adults, are the second leading contributor in children, and appear to be increasing in incidence both in the pediatric and geriatric population[1-4]. Gliomas are the most common type of primary brain tumors; 20,000 cases are diagnosed and 14,000 glioma-related deaths occur annually in the United States[5-8]. Gliomas are heterogeneous with respect to their malignant behavior and, in their most common and aggressive forms, anaplastic astrocytoma (AA-grade III) and glioblastoma multiforme (GBM-grade IV), are rapidly progressive and nearly uniformly lethal[9; 10]. Currently available therapeutic modalities have minimal curative potential for these high-grade tumors and often exacerbate the already severe morbidities imposed by their location in the central nervous system. Thus patients with malignant glioma are often struck in the most productive period of their lives; frequent deterioration of mental faculties and a high case:fatality ratio contribute to the unique personal and social impact of these tumors.

The cornerstones of oncologic management of malignant glioma are resection and radiation therapy[11-16]. With modern surgical and radiotherapeutic techniques the mean duration of survival has increased to 82 weeks for glioblastoma multiforme and 275 weeks for anaplastic astrocytoma, although 5-year survival rates have only increased from 3 to 6% for glioblastoma multiforme and 12.1% for anaplastic astrocytoma[6-8]. The major prognostic indicators for prolonged survival are younger age (<40 yrs) and performance status (KPS score >70)[17]. Resections of >90% of bulky tumors are usually attempted provided that vital functional anatomy is spared. When used in conjunction with post-operative radiation therapy, the impact of extent of resection on duration of survival is less clear[18; 19]. The addition of chemotherapy to resection and radiation provides only marginal survival advantage to patients with anaplastic astrocytoma or glioblastoma multiforme[20-23]. Nitrosureas alone or in combination with procarbazine and vincristine are the conventional drugs used in the community and appear to improve the 1-year and 2-year survival rates by 15% without impacting on the overall median survival[24; 25]. More aggressive regimens incorporating platinum-based drugs and topoisomerase inhibitors are under investigation[26]. The role of high-dose chemotherapy with stem cell rescue has not been substantiated to date[27-29].

Approximately 80% of recurrent tumors arise from radiographically enhancing remnants of the original incompletely resected tumor[10; 30; 31]. Provided recurrences are unifocal and amenable in their location to aggressive re-resection, this approach can extend survival duration, particularly for patients with anaplastic astrocytoma and those glioblastoma multiforme patients with a KPS >70.[10] The median survival of recurrent glioblastoma multiforme patients treated with re-resection is 36 weeks[10; 30; 31]. Radiation therapy in the form of either brachytherapy or stereotactic radiosurgery may extend the duration of survival in re-resected recurrent glioblastoma multiforme patients by only 10-12 weeks[32]. The use of chemotherapy in the setting of recurrent disease should be in the context of available clinical trials, as its efficacy in this patient population is unsubstantiated.

The continued dismal prognosis of malignant glioma has prompted the clinical investigation of novel therapeutic entities, including, but not limited to: gene therapy (TK-suicide, antisense inhibition of tumor growth factor receptors, conditionally lethal viral vectors), immunotherapy (antibody, tumor cell vaccines, immunotoxins, adoptive transfer of activated lymphocytes), and anti-angiogenesis approaches[33-40]. The multiplicity of challenges faced in the development of effective adjuvant therapies for malignant glioma include the extensive infiltrative growth of tumor cells into normal brain parenchyma, the capacity of soluble factors elaborated from these tumors to attenuate the development of immune responses, and the difficulty of establishing clinically meaningful therapeutic ratios when administering therapeutics into the central nervous system (CNS). Early clinical evaluation of novel therapeutics is clearly indicated in this patient population.

Recently, receptors for transferrin and growth factors have been the subject of experimental glioma therapeutics utilizing ligands for these receptors conjugated to toxins or radionucleotides as a delivery system[41]. The specificity of this approach relies on the unique expression or over-expression of targeted receptors on glioma cells compared to normal brain. Interestingly, some receptor complexes for interleukins utilized by the immune system are expressed by gliomas, in particular high-affinity IL-13 receptors[42-48]. Unlike the IL-13 receptor trimolecular complex utilized by the immune system, which consists of the IL-13Rα1, the IL-4Rβ, and γc, glioma cells overexpress a unique IL-13Rα2 chain capable of binding IL-13 independently of the requirement for IL-4Rβ or γc[44; 49; 50]. Like its homologue IL-4, IL-13 has pleotrophic immunoregulatory activity outside the CNS[51-53]. Both cytokines stimulate IgE production by B lymphocytes and suppress pro-inflammatory cytokine production by macrophages. The immunobiology of IL-13 within the CNS is largely unknown.

Detailed studies by Debinski et al. using autoradiography with radiolabeled IL-13 have demonstrated abundant IL-13 binding on nearly all malignant glioma tissues studied[42; 45; 46; 48]. Moreover, the binding is highly homogeneous within tumor sections and from single cell analysis[46; 48]. Scatchard analyses of IL-13 binding to human glioma cell lines reveals on average 17,000-28,000 binding sites/cell[45]. Molecular analysis using probes specific for IL-13Rα2 mRNA fail to demonstrate expression of the glioma-specific receptor by normal brain elements in all CNS anatomic locations[42; 43]. Furthermore, autoradiography with radiolabeled IL-13 failed to demonstrate detectable specific IL-13 binding in the CNS, suggesting that the shared IL13Rα1/IL-4β/γc receptor is also not expressed at detectable levels in the CNS[46]. These findings were independently verified using immunohistochemical techniques on non-pathologic brain sections with antibodies specific for IL-13Rα1 and IL-4β[54]. Thus IL-13Rα2 stands as the most specific and ubiquitously expressed cell-surface target for glioma described to date.

As a strategy to exploit the glioma-specific expression of IL-13Rα2 in the CNS, molecular constructs of the IL-13 cytokine have been described that fuse various cytotoxins (*Pseudomonas* exotoxin and *Diptheria* toxin) to its carboxyl terminal[55-58]. Internalization of these toxins upon binding to IL-13 receptors is the basis of the selective toxicity of these fusion proteins. These toxins display potent cytotoxicity towards glioma cells in vitro at picomolar concentrations[55]. Human intracranial glioma xenografts in immunodeficient mice can be eliminated by intratumor injection of the IL-13-toxin fusion protein without observed toxicities[55]. These studies support the initiation of clinical investigation utilizing IL-13-directed immunotoxins loco-regionally for malignant glioma However, the binding of IL-13-based cytotoxins to the broadly expressed IL-13Rα1/IL-4β/γc receptor complex has the potential of mediating untoward toxicities to normal tissues outside the CNS, and thus limits the systemic administration of these agents. IL-13 has been extensively dissected at the molecular level: structural domains of this cytokine that are important for associating with individual receptor subunits have been mapped[55; 58]. Consequently, selected amino acid substitutions in IL-13 have predictable effects on the association of this cytokine with its receptor subunits. Amino acid substitutions in IL-13's alpha helix A, in particular at amino acid 13, disrupt its ability to associate with IL-4β, thereby selectively reducing the affinity of IL-13 to the IL-13Rα1/IL-4β/γc receptor by a factor of five[55; 57; 58] Surprisingly, binding of mutant IL-13(E13Y) to IL-13Rα2 was not only preserved but increased relative to wild-type IL-13 by 50-fold. Thus, minimally altered IL-13 analogs can simultaneously increase IL-13's specificity and affinity for glioma cells via selective binding to IL-13Rα2 relative to normal tissues bearing IL-13Rα1/IL-4β/γc receptors.

Malignant gliomas represent a clinical entity that is highly attractive for immunotherapeutic intervention since 1) most patients with resection and radiation therapy achieve a state of minimal disease burden and 2) the anatomic location of these tumors within the confines of the CNS make direct loco-regional administration of effector cells possible. At least two pathologic studies have demonstrated that the extent of perivascular lymphocytic infiltration in malignant gliomas correlates with an improved prognosis[59-61]. Animal model systems have established that glioma-specific T cells, but not lymphokine-activated killer (LAK) cells, can mediate the regression of intracerebrally implanted gliomas[62-71]. T cells, unlike LAK cells, have the capacity to infiltrate into brain parenchyma and thus can target infiltrating tumor cells that may be distant from the primary tumor. Despite these findings, there is a substantial body of evidence that gliomas actively subvert immune destruction, primarily by the elaboration of immunosuppressive cytokines (TGF-β2) and prostaglandins, which, inhibit the induction/amplification of glioma-reactive T cell responses[72-74]. These findings have prompted the evaluation of ex vivo expanded anti-glioma effector cells for adoptive therapy as a strategy to overcome tumor-mediated limitations of generating responses in vivo.

At least ten pilot studies involving the administration of ex vivo activated lymphocytes to malignant glioma resection cavities have been reported to date[75-85]. Despite the variety of effector cell types (LAK, TILs, alloreactive CTLs), their heterogeneous composition/variability of composition from patient to patient, and the often modest in vitro reactivity of these effector cells towards glioma targets, these studies, in aggregate, report an approximate 50% response rate in patients with recurrent/refractory disease with anecdotal long-term survivors. These studies support the premise that a superior clinical effect of cellular immunotherapy for glioma might be expected with homogenous highly potent effector cells.

These pilot studies also report on the safety and tolerability of direct administration of ex vivo activated lymphocytes and interleukin-2 (IL-2), a T cell growth factor, into the resection cavity of patients with malignant glioma[75; 76; 78; 82; 86-92]. Even at large individual cell doses ($>10^9$ cells/dose), as well as high cumulative cell doses ($>27\times10^9$ cells), toxicities are modest, and typically consist of grade II or less transient headache, nausea, vomiting and fever. As noted above, these studies also employed the co-administration of rhIL-2 to support the in vivo survival of transferred lymphocytes. Multiple doses given either concurrently with lymphocytes or sequentially after lymphocyte administration were tolerated at doses as high as $1.2\times10^6$ IU/dose for 12-dose courses of IL-2 delivered every 48-hours.

Based on the findings outlined above, strategies to improve the anti-tumor potency of lymphocyte effector cells used in glioma immunotherapy are under development. One approach utilizes bi-specific antibodies capable of co-localizing and activating T lymphocytes via an anti-CD3 domain with glioma targets utilizing an epidermal growth factor receptor (EGFR) binding domain[93-96]. Preliminary clinical experience with this bi-specific antibody in combination with autologous lymphocytes suggests that T cells are activated in situ in the resection cavity. Targeting infiltrating tumor cells within the brain parenchyma, however, is a potentially significant limitation of this approach. T cells might have significantly increased anti-glioma activity if they are specific for target antigens expressed by gliomas. A growing number of human genes encoding tumor antigens to which T lymphocytes are reactive have been cloned, including the SART-1 gene, which appears to be expressed by nearly 75% of high-grade gliomas[97]. Both dendritic cell-based in vitro cell culture techniques, as well as tetramer-based T cell selection technologies are making feasible the isolation of antigen-specific T cells for adoptive therapy. Since antigens like SART-1 are recognized by T cells in the context of restricting HLA alleles, antigen-specific approaches will require substantial expansion in the number of antigens and restricting HLA alleles capable of presenting these antigens to be broadly applicable to the general population of glioma patients.

Chimeric antigen receptors engineered to consist of an extracellular single chain antibody (scFvFc) fused to the intracellular signaling domain of the T cell antigen receptor complex zeta chain (scFvFc:ζ) have the ability, when expressed in T cells, to redirect antigen recognition based on the monoclonal antibody's specificity[98]. The design of scFvFc:ζ receptors with target specificities for tumor cell-surface epitopes is a conceptually attractive strategy to generate antitumor immune effector cells for adoptive therapy as it does not rely on pre-existing anti-tumor immunity. These receptors are "universal" in that they bind antigen in a MHC independent fashion, thus, one receptor construct can be used to treat a population of patients with antigen-positive tumors. Several constructs for targeting human tumors have been described in the literature including receptors with specificities for Her2/Neu, CEA, ERRB-2, CD44v6, and epitopes selectively expressed on renal cell carcinoma[98-104]. These epitopes all share the common characteristic of being cell-surface moieties accessible to scFv binding by the chimeric T cell receptor. In vitro studies have demonstrated that both CD4+ and CD8+ T cell effector functions can be triggered via these receptors. Moreover, animal models have demonstrated the capacity of adoptively transferred scFvFc:ζ expressing T cells to eradicate established tumors[105]. The function of primary human T cells expressing tumor-specific scFvFc:ζ receptors have been evaluated in vitro; these cells specifically lyse tumor targets and secrete an array of pro-inflammatory cytokines including IL-2, TNF, IFN-γ, and GM-CSF[104].

Phase I pilot adoptive therapy studies are underway utilizing autologous scFvFc:ζ-expressing T cells specific for HIV gp120 in HIV infected individuals and autologous scFvFc:ζ-expressing T cells with specificity for TAG-72 expressed on a variety of adenocarcinomas, including breast and colorectal adenocarcinoma.

Investigators at City of Hope have engineered a CD20-specific scFvFc:ζ receptor construct for the purpose of targeting CD20+ B-cell malignancy and an L1-CAM-specific chimeric immunoreceptor for targeting neuroblastoma[106]. Preclinical laboratory studies have demonstrated the feasibility of isolating and expanding from healthy individuals and lymphoma patients CD8+ CTL clones that contain a single copy of unrearranged chromosomally integrated vector DNA and express the CD20-specific scFvFc:ζ receptor[107]. To accomplish this, purified linear plasmid DNA containing the chimeric receptor sequence under the transcriptional control of the CMV immediate/early promoter and the NeoR gene under the transcriptional control of the SV40 early promoter was introduced into activated human peripheral blood mononuclear cells by exposure of cells and DNA to a brief electrical current, a procedure called electroporation. Utilizing selection, cloning, and expansion methods currently employed in FDA-approved clinical trials at the Fred Hutchinson Cancer Research Center, Seattle, Wash., gene modified CD8+ CTL clones with CD20-specific cytolytic activity have been generated from each of six healthy volunteers in 15 separate electroporation procedures. These clones when co-cultured with a panel of human CD20+ lymphoma cell lines proliferate, specifically lyse target cells, and are stimulated to produce cytokines.

SUMMARY OF THE INVENTION

The present invention relates to chimeric transmembrane immunoreceptors, named "zetakines," comprised of an extracellular domain comprising a soluble receptor ligand linked to a support region capable of tethering the extracellular domain to a cell surface, a transmembrane region and an intracellular signaling domain. Zetakines, when expressed on the surface of T lymphocytes, direct T cell activity to those cells expressing a receptor for which the soluble receptor ligand is specific. Zetakine chimeric immunoreceptors represent a novel extension of antibody-based immunoreceptors for redirecting the antigen specificity of T cells, with application to treatment of a variety of cancers, particularly via the autocrine/paracrine cytokine systems utilized by human malignancy.

In one preferred embodiment exploiting the tumor-restricted expression of IL-13Rα2 by malignant glioma and renal cell carcinoma as a target for cellular immunotherapy, a mutant of the IL-13 cytokine, IL-13 (E13Y), having selective high-affinity binding to IL-13 Rα2 has been converted into a type I transmembrane chimeric immunoreceptor capable of redirecting T cell antigen specificity to IL-13Rα2-expressing tumor cells. This embodiment of the zetakine consists of extracellular IL-13(E13Y) fused to human IgG4 Fc, transmembrane CD4, and intracellular T cell antigen receptor CD3 complex zeta chain. Analogous immunoreceptors can be created that are specific to any of a variety of cancer cell types that selectively express receptors on their cell surfaces, for which selective ligands are known or can be engineered.

Bulk lines and clones of human T cells stably transformed to express such an immunoreceptor display redirected cytolysis of the cancer cell type to which they are specific, while showing negligible toxicity towards non-target cells. Such engineered T cells are a potent and selective therapy for malignancies, including difficult to treat cancers such as glioma.

BRIEF DESCRIPTION OF THE FIGURES

FIG. 2: Results of flow cytometric analysis showing that expressed IL13zetakine chimeric immunoreceptor trafficks to the cell-surface as a type I transmembrane protein.

FIG. 4 A shows that the IL13zetakine+ CTL clone acquired glioma-specific re-directed cytolytic activity.

FIG. 7: Results of growth studies.

FIG. 10: Nucleic acid sequence of the plasmid DNA vector (upper strand: SEQ ID NO:14; lower strand:SEQ ID NO:16) and the corresponding amino acid sequence of IL13zetakine (SEQ ID NO:17) and HyTK (SEQ ID NO:18).

DETAILED DESCRIPTION

Figure 1:
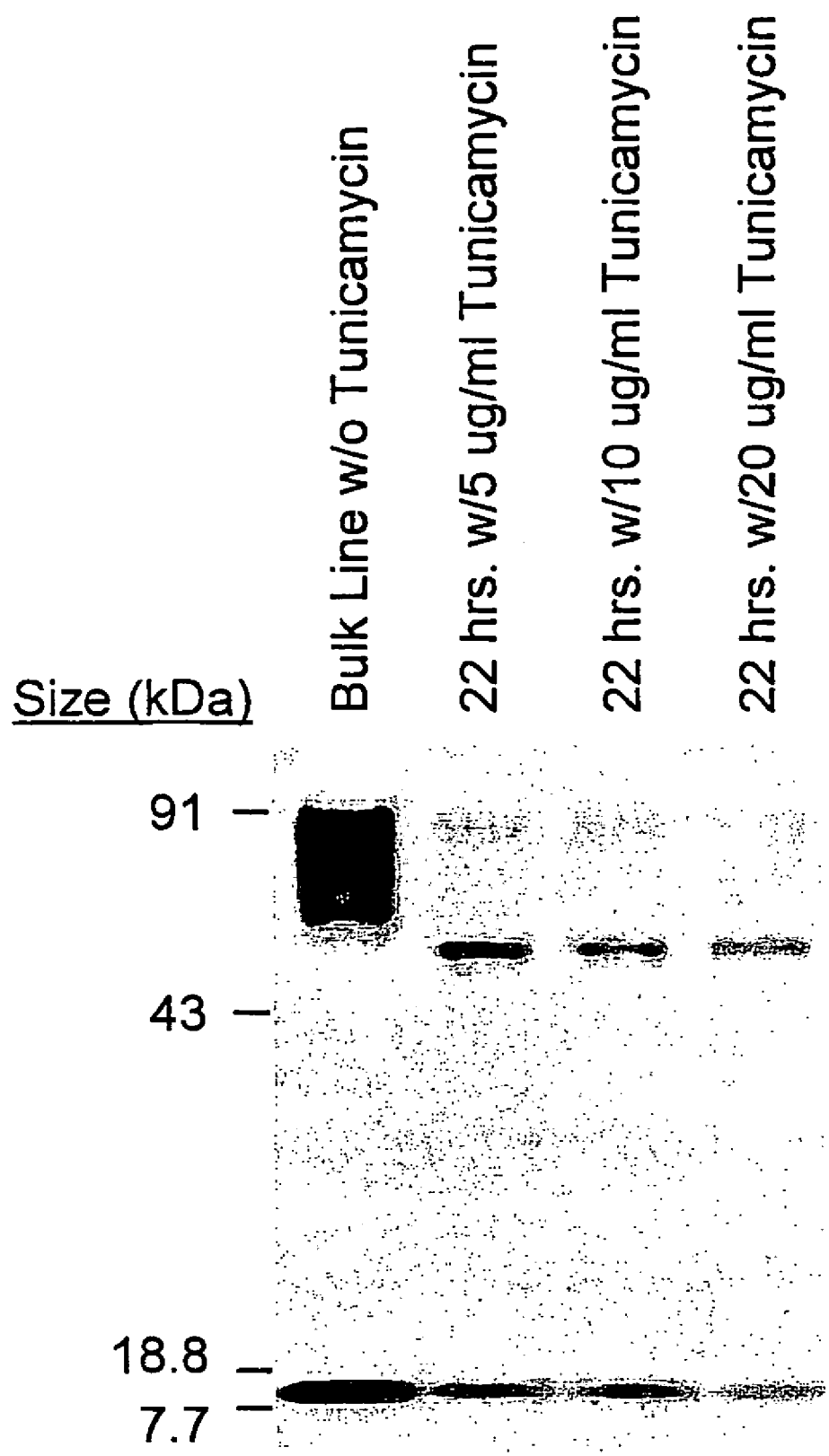
FIG. 1: Results of a Western Blot showing that the IL13zetakine Chimeric Immunoreceptor is expressed as an intact glycosylated protein in Jurkat T cells.

An ideal cell-surface epitope for tumor targeting with genetically-engineered re-directed T cells would be expressed solely on tumor cells in a homogeneous fashion and on all tumors within a population of patients with the same diagnosis. Modulation and/or shedding of the target molecule from the tumor cell membrane may also impact on the utility of a particular target epitope for re-directed T cell recognition. To date few "ideal" tumor-specific epitopes have been defined and secondary epitopes have been targeted based on either lack of expression on critical normal tissues or relative over-expression on tumors. In the case of malignant glioma, the intracavitary administration of T cells for the treatment of this cancer permits the expansion of target epitopes to those expressed on tumor cells but not normal CNS with less stringency on expression by other tissues outside the CNS. The concern regarding toxicity from cross-reactivity of tissues outside the CNS is mitigated by a) the sequestration of cells in the CNS based on the intracavitary route of administration and b) the low cell numbers administered in comparison to cell doses typically administered systemically.

The IL-13Rα2 receptor stands out as the most ubiquitous and specific cell-surface target for malignant glioma[47]. Sensitive autoradiographic and immunohistochemical studies fail to detect IL-13 receptors in the CNS[46; 48]. Moreover, mutation of the IL-13 cytokine to selectively bind the glioma-restricted IL-13Rα2 receptor is a further safeguard against untoward reactivity of IL-13-directed therapeutics against IL-13Rα1/IL-4β+ normal tissues outside the CNS[55; 57]. The potential utility of targeting glioma IL-13Rα2 the design and testing of a novel engineered chimeric immunoreceptor for re-directing the specificity of T cells that consists of an extracellular IL-13 mutant cytokine (E13Y) tethered to the plasma membrane by human IgG4 Fc which, in turn, is fused to CD4TM and the cytoplasmic tail of CD3 zeta. This chimeric immunoreceptor has been given the designation of "IL-13 zetakine." The IL-13Rα2 receptor/IL-13(E13Y) receptor-ligand pair is an excellent guide for understanding and assessing the suitability of receptor-ligand pairs generally for use in zetakines. An ideal zetakine comprises an extracellular soluble receptor ligand having the properties of IL-13(E13Y) (specificity for a unique cancer cell surface receptor, in vivo stability due to it being derived from a naturally-occurring soluble cell signal molecule, low immunogenicity for the same reason). The use of soluble receptor ligands as distinct advantages over the prior art use of antibody fragments (such as the scFvFc immunoreceptors) or cell adhesion molecules, in that soluble receptor ligands are more likely to be stable in the extracellular environment, non-antigenic, and more selective.

Chimeric immunoreceptors according to the present invention comprise an extracellular domain comprised of a soluble receptor ligand linked to an extracellular support region that tethers the ligand to the cell surface via a transmembrane domain, in turn linked to an intracellular receptor signaling domain. Examples of suitable soluble receptor ligands include autocrine and paracrine growth factors, chemokines, cytokines, hormones, and engineered artificial small molecule ligands that exhibit the required specificity. Natural ligand sequences can also be engineered to increase their specificity for a particular target cell. Selection of a soluble receptor ligand for use in a particular zetakine is governed by the nature of the target cell, and the qualities discussed above with regard to the IL-13 (E13Y) molecule, a preferred ligand for use against glioma. Examples of suitable support regions include the constant (Fc) regions of immunoglobins, human CD8α, and artificial linkers that serve to move the targeting moiety away from the cell surface for improved access to receptor binding on target cells. A preferred support region is the Fc region of an IgG (such as IgG4). Examples of suitable transmembrane domains include the transmembrane domains of the leukocyte CD markers, preferably that of CD8. Examples of intracellular receptor signaling domains are those of the T cell antigen receptor complex, preferably the zeta chain of CD3 also Fcγ RIII costimulatory signaling domains, CD28, DAP10, CD2, alone or in a series with CD3zeta.

In the IL-13 zetakine embodiment, the human IL-13 cDNA having the E13Y amino acid substitution was synthesized by PCR splice overlap extension. A full length IL-13 zetakine construct was assembled by PCR splice overlap extension and consists of the human GM-CSF receptor alpha chain leader peptide, IL-13(E13Y)-Gly-Gly-Gly, human IgG4 Fc, human CD4TM, and human cytoplasmic zeta chain. This cDNA construct was ligated into the multiple cloning site of a modified pMG plasmid under the transcriptional control of the human Elongation Factor-1 alpha promoter (Invivogen, San Diego). This expression vector co-expresses the HyTK cDNA encoding the fusion protein HyTK that combines in a single molecule hygromycin phosphotransferase activity for in vitro selection of transfectants and HSV thymidine kinase activity for in vivo ablation of cells with ganciclovir from the CMV immediate/early promoter. Western blot of whole cell Jurkat lysates pre-incubated with tunicamycin, an inhibitor of glycosylation, with an anti-zeta antibody probe demonstrated that the expected intact 56-kDa chimeric receptor protein is expressed. This receptor is heavily glycosylated consistent with post-translational modification of the native IL-13 cytokine[108]. Flow cytometric analysis of IL-13 zetakine+ Jurkat cells with anti-human IL-13 and anti-human Fc specific antibodies confirmed the cell-surface expression of the IL-13 zetakine as a type I transmembrane protein.

Using established human T cell genetic modification methods developed at City of Hope[107], primary human T cell clones expressing the IL-13 zetakine chimeric immunoreceptor have been generated for pre-clinical functional characterization. IL-13 zetakine+ CD8+ CTL clones display robust proliferative activity in ex vivo expansion cultures. Expanded clones display re-directed cytolytic activity in 4-hr chromium release assays against human IL-13Rα2+ glioblastoma cell lines. The level of cytolytic activity correlates with levels of zetakine expression on T cells and IL-13Rα2 receptor density on glioma target cells. In addition to killing, IL-13 zetakine+ clones are activated for cytokine secretion (IFN-γ, TNF-α, GM-CSF). Activation was specifically mediated by the interaction of the IL-13 zetakine with the IL-13Rα2 receptor on glioma cells since CTL clones expressing an irrelevant chimeric immunoreceptor do not respond to glioma cells, and, since activation can be inhibited in a dose-dependent manner by the addition to culture of soluble IL-13 or blocking antibodies against IL-13 on T cell transfectants and IL-13Rα2 on glioma target cells. Lastly, IL-13 zetakine-expressing CD8+ CTL clones proliferate when stimulated by glioma cells in culture. IL-13 zetakine+ CTL clones having potent anti-glioma effector activity will have significant clinical activity against malignant gliomas with limited collateral damage to normal CNS.

An immunoreceptor according to the present invention can be produced by any means known in the art, though preferably it is produced using recombinant DNA techniques. A nucleic acid sequence encoding the several regions of the chimeric receptor can prepared and assembled into a complete coding sequence by standard techniques of molecular cloning (genomic library screening, PCR, primer-assisted ligation, site-directed mutagenesis, etc.). The resulting coding region is preferably inserted into an expression vector and used to transform a suitable expression host cell line, preferably a T lymphocyte cell line, and most preferably an autologous T lymphocyte cell line, a third party derived T cell line/clone, a transformed humor or xerogenic immunologic effector cell line, for expression of the immunoreceptor. NK cells, macrophages, neutrophils, LAK cells, LIK cells, and stem cells that differentiate into these cells, can also be used. In a preferred embodiment, lymphocytes are obtained from a patient by leukopharesis, and the autologous T cells are transduced to express the zetakine and administered back to the patient by any clinically acceptable means, to achieve anticancer therapy.

Suitable doses for a therapeutic effect would be between about $10^6$ and about $10^9$ cells per dose, preferably in a series of dosing cycles. A preferred dosing regimen consists of four one-week dosing cycles of escalating doses, starting at about 10⁷ cells on Day 0, increasing incrementally up to a target dose of about 10⁸ cells by Day 5. Suitable modes of administration include intravenous, subcutaneous, intracavitary (for example by reservoir-access device), intraperitoneal, and direct injection into a tumor mass.

The following examples are solely for the purpose of illustrating one embodiment of the invention.

EXAMPLE 1

Construction of an Immunoreceptor Coding Sequence

Figure 8A:
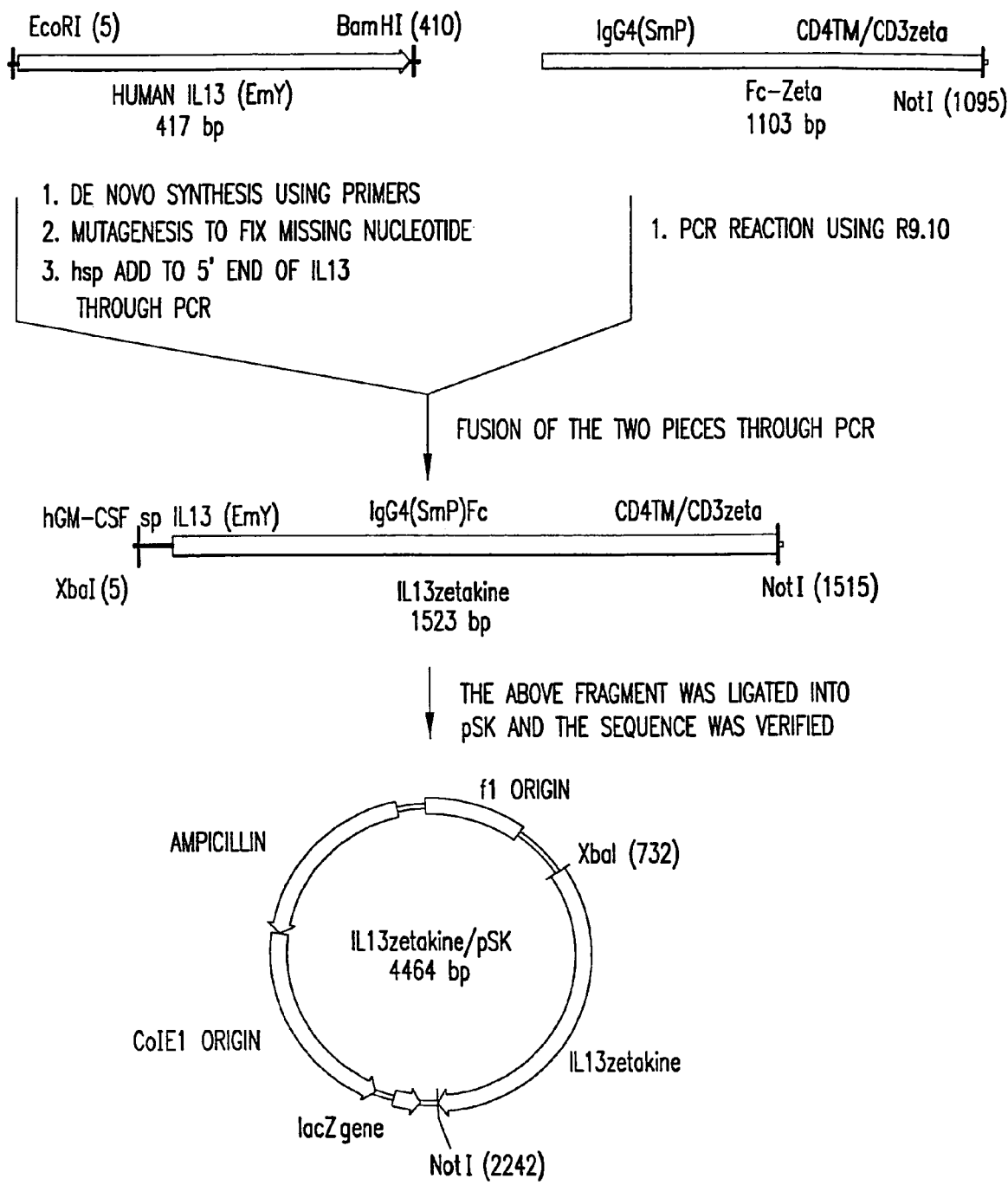
FIG. 8: Flow chart of the construction of IL13zetakine/HyTK-pMG (FIG. 8A, construction of hsp-IL13-IgG4 (SmP)-hinge-Fe-zeta.
FIG. 8B, construction of IL13 Fc:ζp-MG^Pac.
FIG. 8C, construction of IL13/HyTK-pMG).
Figure 8B:
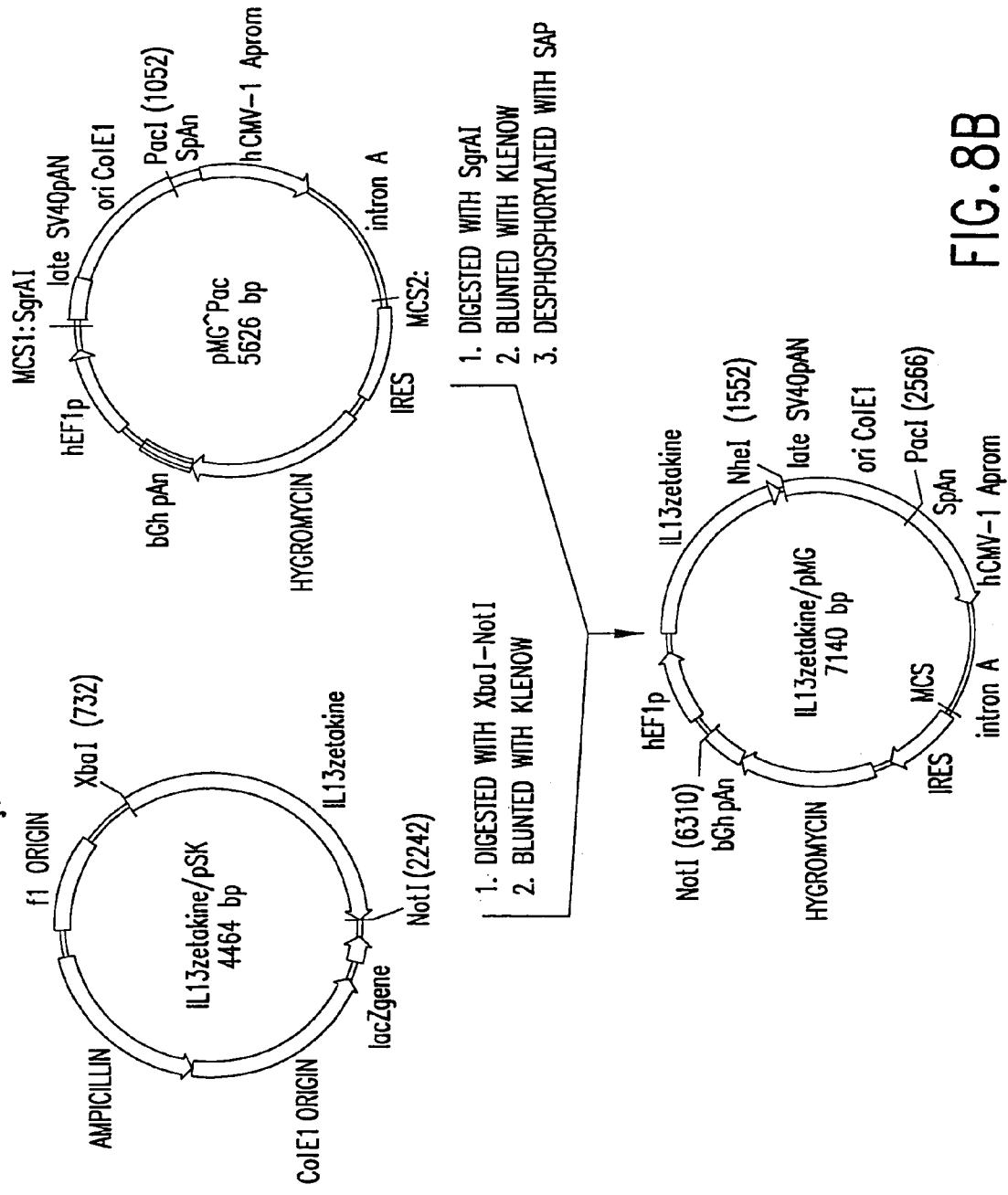

The coding sequence for an immunoreceptor according to the present invention was constructed by de novo synthesis of the IL13(E13Y) coding sequence using the following primers (see FIG. 8 for a flow chart showing the construction of the immunoreceptor coding sequence and expression vector):

[SEQ ID NO.1]
IL13P1:
 EcoRI
TATGAATTCATGGCGCTTTTGTTGACCACGGTCATTGCTCTCACTTGCCT
TGGCGGCTTTGCCTCCCCAGGCCCTGTGCCTCCCTCTACAGCCCTCAG
GTAC

[SEQ ID NO.2]
IL13P2:
GTTGATGCTCCATACCATGCTGCCATTGCAGAGCGGAGCCTTCTGGTTCT
GGGTGATGTTGACCAGCTCCTCAATGAGGTACCTGAGGGCTGTAGAGGGA
G

[SEQ ID NO.3]
1L13P3:
CTCTGGGTCTTCTCGATGGCACTGCAGCCTGACACGTTGATCAGGGATTC
CAGGGCTGCACAGTACATGCCAGCTGTCAGGTTGATGCTCCATACCATGC

[SEQ ID NO.4]
IL13P4:
CCTCGATTTTGGTGTCTCGGACATGCAAGCTGGAAAACTGCCCAGCTGAG
ACCTTGTGCGGGCAGAATCCGCTCAGCATCCTCTGGGTCTTCTCGATGGC

[SEQ ID NO.5]
IL13P5:
 BamHI
TCGGATCCTCAGTTGAACCGTCCCTCGCGAAAAAGTTTCTTTAAATGTAA
GAGCAGGTCCTTTACAAACTGGGCCACCTCGATTTTGGTGTCTCGG

The final sequence (417 bp) was end-digested with EcoRI-BamHI, and ligated into the plasmid pSK (stratagene, LaJolla, Calif.) as ligation 312#3. Ligation 312#3 was mutagenized (stratagene kit, per manufacturer's instructions) to fix a deleted nucleotide using the primers 5': IL13 312#3 mut5-3 (CAACCTGACAGCTGGCATGTACTGTGCAGCCCTGGAATC [SEQ ID NO. 6]) and 3':IL13 312#3 mut3-5 (GATTCCAGGGCTGCACAGTACATGCCAGCTGTCAGGTTG [SEQ ID NO. 7]), and ligation 312#3 as a template, to form ligation 348#1 (IL13zetakine/pSK).

The coding Human GM-CSFR alpha chain Signal Peptide (hsp) coding sequence was fused to the 5' end of IL13(E13Y) by standard PCR splice overlap extension. The hsp sequence (101 bp) was obtained from the template ligation 301#10 (hsp/pSK) (human GCSF receptor α-chain leader sequence from human T cell cDNA), using the primers 5':19hsp5' (ATCTCTAGAGCCGCCACCATGCTTCTCCTGGTGACAAGCCTTC [SEQ ID NO. 8]) (XbaI site highlighted in bold), and 3': hsp-IL13FR (GAGGGAGGCACAGGGCCTGGGATCAGGAGGAATG [SEQ ID NO. 9]). The IL-13 sequence (371 bp) was obtained using the primers 5': hsp-IL13FF (CATTCCTCCTGATCCCAGGCCCTGTGCCTCCCTC [SEQ ID NO. 10]) and 3': IL13-IgG4FR (GGGACCATATTTGGACTCGTTGAACCGTCCCTCGC [SEQ ID NO. 11]), and ligation 312#3 as template. Fusion was achieved using the 101 bp hsp sequence and 371 bp IL13 sequence thus obtained, and the primers 5': 19hsp5' and 3': IL13-IgG4FR, to yeild a 438 bp fusion hsp-IL13 sequence.

A sequence encoding the IgG4 Fc region IgG4m:zeta was fused to the 3' end of the hsp-IL13 fusion sequence using the same methods. The IgG4m:zeta sequence (1119 bp) was obtained using the primers 5': IL13-IgG4FF (GCGAGGGACGGTTCAACGAGTCCAAATATGGTCCC [SEQ ID NO. 12]) and 3': ZetaN3' (ATGCGGCCGCTCAGCGAGGGGGCAGG [SEQ ID NO. 13]) (NotI site highlighted in bold), using the sequence R9.10 (IgG4mZeta/pSK) as template. The 1119 bp IgG4m:zeta sequence was fused to the hsp-IL13 fusion sequence using the respective sequences as templates, and the primers 5': 19hsp5' and 3': ZetaN3', to yield a 1522 bp hsp-IL13-IgG4m:zeta fusion sequence. The ends were digested with XbaI-NotI, and ligated into pSK as ligation 351#7, to create the plasmid IL13zetakine/pSK (4464 bp).

EXAMPLE 2

Construction of Expression Vector

Figure 9:
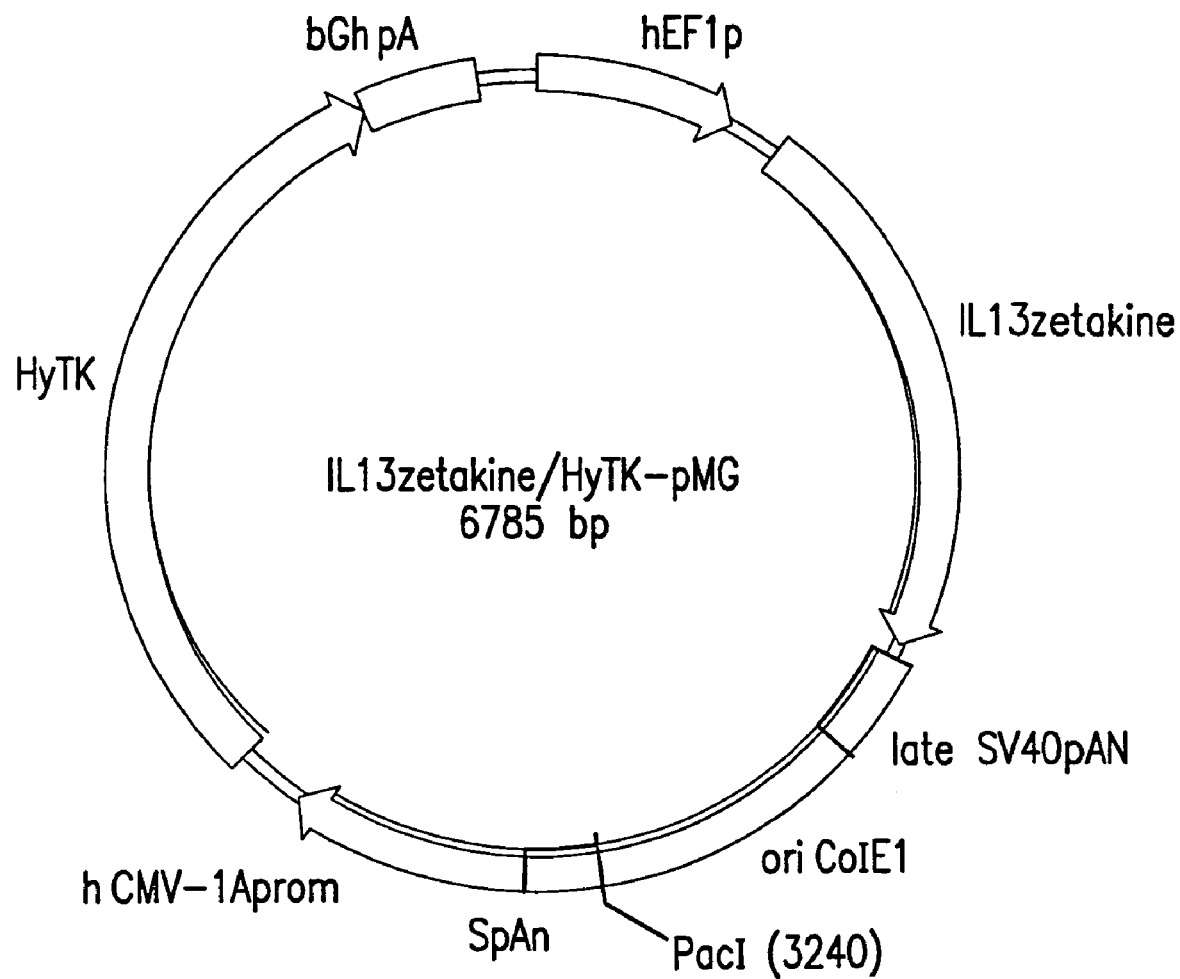
FIG. 9: Plasmid map of IL13zetakine/HyTK-pMG.
Figure 11:
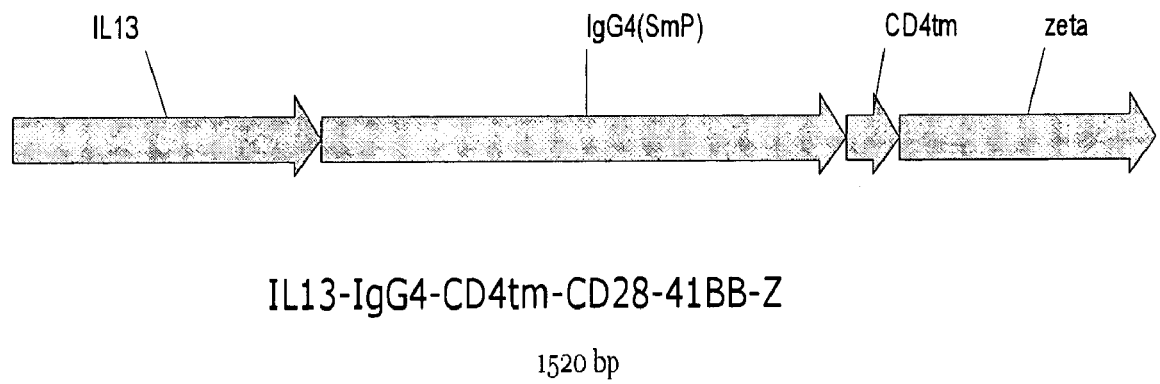
FIG. 11: Schematic diagram showing structure of IL13 zetakine insert.

An expression vector containing the IL13 zetakine coding sequence was created by digesting the IL13zetakine/pSK of Example 1 with XbaI-NotI, and creating blunt ends with Klenow, and ligating the resulting fragment into the plasmid pMG Pac (Invirogen) (first prepared by opening with SgrAI, blunting with Klenow, and dephosphorylation with SAP), to yield the plasmid IL13zetakine /pMG. See FIG. 8. The hygromycin resistance region of IL13zetakine/pMG was removed by digestion with NotI-NheI, and replaced by the selection/suicide fusion HyTK, obtained from plasmid CE7R/HyTK-pMG (Jensen, City of Hope) by digestion with NotI-NheI, to create the expression vector IL13zetakine/HyTK-pMG (6785 bp). This plasmid comprises the Human Elongation Factor-1.alpha. promoter (hEF1p) at bases 6-549, the IL13zetakine coding sequence at bases 692-2185, the Simian Virus 40 Late polyadenylation signal (Late SV40pAN) at bases 2232-2500, a minimal *E. coli* origin of replication (Ori ColE1) at bases 2501-3247, a synthetic polyA and Pause site (SpAN) at bases 3248-3434, the Immeate-early CMV enhancer/promoter (h CMV-1Aprom) at bases 3455-4077, the Hygromycin resistance-Thymidine kinase coding region fusion (HyTK) at bases 4259-6334, and the bovine growth hormone polyadenylation signal and a transcription pause (BGh pAn) at bases 6335-6633. The plasmid has a PacI linearization site at bases 3235-3242. The hEF1p and IL13zetakine elements derived from IL13zetakine/pMG, and the remaining elements derived from CE7R/HyTk-pMG (and with the exception of the HyTK element, ultimately from the parent plasmid pMGAPac). In sum, IL13zetakine/HyTK-pMG is a modified pMG backbone, expressing the IL13zetakine gene from the hEF1 promoter, and the HyTK fusion from the h CMV-1A promoter. A map of the plasmid IL13zetakine/HyTK-pMG appears in FIG. 9. The full nucleic acid sequence of the plasmid is shown in FIG. 10. The sequence of an IL13zetakine insert is given as SEQ ID NO:15, below:

```
                                        (SEQ ID NO: 15)
atgcttctcctggtgacaagccttctgctctgtgagttaccacacccagc attcctcctgatcccaggccctgtgcctccctctacagccctcaggtacc tcattgaggagctggtcaacatcacccagaaccagaaggctccgctctgc
```

-continued

```
aatggcagcatggtatggagcatcaacctgacagctggcatgtactgtgc agccctggaatccctgatcaacgtgtcaggctgcagtgccatcgagaaga cccagaggatgctgagcggattctgcccgcacaaggtctcagctgggcag ttttccagcttgcatgtccgagacaccaaaatcgaggtggcccagtttgt aaaggacctgctcttacatttaaagaaacttttcgcgagggacggttca acgagtccaaatatggtccccatgcccaccatgcccagcacctgagttc ctgggggaccatcagtcttcctgttcccccaaaacccaaggacactct catgatctcccggacccctgaggtcacgtgcgtggtggtggacgtgagcc aggaagacccgaggtccagttcaactggtacgtggatggcgtggaggtg cataatgccaagacaaagccgcgggaggagcagttcaacagcacgtaccg tgtggtcagcgtcctcaccgtcctgcaccaggactggctgaacggcaagg agtacaagtgcaaggtctccaacaaaggcctcccgtcctccatcgagaaa accatctccaaagccaaagggcagccccgagagccacaggtgtacaccct gcccccatcccaggaggagatgaccaagaaccaggtcagcctgacctgcc tggtcaaaggcttctaccccagcgacatcgccgtggagtgggagagcaat gggcagccggagaacaactacaagaccacgcctcccgtgctggactccga cggctccttcttcctctacagcaggctaaccgtggacaagagcaggtggc aggagggaatgtcttctcatgctccgtgatgcatgaggctctgcacaac cactacacacagaagagcctctccctgtctctgggtaaaatggccctgat tgtgctggggggcgtcgccggcctcctgcttttcattgggctaggcatct tcttcagagtgaagttcagcaggagcgcagacgccccgcgtaccagcag ggccagaaccagctctataacgagctcaatctaggacgaagagaggagta cgatgttttggacaagagacgtggccgggaccctgagatgggggaaagc cgagaaggaagaaccctcaggaaggcctgtacaatgaactgcagaaagat aagatggcggaggcctacagtgagattgggatgaaggcgagcgccgag gggcaaggggcacgatggcctttaccagggtctcagtacagccaccaagg acacctacgacgcccttcacatgcaggccctgccccctcgc.
```

EXAMPLE 3

Expression of the Immunoreceptor

Assessment of the integrity of the expressed construct was first delineated by Wester blot probed with an anti-zeta antibody of whole cell lysates derived from Jurkat T cell stable transfectants[107] cocultured in the presence or absence of tunicamycin, an inhibitor of glycosylation. FIG. 1. Jurkat T cell stable transfectants (Jurkat-IL13-pMG bulk line) were obtained by electroporating Jurkat T cells with the IL13zetakine/HyTK-pMG expression vector, followed by selection and expansion of positive transfectants. $2 \times 10^6$ cells from the Jurkat-IL13-pMG bulk line were plated per well in a 24-well plate with or without 5 μg/ml, 10 μg/ml, or 20 μg/ml Tunicamycin. The plate was incubated at 37° C. for 22 hrs. Cells were harvested from each well, and each sample was washed with PBS and resuspended in 50 μl RIPA buffer (PBS, 1% NP40, 0.5% sodium deoxycholate, 0.1% SDS) containing 1 tablet/10 ml Complete Protease Inhibitor Cocktail (Boehringer Mannheim, Indianapolis, Ind.). Samples were incubated on ice for 30 minutes then disrupted by aspiration with syringe with 21 gauge needle then incubated on ice for an additional 30 minutes before being centrifuged at 4° C. for 20 minutes at 14,000 rpm. Samples of centrifuged lysate supernatant were harvested and boiled in an equal volume of sample buffer under reducing conditions, then subjected to SDS-PAGE electrophoresis on a 12% acrylamide gel. Following transfer to nitrocellulose, membrane was allowed to dry O/N at 4° C. Next morning, membrane was blocked in a Blotto solution containing 0.04 gm/ml non-fat dried milk in T-TBS (0.02% Tween 20 in Tris buffered saline pH 8.0) for 1 hour. Membrane was then incubated with primary mouse anti-human CD3ζ monoclonal antibody (Pharmingen, San Diego, Calif.) at a concentration of 1 μg/ml for 2 hours, washed, and then incubated with a 1:3000 dilution (in Blotto solution) of goat anti-mouse IgG alkaline phosphatase conjugated secondary antibody (Bio-Rad ImmunoStar Kit, Hercules, Calif.) for 1 hour. Prior to developing, membrane was washed 4 additional times in T-TBS, and then incubated with 3 ml of phosphatase substrate solution (Biorad ImmunoStar Kit, Hercules, Calif.) for 5 minutes at room temperature. Membrane was then covered with plastic, and exposed to x-ray film. Consistent with the known glycosylation pattern of wild-type human IL-13, the electrophoretic mobility of expressed IL-13 (E13Y) zetakine is demonstrative of a heavily glycosylated protein which, when expressed in the presence of tunicamycin, is reduced to an amino acid backbone of approximately 54 kDa.

The IL-13(E13Y) zetakine traffics to the cell surface as a homodimeric type I transmembrane protein, as evidenced by flow cytometric analysis of transfectants with a phycoerythrin (PE)-conjugated anti human-IL13 monoclonal antibody and a fluorescein isothiocyanate (FITC)-conjugated mouse anti-human Fc (gamma) fragment-specific F(ab')$_2$ antibody. FIG. 2. Jurkat IL13zetakine-pMG transfectants were stained with anti-human Fc(FITC) antibody (Jackson ImmunoResearch, West Grove, Pa.), recombinant human IL13Rα2/human IgG1 chimera (R&D Systems, Minneapolis, Minn.) followed by FITC-conjugated anti human-IgG1 monoclonal antibody (Sigma, St. Louis, Mo.), and an anti-IL13(PE) antibody (Becton Dickinson, San Jose, Calif.) for analysis of cell surface chimeric receptor expression. Healthy donor primary cells were also stained with FITC-conjugated anti-CD4, anti-CD8, anti-TCR, and isotype control monoclonal antibodies (Becton Dickinson, San Jose, Calif.) to assess cell surface phenotype. For each stain, $10^6$ cells were washed and resuspended in 100 μl of PBS containing 2% FCS, 0.2 mg/ml NaN$_3$, and 5 μl of stock antibody. Following a 30 minute incubation at 4° C., cells were washed twice and either stained with a secondary antibody, or resuspended in PBS containing 1% paraformaldehyde and analyzed on a FACSCaliber cytometer.

EXAMPLE 4

Binding of IL13(E13Y) Zetakine to IL13Rα2 Receptor

Figure 3:
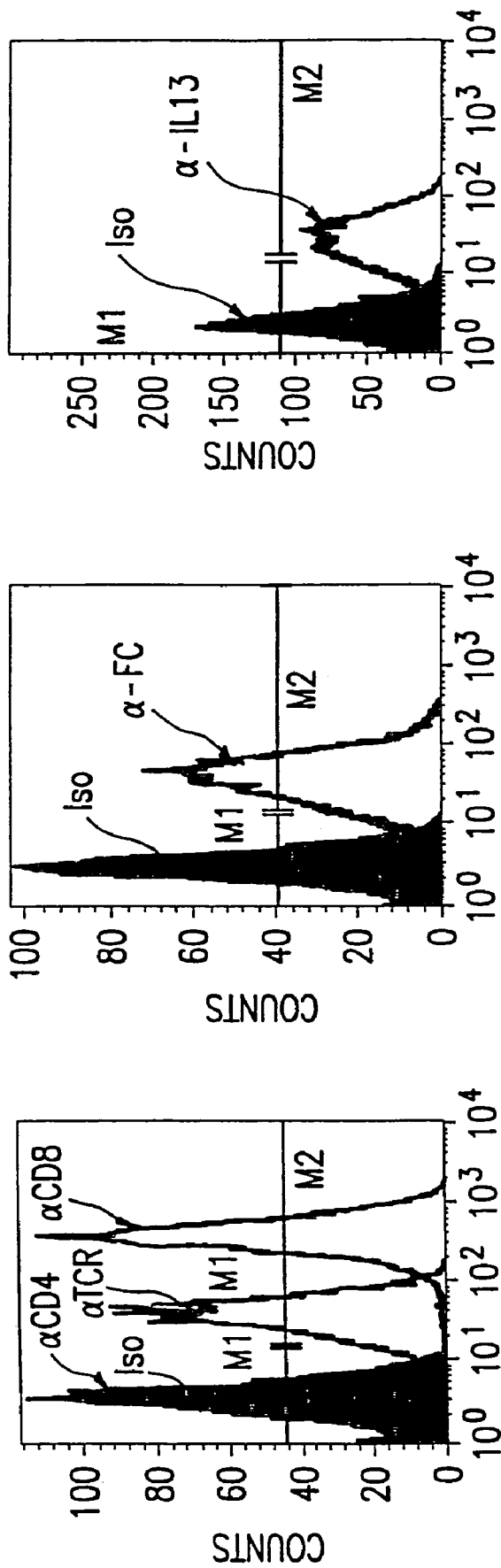
FIG. 3: Results of flow cytometric analysis showing the cell surface phenotype of a representative primary human IL13zetakine+ CTL clone.

IL-13(E13Y), tethered to the cell membrane by human IgG4 Fc (i.e., IL13(E13Y) zetakine), is capable of binding to its target IL13Rα2 receptor as assessed by flow cytometric analysis using soluble IL13Rα2-Fc fusion protein. FIG. 3. Cloned human PBMC IL13zetakine-pMG transfectants were obtained by electroporating PBMC with the IL13zetakine/HyTK-pMG expression vector, followed by selection and expansion of positive transfectants[107]. IL13zetakine+ CTL clonal cells were stained with a fluorescein isothiocyanate (FITC)-conjugated mouse anti-human Fc (gamma) fragment-specific F(ab')$_2$ (Jackson ImmunoResearch, West Grove, Pa.), recombinant human IL13Rα2/human IgG1 chimera (R&D Systems, Minneapolis, Minn.) followed by FITC-conjugated anti human-IgG1 monoclonal antibody (Sigma, St. Louis, Mo.), and a phycoerythrin (PE)-conjugated anti human-IL13 monoclonal antibody (Becton Dickinson, San Jose, Calif.) for analysis of cell surface chimeric receptor expression. Healthy donor primary cells were also stained with FITC-conjugated anti-CD4, anti-CD8, anti-TCR, and isotype control monoclonal antibodies (Becton Dickinson, San Jose, Calif.) to assess cell surface phenotype. For each stain, $10^6$ cells were washed and resuspended in 100 µl of PBS containing 2% FCS, 0.2 mg/ml NaN$_3$, and 5 µl of antibody. Following a 30 minute incubation at 4° C., cells were washed twice and either stained with a secondary antibody, or resuspended in PBS containing 1% paraformaldehyde and analyzed on a FACSCaliber cytometer.

Figure 4A:
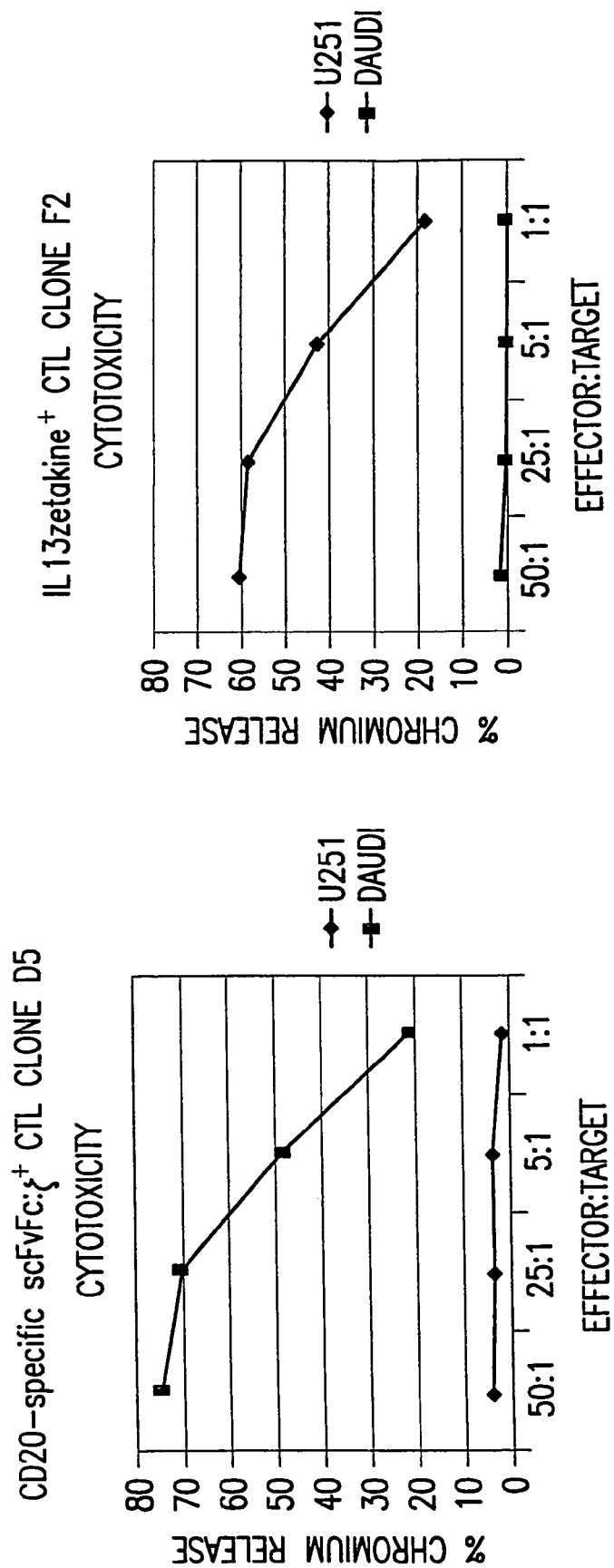
FIG. 4: Results of chromium release assays.
FIG. 4B shows the profile of anti-glioma cytolytic activity by primary human IL13zetakine+ CD8+ CTL clones was observed in glioma cells generally.
Figure 4B:
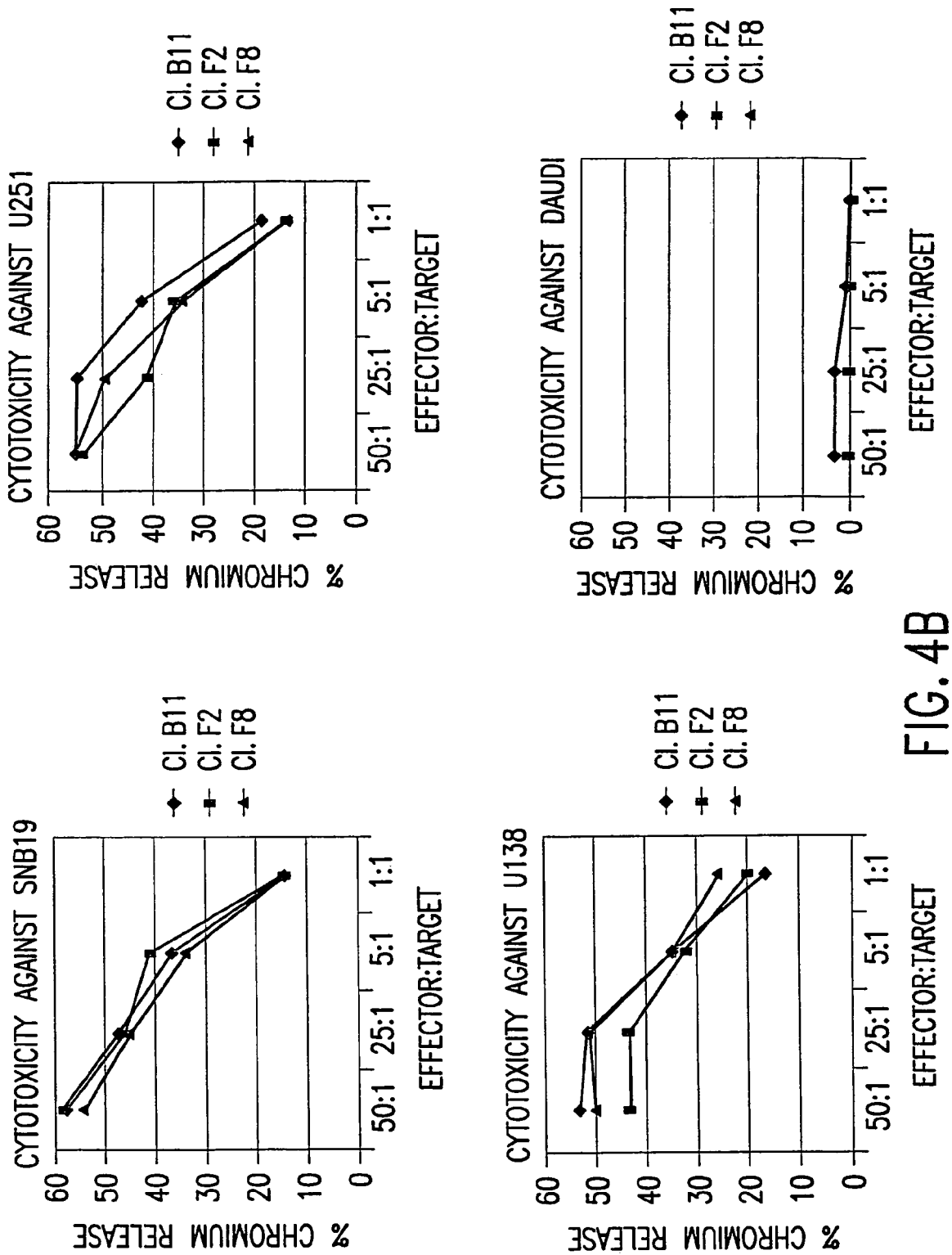

Next, the immunobiology of the IL-13(E13Y) zetakine as a surrogate antigen receptor for primary human T cells was evaluated. Primary human T cells were electroporated with the plasmid expression vector. Positive transformants were selected with hygromycin, cloned in limiting dilution, then expanded by recursive stimulation cyles with OKT3, IL-2 and irradiated feeder cells. Clones demonstrating IL13zetakine expression by Western blot and FACS were then subjected to functional evaluation in 4-hr chromium release assays against a variety of IL-13α2$^+$/CD20$^-$ glioma cell lines (U251, SN-B19, U138), and the IL-13α$^-$/CD20$^+$ B cell lyphocyte line Daudi). These tests showed that IL13zetakine conferred cytolytic activity that was specific for glioma cells (FIG. 4$a$), and that this specific cytolytic activity is present for glioma cells as a class (FIG. 4$b$). The cytolytic activity of MJ-IL13-pMG clones was assayed by employing $^{51}$Cr-labeled SN-B19, U251, and U138 glioma cell lines (IL13α2+/CD20−) and Daudi (CD20+/IL13α2−) as targets. MJ-IL13 effectors were assayed 8-12 days following stimulation. Effectors were harvested, washed, and resuspended in assay media: 2.5×$10^5$, 1.25×$10^5$, 2.5×$10^4$, and 5×$10^3$ effectors were cultured in triplicate at 37° C. for 4 hours with 5×$10^3$ target cells in 96-well V-bottom microtiter plates. After incubation, 100 µl aliquots of cell-free supernatant were harvested and $^{51}$Cr in the supernatants was assayed with a γ-counter. Percent specific cytolysis was calculated as follows:

$$\frac{(\text{Experimental } ^{51}\text{Cr release}) - (\text{control } ^{51}\text{Cr release})}{(\text{Maximum } ^{51}\text{Cr release}) - (\text{control } ^{51}\text{Cr release})} \times 100$$

Control wells contained target cells incubated in the presence of target cells alone. Maximum $^{51}$Cr release was determined by measuring the $^{51}$Cr released by labeled target cells in the presence of 2% SDS. Bulk lines of stabley transfected human T cells consisting of approximately 40% IL-13(E13Y) zetakine$^+$ TCRα/β$^+$ lymphocytes displayed re-directed cytolysis specific for 13Rα2$^+$ glioma targets in 4-hr chromium release assays (>50% specific lysis at E:T ratios of 25:1), with negligable acitivity against IL-13Rα2$^-$ targets (<8% specific lysis at E:T ratios of 25:1). IL-13(E13Y) zetakine$^+$CD8$^+$ TCRα/β$^+$ CTL clones selected on the basis of high-level binding to anti-IL-13 antibody also display redirected IL13Rα2-specific glioma cell killing. FIG. 4$b$.

Figure 5:
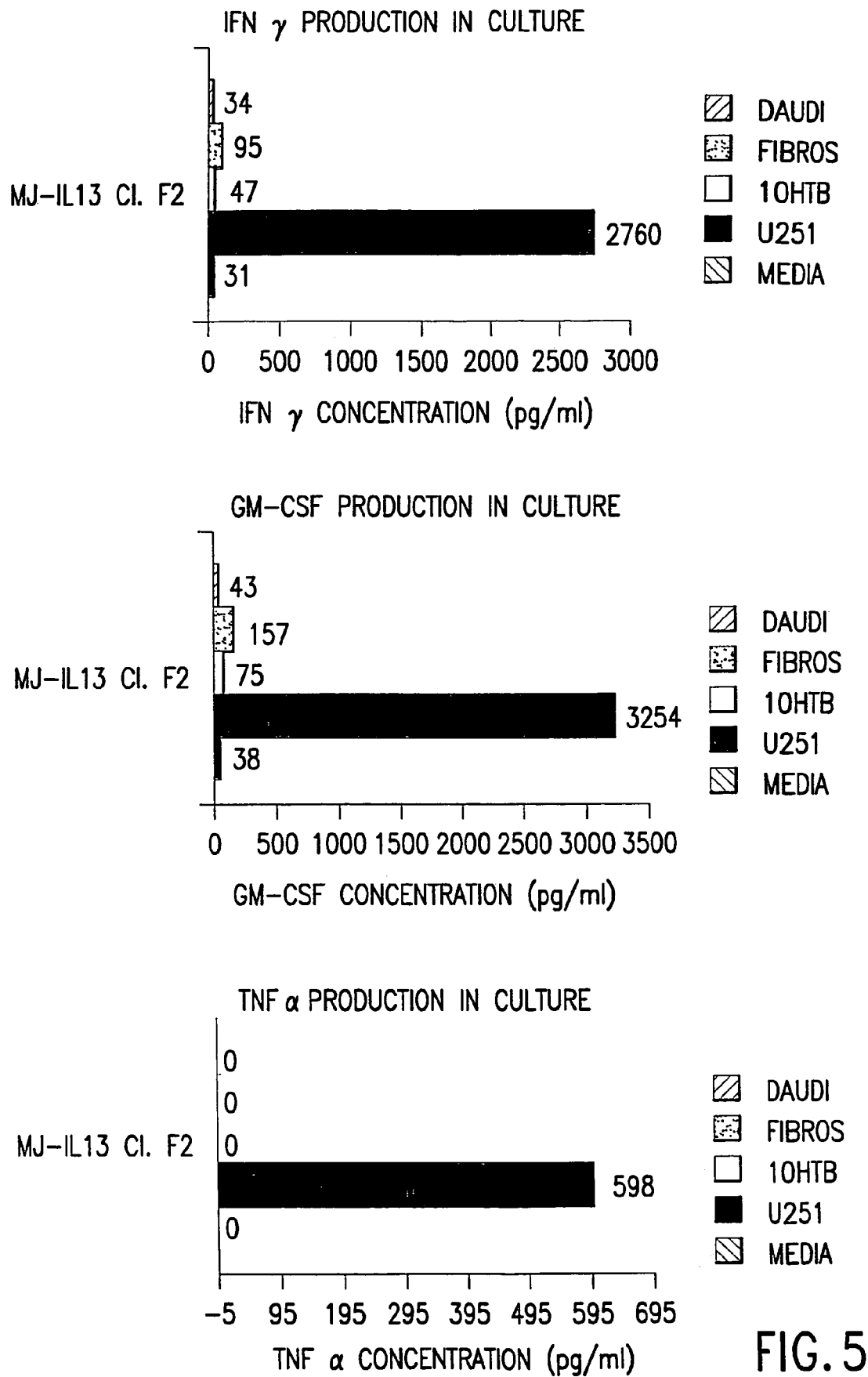
FIG. 5: Results of in vitro stimulation of cytokine production, showing that IL13zetakine+ CTL clones are activated for cytokine production by glioma stimulator cells.
Figure 6A:
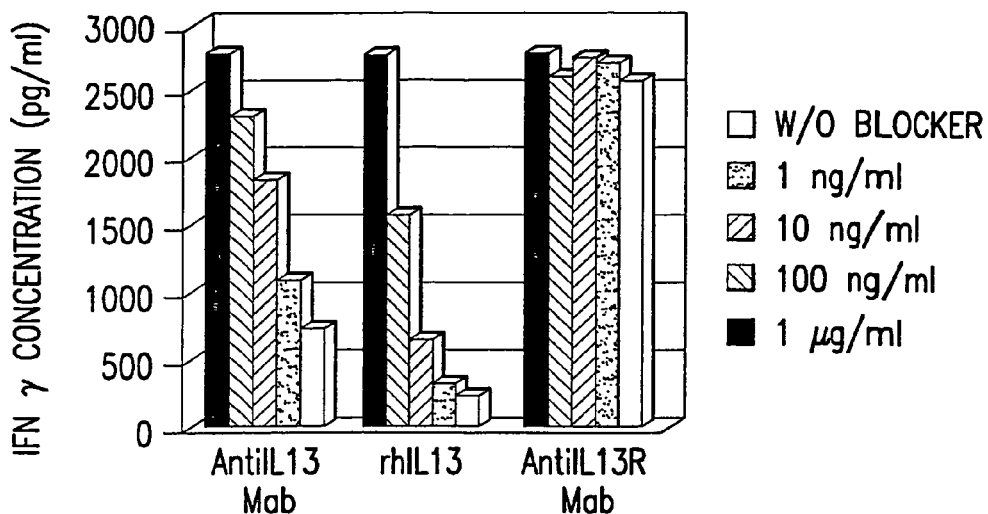
FIG. 6: Results of in vitro stimulation of cytokine production (FIG. 6A, IFNγ.
FIG. 6B, TNFα.
FIG. 6C, GM-CSF), showing the specific inhibition of IL13zetakine+ CTL activation for cytokine production by anti-IL13R Mab and rhIL13.
Figure 6B:
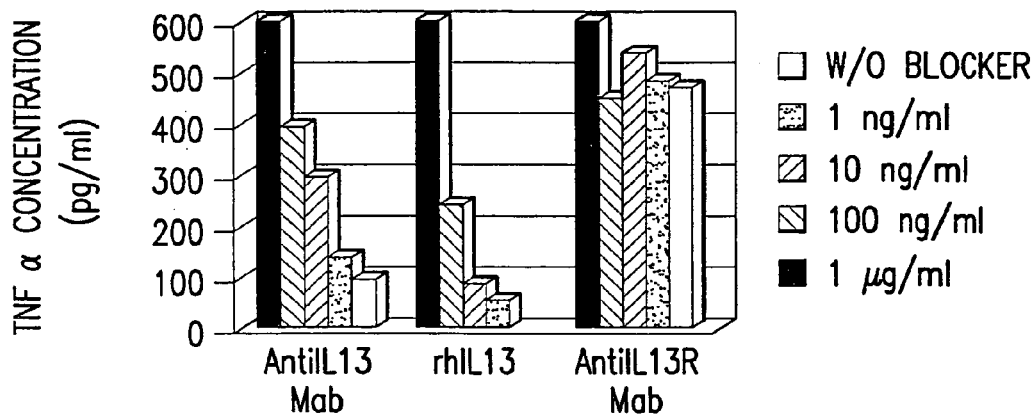
Figure 6C:
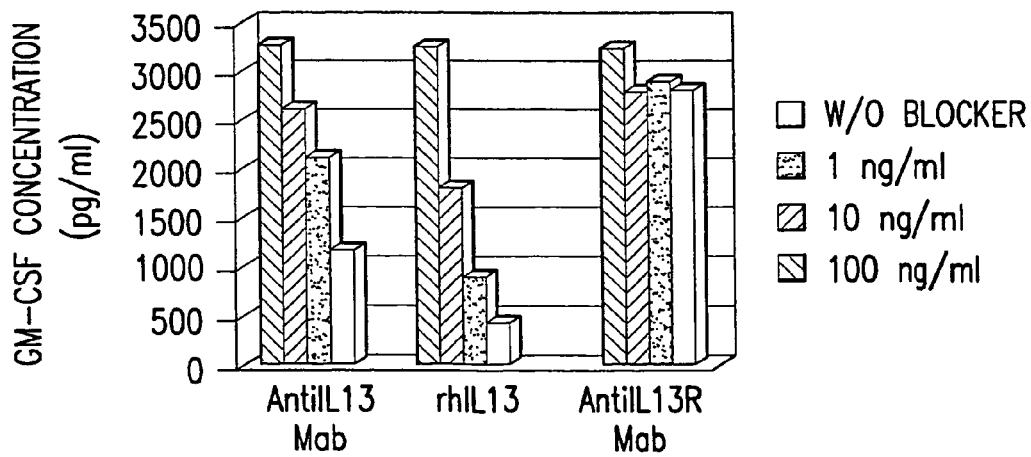
Figure 7A:
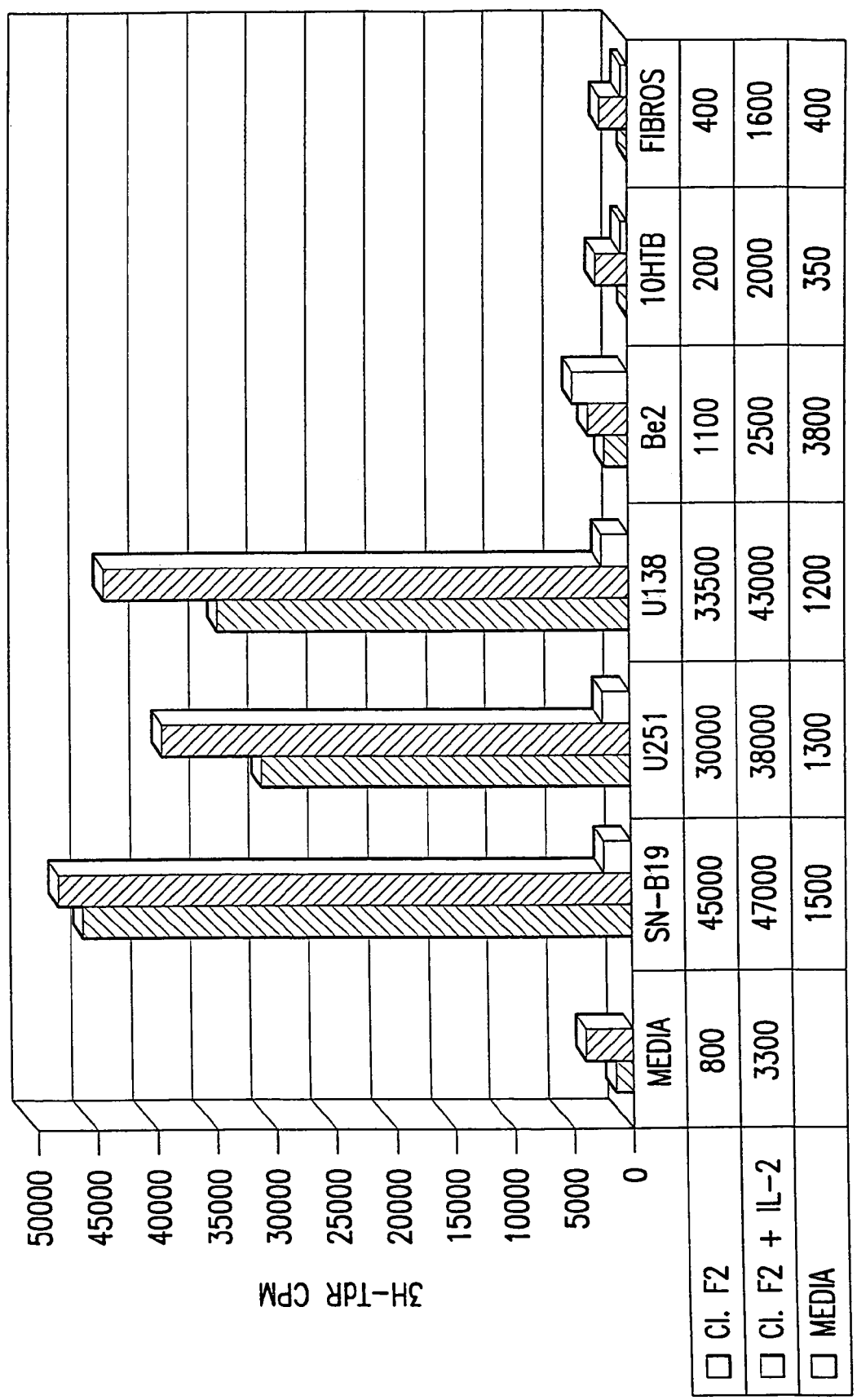
FIG. 7A shows that IL13zetakine[30] CD8+ CTL cells proliferate upon co-culture with glioma stimulators.
Figure 7B:
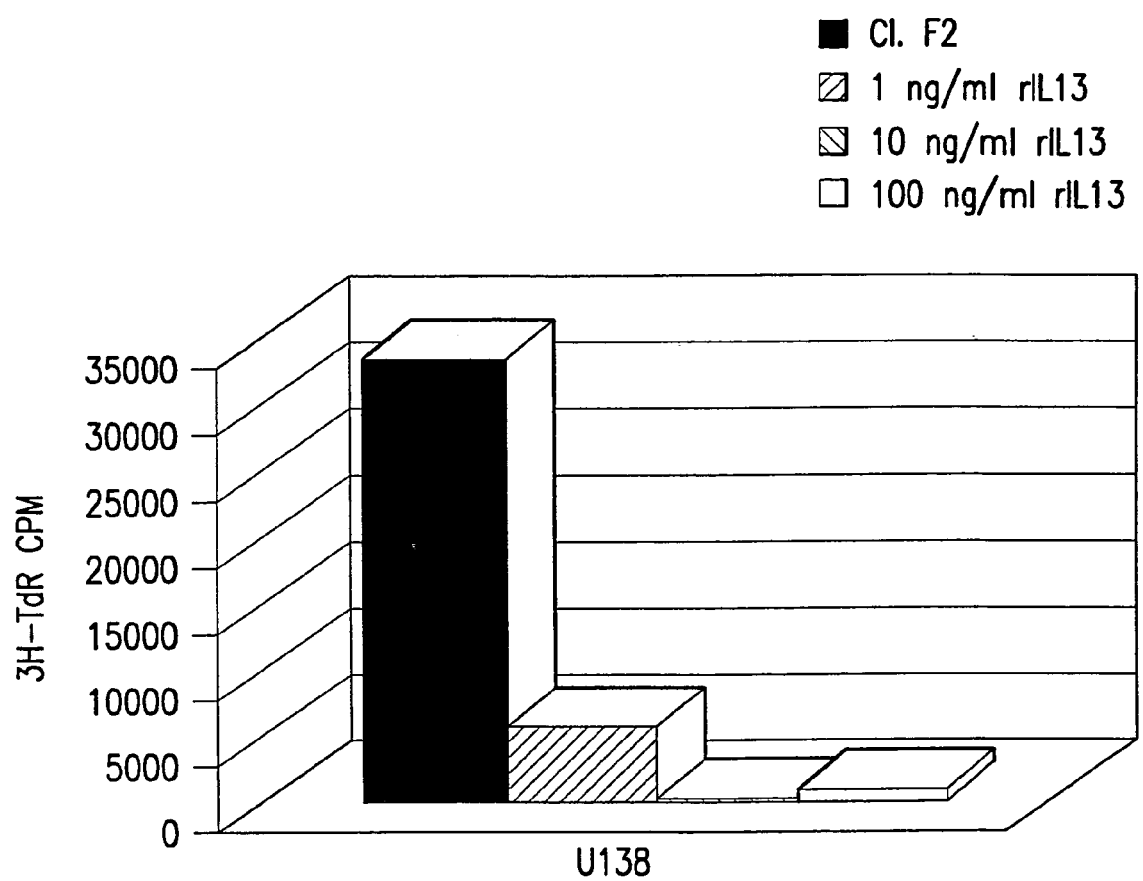
FIG. 7B shows the inhibition of glioma-stimulated proliferation of IL13zetakine+ CD8+ CTL cells by rhIL-13.

IL-13 zetakine-expressing CD8$^+$ CTL clones are activated and proliferate when stimulated by glioma cells in culture. FIGS. 5-7. MJ-IL13-pMG C1. F2 responder cells expressing the IL13 zetakine were evaluated for receptor-mediated triggering of IFNγ, GM-CSF, and TNFα production in vitro. 2×$10^6$ responder cells were co-cultured in 24-well tissue culture plates with 2×$10^5$ irradiated stimulator cells (Daudi, Fibroblasts, Neuroblastoma 10HTB, and glioblastoma U251) in 2 ml total. Blocking rat anti-human-IL13 monoclonal antibody (Pharmingen, San Diego, Calif.), recombinant human IL13 (R&D Systems, Minneapolis, Minn.), and IL13Rα2-specific goat IgG (R&D Systems, Minneapolis, Minn.) were added to aliquots of U251 stimulator cells (2×$10^5$/ml) at concentrations of 1 ng/ml, 10 ng/ml, 100 ng/ml, and 1 µg/ml, 30 minutes prior to the addition of responder cells. Plates were incubated for 72 hours at 37° C., after which time culture supernatants were harvested, aliquoted, and stored at −70° C. ELISA assays for IFNγ, GM-CSF, and TNFα were carried out using the R&D Systems (Minneapolis, Minn.) kit per manufacturer's instructions. Samples were tested in duplicate wells undiluted or diluted at 1:5 or 1:10. The developed ELISA plate was evaluated on a microplate reader and cytokine concentrations determined by extrapolation from a standard curve. Results are reported as picograms/ml, and show strong activation for cytokine production by glioma stimulator cells. FIG. 5, FIG. 6.

Lastly, IL-2 independent proliferation of IL13zetakine$^+$ CD8$^+$ CTL was observed upon co-cultivation with glioma stimulators (FIG. 7$a$), but not with IL13 Rα2 stimulators. Proliferation was inhibited by the addition of rhIL-13 antibody (FIG. 7$b$), showing that the observed proliferation was dependant on binding of zetakine to the IL-13Rα2 glioma cell-specific receptor.

EXAMPLE 5

Preparation of IL-13 zetakine$^+$ T cells suitable for therapeutic use

The mononuclear cells are separated from heparinized whole blood by centrifugation over clinical grade Ficoll (Pharmacia, Uppsula, Sweden). PBMC are washed twice in sterile phosphate buffered saline (Irvine Scientific) and suspended in culture media consisting of RPMI 1640 HEPES, 10% heat inactivated FCS, and 4 mM L-glutamine. T cells present in patient PBMC are polyclonally activated by addition to culture of Orthoclone OKT3 (30 ng/ml). Cell cultures are then incubated in vented T75 tissue culture flasks in the study subject's designated incubator. Twenty-four hours after initiation of culture rhIL-2 is added at 25 U/ml.

Three days after the initiation of culture PBMC are harvested, centrifuged, and resuspended in hypotonic electroporation buffer (Eppendorf) at 20×$10^6$ cells/ml. 25 µg of the plasmid IL13zetakine/HyTK-pMG of Example 3, together with 400 µl of cell suspension, are added to a sterile 0.2 cm electroporation cuvette. Each cuvette is subjected to a single electrical pulse of 250V/40 µs and again incubated for ten minutes at RT. Surviving cells are harvested from cuvettes, pooled, and resuspended in culture media containing 25 U/ml rhIL-2. Flasks are placed in the patient's designated tissue culture incubator. Three days following electroporation hygromycin is added to cells at a final concentration of 0.2 mg/ml. Electroporated PBMC are cultured for a total of 14 days with media and IL-2 supplementation every 48-hours.

The cloning of hygromycin-resistant CD8+ CTL from electroporated OKT3-activated patient PBMC is initiated on day 14 of culture. Briefly, viable patient PBMC are added to a mixture of 100×10⁶ cyropreserved irradiated feeder PBMC and 20×10⁶ irradiated TM-LCL in a volume of 200 ml of culture media containing 30 ng/ml OKT3 and 50 U/ml rhIL-2. This mastermix is plated into ten 96-well cloning plates with each well receiving 0.2 ml. Plates are wrapped in aluminum foil to decrease evaporative loss and placed in the patient's designated tissue culture incubator. On day 19 of culture each well receives hygromycin for a final concentration of 0.2 mg/ml. Wells are inspected for cellular outgrowth by visualization on an inverted microscope at Day 30 and positive wells are marked for restimulation.

The contents of each cloning well with cell growth are individually transferred to T25 flasks containing 50×10⁶ irradiated PBMC, 10×10⁶ irradiated LCL, and 30 ng/ml OKT3 in 25 mls of tissue culture media. On days 1, 3, 5, 7, 9, 11, and 13 after restimulation flasks receive 50 U/ml rhIL-2 and 15 mls of fresh media. On day 5 of the stimulation cycle flasks are also supplemented with hygromycin 0.2 mg/ml. Fourteen days after seeding cells are harvested, counted, and restimulated in T75 flasks containing 150×10⁶ irradiated PBMC, 30×10⁶ irradiated TM-LCL and 30 ng/ml OKT3 in 50 mls of tissue culture media. Flasks receive additions to culture of rhIL-2 and hygromycin as outlined above.

CTL selected for expansion for possible use in therapy are analyzed by immunofluorescence on a FACSCalibur housed in CRB-3006 using FITC-conjugated monoclonal antibodies WT/31 (αβTCR), Leu 2a (CD8), and OKT4 (CD4) to confirm the requisite phenotype of clones (αβTCR+, CD4−, CD8+, and IL13+). Criteria for selection of clones for clinical use include uniform TCR αβ+, CD4−, CD8+ and IL13+ as compared to isotype control FITC/PE-conjugated antibody. A single site of plasmid vector chromosomal integration is confirmed by Southern blot analysis. DNA from genetically modified T cell clones will be screened with a DNA probe specific for the plasmid vector. Probe DNA specific for the HyTK in the plasmid vector is synthesized by random priming with florescein-conjugated dUTP per the manufacture's instructions (Amersham, Arlington Hts, Ill.). T cell genomic DNA is isolated per standard technique. Ten micrograms of genomic DNA from T cell clones is digested overnight at 37° C. then electrophoretically separated on a 0.85% agarose gel. DNA is then transferred to nylon filters (BioRad, Hercules, Calif.) using an alkaline capillary transfer method. Filters are hybridized overnight with probe in 0.5 M Na₂PO₄, pH 7.2, 7% SDS, containing 10 µg/ml salmon sperm DNA (Sigma) at 65° C. Filters are then washed four times in 40 mM Na₂PO₄, pH 7.2, 1% SDS at 65° C. and then visualized using a chemiluminescence AP-conjugated anti-florescein antibody (Amersham, Arlington Hts, Ill.). Criteria for clone selection is a single band unique vector band.

Expression of the IL-13 zetakine is determined by Western blot procedure in which chimeric receptor protein is detected with an anti-zeta antibody. Whole cell lysates of transfected T cell clones are generated by lysis of 2×10⁷ washed cells in 1 ml of RIPA buffer (PBS, 1% NP40, 0.5% sodium deoxycholate, 0.1% SDS) containing 1 tablet/10 ml Complete Protease Inhibitor Cocktail (Boehringer Mannheim). After an eighty minute incubation on ice, aliquots of centrifuged whole cell lysate supernatant are harvested and boiled in an equal volume of loading buffer under reducing conditions then subjected to SDS-PAGE electrophoresis on a precast 12% acrylamide gel (BioRad). Following transfer to nitrocellulose, membranes are blocked in blotto solution containing 0.07 gm/ml non-fat dried milk for 2 hours. Membranes are washed in T-TBS (0.05% Tween 20 in Tris buffered saline pH 8.0) then incubated with primary mouse anti-human CD3ζ monoclonal antibody 8D3 (Pharmingen, San Diego, Calif.) at a concentration of 1 µg/ml for 2 hours. Following an additional four washes in T-TBS, membranes are incubated with a 1:500 dilution of goat anti-mouse IgG alkaline phosphatase-conjugated secondary antibody for 1 hour. Prior to developing, membranes are rinsed in T-TBS then developed with 30 ml of "AKP" solution (Promega, Madison, Wis.) per the manufacturer's instructions. Criteria for clone selection is the presence of a chimeric zeta band.

CD8+ cytotoxic T cell clones expressing the IL-13 zetakine chimeric immunoreceptor recognize and lyse human glioblastoma target cells following interaction of the chimeric receptor with the cell surface target epitope in a HLA-unrestricted fashion. The requirements for target IL-13Rα2 epitope expression and class I MHC independent recognition will be confirmed by assaying each αβTCR+, CD8+, CD4−, IL-13 zetakine+ CTL clones against IL-13Rα2+Daudi cell transfectants and IL-13Rα2-Daudi cells. T cell effectors are assayed 12-14 days following stimulation with OKT3. Effectors are harvested, washed, and resuspended in assay media; and Daudi cell transfectants expressing IL-13Rα2. 2.5×10⁵, 1.25×10⁵, 0.25×10⁵, and 0.05×10⁵ effectors are plated in triplicate at 37° C. for 4 hours with 5×10³ target cells in V-bottom microtiter plates (Costar, Cambridge, Mass.). After centrifugation and incubation, 100 µL aliquots of cell-free supernatant is harvested and counted. Percent specific cytolysis is calculated as:

$$\frac{(\text{Experimental }^{51}\text{Cr release}) - (\text{control }^{51}\text{Cr release})}{(\text{Maximum }^{51}\text{Cr release}) - (\text{control }^{51}\text{Cr release})} \times 100$$

Control wells contain target cells incubated in assay media. Maximum $^{51}$Cr release is determined by measuring the $^{51}$Cr content of target cells lysed with 2% SDS. Criteria for clone selection is >25% specific lysis of IL-13Rα2+ Daudi transfectants at an E:T ratio of 5:1 and a <10% lysis of parental Daudi at the same E:T ratio.

EXAMPLE 6

Treatment of Human Glioma Using IL-13 Zetakine-Expressing T Cells

T cell clones genetically modified according to Example 5 to express the IL-13R zetakine chimeric immunoreceptor and HyTK are selected for:
a. TCRα/β+, CD4−, CD8+, IL-13+ cell surface phenotype as determined by flow cytometry.
b. Presence of a single copy of chromosomally integrated plasmid vector DNA as evidenced by Southern blot.
c. Expression of the IL-13 zetakine protein as detected by Western blot.
d. Specific lysis of human IL-13Rα2+ targets in 4-hr chromium release assays.
e. Dependence on exogenous IL-2 for in vitro growth.
f. Mycoplasma, fungal, bacterial sterility and endotoxin levels <5 EU/ml.
g. In vitro sensitivity of clones to ganciclovir.

Peripheral blood mononuclear cells are obtained from the patient by leukapheresis, preferably following recovery from initial resection surgery and at a time at least three weeks from tapering off steroids and/or their most recent systemic chemotherapy. The target leukapheresis mononuclear cell yield is 5×10⁹ and the target number of hygromycin-resistant cytolytic T cell clones is 25 with the expectation that at least five clones will be identified that meet all quality control parameters for ex-vivo expansion. Clones are cryopreserved and patients monitored by serial radiographic and clinical examinations. When recurrence of progression of disease is documented, patients undergo a re-resection and/or placement of a reservoir-access device (Omaya reservoir) for delivering T cells to the tumor resection cavity. Following recovery from surgery and tapering of steroids, if applicable, the patient commences with T cell therapy.

The patient receives a target of at least four one-week cycles of therapy. During the first cycle, cell dose escalation proceeds from an initial dose on Day 0 of $10^7$ cells, followed by $5 \times 10^7$ cells on Day 3 to the target dose of $10^8$ cells on Day 5. Cycle 2 commences as early as one week from commencement of cycle 1. Those patients demonstrating tumor regression with residual disease on MRI may have additional courses of therapy beginning no earlier than Week 7 consisting of repetition of Cycles 3 and 4 followed by one week of rest/restaging provided these treatments are well tolerated (max. toxicities <grade 3) until such time that disease progression or a CR is achieved based on radiographic evaluation.

Cell doses are at least a log less than doses given in studies employing intracavitary LAK cells (individual cell doses of up to $10^9$ and cumulative cell numbers as high as $2.75 \times 10^{10}$ have been safety administered), ex vivo expanded TILs (up to $10^9$ cells/dose reported with minimal toxicity) and allo-reactive lymphocyte (starting cell dose $11^8$ with cumulative cell doses up to $51.5 \times 10^8$) delivered to a similar patient population[75-85]. The rationale for the lower cell doses as proposed in this protocol is based on the increased in vitro reactivity/anti-tumor potency of IL-13 zetakine+ CTL clones compared to the modest reactivity profile of previously utilized effector cell populations. Low-dose repetitive dosing is favored to avoid potentially dangerous inflammatory responses that might occur with single large cell number instillations. Each infusion will consist of a single T cell clone. The same clone will be administered throughout a patient's treatment course. On the days of T cell administration, expanded clones are aseptically processed by washing twice in 50 cc of PBS then resuspended in pharmaceutical preservative-free normal saline in a volume that results in the cell dose for patient delivery in 2 mls. T cells are instilled over 5-10 minutes. A 2 ml PFNS flush will be administered over 5 minutes following T cells. Response to therapy is assessed by brain MRI+/− gandolinium, with spectroscopy.

Expected side-effects of administration of T cells into glioma resection cavities typically consist of self-limited nausea and vomiting, fever, and transient worsening of existing neurological deficits. These toxicities can be attributed to both the local inflammation/edema in the tumor bed mediated by T cells in combination with the action of secreted cytokines. These side-effects typically are transient and less than grade II in severity. Should patients experience more severe toxicities it is expected that decadron alone or in combination with ganciclovir will attenuate the inflammatory process and ablate the infused cells. The inadvertent infusion of a cell product that is contaminated with bacteria or fungus has the potential of mediating serious or life-threatening toxicities. Extensive pre-infusion culturing of the cell product is conducted to identify contaminated tissue culture flasks and minimize this possibility. On the day of re-infusion, gram stains of culture fluids, as well as, endotoxin levels are performed.

Extensive molecular analysis for expression of IL-13Rα2 has demonstrated that this molecule is tumor-specific in the context of the CNS[44; 46; 48; 54]. Furthermore, the only human tissue with demonstrable IL-13Rα2 expression appears to be the testis[42]. This tumor-testis restrictive pattern of expression is reminiscent of the growing number of tumor antigens (i.e. MAGE, BAGE, GAGE) expressed by a variety of human cancers, most notably melanoma and renal cell carcinoma[109-111]. Clinical experience with vaccine and adoptive T cell therapy has demonstrated that this class of antigens can be exploited for systemic tumor immunotherapy without concurrent autoimmune attack of the testis[112-114]. Presumably this selectively reflects the effect of an intact blood-testis barrier and an immunologically privileged environment within the testis. Despite the exquisite specificity of the mutant IL-13 targeting moiety, toxicities are theoretically possible if cells egress into the systemic circulation in sufficient numbers and recognize tissues expressing the IL-13Rα1/IL-4β receptor. In light of this remote risk, as well as the possibility that instilled T cells in some patients may mediate an overly exuberant inflammatory response in the tumor bed, clones are equipped with the HyTK gene which renders T cells susceptible to in vivo ablation with ganciclovir[115-118]. Ganciclovir-suicide, in combination with an intra-patient T cell dose escalation strategy, helps minimize the potential risk to research participants.

Side effects associated with therapy (headache, fever, chills, nausea, etc.) are managed using established treatments appropriate for the condition. The patient receives ganciclovir if any new grade 3 or any grade 4 treatment-related toxicity is observed that, in the opinion of the treating physician, puts that patient at significant medical danger. Parentally administered ganciclovir is dosed at 10 mg/kg/day divided every 12 hours. A 14-day course will be prescribed but may be extended should symptomatic resolution not be achieved in that time interval. Treatment with ganciclovir leads to the ablation of IL-13 zetakine$^+$ HyTK$^+$CD8$^+$ CTL clones. Patients should be hospitalized for the first 72 hours of ganciclovir therapy for monitoring purposes. If symptoms do not respond to ganciclovir within 48 hours additional immunosuppressive agents including but not limited to corticosteroids and cyclosporin may be added at the discretion of the treating physician. If toxicities are severe, decadron and/or other immunosuppressive drugs along with ganciclovir are used earlier at the discretion of the treating physician.

REFERENCES

1. Davis F G, McCarthy B J. Epidemiology of brain tumors. Curr Opin Neurol. 2000; 13:635-640.
2. Davis F G, Malinski N, Haenszel W, et al. Primary brain tumor incidence rates in four United States regions, 1985-1989: a pilot study. Neuroepidemiology. 1996; 15:103-112.
3. Smith M A, Freidlin B, Ries L A, Simon R. Increased incidence rates but no space-time clustering of childhood astrocytoma in Sweden, 1973-1992: a population-based study of pediatric brain tumors. Cancer. 2000; 88:1492-1493.
4. Ahsan H, Neugut A I, Bruce J N. Trends in incidence of primary malignant brain tumors in USA, 1981-1990. Int J Epidemiol. 1995; 24:1078-1085.
5. Ashby L S, Obbens E A, Shapiro W R. Brain tumors. Cancer Chemother Biol Response Modif. 1999; 18:498-549.
6. Davis F G, Freels S, Grutsch J, Barlas S, Brem S. Survival rates in patients with primary malignant brain tumors stratified by patient age and tumor histological type: an analysis based on Surveillance, Epidemiology, and End Results (SEER) data, 1973-1991. J. Neurosurg. 1998; 88:1-10.

7. Duffner P K, Cohen M E, Myers M H, Heise H W. Survival of children with brain tumors: SEER Program, 1973-1980. Neurology. 1986; 36:597-601.

8. Davis F G, Freels S, Grutsch J, Barlas S, Brem S. Survival rates in patients with primary malignant brain tumors stratified by patient age and tumor histological type: an analysis based on Surveillance, Epidemiology, and End Results (SEER) data, 1973-1991. J. Neurosurg. 1998; 88:1-10.

9. Kolles H, Niedermayer I, Feiden W. [Grading of astrocytomas and oligodendrogliomas]. Pathologe. 1998; 19:259-268.

10. Huncharek M, Muscat J. Treatment of recurrent high grade astrocytoma; results of a systematic review of 1,415 patients. Anticancer Res. 1998; 18:1303-1311.

11. Loiseau H, Kantor G. [The role of surgery in the treatment of glial tumors]. Cancer Radiother. 2000; 4 Suppl 1:48s-52s.

12. Palma L. Trends in surgical management of astrocytomas and other brain gliomas. Forum (Genova). 1998; 8:272-281.

13. Azizi S A, Miyamoto C. Principles of treatment of malignant gliomas in adults: an overview. J Neurovirol. 1998; 4:204-216.

14. Shapiro W R, Shapiro J R. Biology and treatment of malignant glioma. Oncology (Huntingt). 1998; 12:233-240.

15. Chamberlain M C, Kormanik P A. Practical guidelines for the treatment of malignant gliomas. West J. Med. 1998; 168:114-120.

16. Ushio Y. Treatment of gliomas in adults. Curr Opin Oncol. 1991; 3:467-475.

17. Scott J N, Rewcastle N B, Brasher P M, et al. Long-term glioblastoma multiforme survivors: a population-based study. Can J Neurol Sci. 1998; 25:197-201.

18. Finlay J L, Wisoff J H. The impact of extent of resection in the management of malignant gliomas of childhood. Childs Nerv Syst. 1999; 15:786-788.

19. Hess K R. Extent of resection as a prognostic variable in the treatment of gliomas. J Neurooncol. 1999; 42:227-231.

20. van den Bent M J. Chemotherapy in adult malignant glioma. Front Radiat Ther Oncol. 1999; 33:174-191.

21. DeAngelis L M, Burger P C, Green S B, Cairncross J G. Malignant glioma: who benefits from adjuvant chemotherapy? Ann Neurol. 1998; 44:691-695.

22. Armstrong T S, Gilbert M R. Chemotherapy of astrocytomas: an overview. Semin Oncol Nurs. 1998; 14:18-25.

23. Prados M D, Russo C. Chemotherapy of brain tumors. Semin Surg Oncol. 1998; 14:88-95.

24. Prados M D, Scott C, Curran W J, Nelson D F, Leibel S, Kramer S. Procarbazine, lomustine, and vincristine (PCV) chemotherapy for anaplastic astrocytoma: A retrospective review of radiation therapy oncology group protocols comparing survival with carmustine or PCV adjuvant chemotherapy. J Clin Oncol. 1999; 17:3389-3395.

25. Fine H A, Dear K B, Loeffler J S, Black P M, Canellos G P. Meta-analysis of radiation therapy with and without adjuvant chemotherapy for malignant gliomas in adults. Cancer. 1993; 71:2585-2597.

26. Mahaley M S, Gillespie G Y. New therapeutic approaches to treatment of malignant gliomas: chemotherapy and immunotherapy. Clin Neurosurg. 1983; 31:456-469.

27. Millot F, Delval O, Giraud C, et al. High-dose chemotherapy with hematopoietic stem cell transplantation in adults with bone marrow relapse of medulloblastoma: report of two cases. Bone Marrow Transplant. 1999; 24:1347-1349.

28. Kalifa C, Valteau D, Pizer B, Vassal G, Grill J, Hartmann O. High-dose chemotherapy in childhood brain tumours. Childs Nerv Syst. 1999; 15:498-505.

29. Finlay J L. The role of high-dose chemotherapy and stem cell rescue in the treatment of malignant brain tumors. Bone Marrow Transplant. 1996; 18 Suppl 3:S1-S5.

30. Brandes A A, Vastola F, Monfardini S. Reoperation in recurrent high-grade gliomas: literature review of prognostic factors and outcome. Am J Clin Oncol. 1999; 22:387-390.

31. Miyagi K, Ingram M, Techy G B, Jacques D B, Freshwater D B, Sheldon H. Immunohistochemical detection and correlation between MHC antigen and cell-mediated immune system in recurrent glioma by APAAP method. Neurol Med Chir (Tokyo). 1990; 30:649-655.

32. Bauman G S, Sneed P K, Wara W M, et al. Reirradiation of primary CNS tumors. Int J Radiat Oncol Biol Phys. 1996; 36:433-441.

33. Fine H A. Novel biologic therapies for malignant gliomas. Antiangiogenesis, immunotherapy, and gene therapy. Neurol Clin. 1995; 13:827-846.

34. Brandes A A, Pasetto L M. New therapeutic agents in the treatment of recurrent high-grade gliomas. Forum (Genova). 2000; 10:121-131.

35. Pollack I F, Okada H, Chambers W H. Exploitation of immune mechanisms in the treatment of central nervous system cancer. Semin Pediatr Neurol. 2000; 7:131-143.

36. Black K L, Pikul B K. Gliomas—past, present, and future. Clin Neurosurg. 1999; 45:160-163.

37. Riva P, Franceschi G, Arista A, et al. Local application of radiolabeled monoclonal antibodies in the treatment of high grade malignant gliomas: a six-year clinical experience. Cancer. 1997; 80:2733-2742.

38. Liang B C, Weil M. Locoregional approaches to therapy with gliomas as the paradigm. Curr Opin Oncol. 1998; 10:201-206.

39. Yu J S, Wei M X, Chiocca E A, Martuza R L, Tepper R L. Treatment of glioma by engineered interleukin 4-secreting cells. Cancer Res. 1993; 53:3125-3128.

40. Alavi J B, Eck S L. Gene therapy for malignant gliomas. Hematol Oncol Clin North Am. 1998; 12:617-629.

41. Debinski W. Recombinant cytotoxins specific for cancer cells. Ann N Y Acad. Sci. 1999; 886:297-299.

42. Debinski W, Gibo D M. Molecular expression analysis of restrictive receptor for interleukin 13, a brain tumor-associated cancer/testis antigen. Mol Med. 2000; 6:440-449.

43. Mintz A, Debinski W. Cancer genetics/epigenetics and the X chromosome: possible new links for malignant glioma pathogenesis and immune-based therapies. Crit Rev Oncog. 2000; 11:77-95.

44. Joshi B H, Plautz G E, Puri R K. Interleukin-13 receptor alpha chain: a novel tumor-associated transmembrane protein in primary explants of human malignant gliomas. Cancer Res. 2000; 60:1168-1172.

45. Debinski W, Obiri N I, Powers S K, Pastan I, Puri R K. Human glioma cells overexpress receptors for interleukin 13 and are extremely sensitive to a novel chimeric protein composed of interleukin 13 and pseudomonas exotoxin. Clin Cancer Res. 1995; 1:1253-1258.

46. Debinski W, Gibo D M, Hulet S W, Connor J R, Gillespie G Y. Receptor for interleukin 13 is a marker and therapeutic target for human high-grade gliomas. Clin Cancer Res. 1999; 5:985-990.

47. Debinski W. An immune regulatory cytokine receptor and glioblastoma multiforme: an unexpected link. Crit Rev Oncog. 1998; 9:255-268.

48. Debinski W, Slagle B, Gibo D M, Powers S K, Gillespie G Y. Expression of a restrictive receptor for interleukin 13 is associated with glial transformation. J Neurooncol. 2000; 48:103-111.

49. Debinski W, Miner R, Leland P, Obiri N I, Puri R K. Receptor for interleukin (IL) 13 does not interact with IL4 but receptor for IL4 interacts with IL13 on human glioma cells. J Biol. Chem. 1996; 271:22428-22433.

50. Murata T, Obiri N I, Debinski W, Puri R K. Structure of IL-13 receptor: analysis of subunit composition in cancer and immune cells. Biochem Biophys Res Commun. 1997; 238:90-94.

51. Opal S M, DePalo V A. Anti-inflammatory cytokines. Chest. 2000; 117:1162-1172.

52. Romagnani S. T-cell subsets (Th1 versus Th2). Ann Allergy Asthma Immunol. 2000; 85:9-18.

53. Spellberg B, Edwards J E, Jr. Type 1/Type 2 immunity in infectious diseases. Clin Infect Dis. 2001; 32:76-102.

54. Liu H, Jacobs B S, Liu J, et al. Interleukin-13 sensitivity and receptor phenotypes of human glial cell lines: non-neoplastic glia and low-grade astrocytoma differ from malignant glioma. Cancer Immunol Immunother. 2000; 49:319-324.

55. Debinski W, Gibo D M, Obiri N I, Kealiher A, Puri R K. Novel anti-brain tumor cytotoxins specific for cancer cells. Nat Biotechnol. 1998; 16:449-453.

56. Debinski W, Gibo D M, Puri R K. Novel way to increase targeting specificity to a human glioblastoma-associated receptor for interleukin 13. Int J Cancer. 1998; 76:547-551.

57. Debinski W, Thompson J P. Retargeting interleukin 13 for radioimmunodetection and radioimmunotherapy of human high-grade gliomas. Clin Cancer Res. 1999; 5:3143s-3147s.

58. Thompson J P, Debinski W. Mutants of interleukin 13 with altered reactivity toward interleukin 13 receptors. J Biol. Chem. 1999; 274:29944-29950.

59. Brooks W H, Netsky M G, Levine J E. Immunity and tumors of the nervous system. Surg Neurol. 1975; 3:184-186.

60. Bullard D E, Gillespie G Y, Mahaley M S, Bigner D D. Immunobiology of human gliomas. Semin Oncol. 1986; 13:94-109.

61. Coakham H B. Immunology of human brain tumors. Eur J Cancer Clin Oncol. 1984; 20:145-149.

62. Holladay F P, Heitz T, Wood G W. Antitumor activity against established intracerebral gliomas exhibited by cytotoxic T lymphocytes, but not by lymphokine-activated killer cells. J. Neurosurg. 1992; 77:757-762.

63. Holladay F P, Heitz T, Chen Y L, Chiga M, Wood G W. Successful treatment of a malignant rat glioma with cytotoxic T lymphocytes. Neurosurgery. 1992; 31:528-533.

64. Kruse C A, Lillehei K O, Mitchell D H, Kleinschmidt-DeMasters B, Bellgrau D. Analysis of interleukin 2 and various effector cell populations in adoptive immunotherapy of 9L rat gliosarcoma: allogeneic cytotoxic T lymphocytes prevent tumor take. Proc Natl Acad Sci USA. 1990; 87:9577-9581.

65. Miyatake S, Nishihara K, Kikuchi H, et al. Efficient tumor suppression by glioma-specific murine cytotoxic T lymphocytes transfected with interferon-gamma gene. J Natl Cancer Inst. 1990; 82:217-220.

66. Plautz G E, Touhalisky J E, Shu S. Treatment of murine gliomas by adoptive transfer of ex vivo activated tumor-draining lymph node cells. Cell Immunol. 1997; 178:101-107.

67. Saris S C, Spiess P, Lieberman D M, Lin S, Walbridge S, Oldfield E H. Treatment of murine primary brain tumors with systemic interleukin-2 and tumor-infiltrating lymphocytes. J. Neurosurg. 1992; 76:513-519.

68. Tzeng J J, Barth R F, Clendenon N R, Gordon W A. Adoptive immunotherapy of a rat glioma using lymphokine-activated killer cells and interleukin 2. Cancer Res. 1990; 50:4338-4343.

69. Yamasaki T, Kikuchi H. An experimental approach to specific adoptive immunotherapy for malignant brain tumors. Nippon Geka Hokan. 1989; 58:485-492.

70. Yamasaki T, Handa H, Yamashita J, Watanabe Y, Namba Y, Hanaoka M. Specific adoptive immunotherapy with tumor-specific cytotoxic T-lymphocyte clone for murine malignant gliomas. Cancer Res. 1984; 44:1776-1783.

71. Yamasaki T, Handa H, Yamashita J, Watanabe Y, Namba Y, Hanaoka M. Specific adoptive immunotherapy of malignant glioma with long-term cytotoxic T lymphocyte line expanded in T-cell growth factor. Experimental study and future prospects. Neurosurg Rev. 1984; 7:37-54.

72. Kikuchi K, Neuwelt E A. Presence of immunosuppressive factors in brain-tumor cyst fluid. J. Neurosurg. 1983; 59:790-799.

73. Yamanaka R, Tanaka R, Yoshida S, Saitoh T, Fujita K, Naganuma H. Suppression of TGF-beta1 in human gliomas by retroviral gene transfection enhances susceptibility to LAK cells. J Neurooncol. 1999; 43:27-34.

74. Kuppner M C, Hamou M F, Bodmer S, Fontana A, de Tribolet N. The glioblastoma-derived T-cell suppressor factor/transforming growth factor beta 2 inhibits the generation of lymphokine-activated killer (LAK) cells. Int J Cancer. 1988; 42:562-567.

75. Hayes R L. The cellular immunotherapy of primary brain tumors. Rev Neurol (Paris). 1992; 148:454-466.

76. Ingram M, Buckwalter J G, Jacques D B, et al. Immunotherapy for recurrent malignant glioma: an interim report on survival. Neurol Res. 1990; 12:265-273.

77. Jaeckle K A. Immunotherapy of malignant gliomas. Semin Oncol. 1994; 21:249-259.

78. Kruse C A, Cepeda L, Owens B, Johnson S D, Stears J, Lillehei K O. Treatment of recurrent glioma with intracavitary alloreactive cytotoxic T lymphocytes and interleukin-2. Cancer Immunol Immunother. 1997; 45:77-87.

79. Merchant R E, Baldwin N G, Rice C D, Bear H D. Adoptive immunotherapy of malignant glioma using tumor-sensitized T lymphocytes. Neurol Res. 1997; 19:145-152.

80. Nakagawa K, Kamezaki T, Shibata Y, Tsunoda T, Meguro K, Nose T. Effect of lymphokine-activated killer cells with or without radiation therapy against malignant brain tumors. Neurol Med Chir (Tokyo). 1995; 35:22-27.

81. Plautz G E, Barnett G H, Miller D W, et al. Systemic T cell adoptive immunotherapy of malignant gliomas. J. Neurosurg. 1998; 89:42-51.

82. Sankhla S K, Nadkarni J S, Bhagwati S N. Adoptive immunotherapy using lymphokine-activated killer (LAK) cells and interleukin-2 for recurrent malignant primary brain tumors. J Neurooncol. 1996; 27:133-140.

83. Sawamura Y, de Tribolet N. Immunotherapy of brain tumors. J Neurosurg Sci. 1990; 34:265-278.

84. Thomas C, Schober R, Lenard H G, Lumenta C B, Jacques D B, Wechsler W. Immunotherapy with stimulated autologous lymphocytes in a case of a juvenile anaplastic glioma. Neuropediatrics. 1992; 23:123-125.

85. Tsurushima H, Liu S Q, Tuboi K, et al. Reduction of end-stage malignant glioma by injection with autologous cytotoxic T lymphocytes. Jpn J Cancer Res. 1999; 90:536-545.

86. Barba D, Saris S C, Holder C, Rosenberg S A, Oldfield E H. Intratumoral LAK cell and interleukin-2 therapy of human gliomas. J. Neurosurg. 1989; 70:175-182.

87. Hayes R L, Koslow M, Hiesiger E M, et al. Improved long term survival after intracavitary interleukin-2 and lymphokine-activated killer cells for adults with recurrent malignant glioma. Cancer. 1995; 76:840-852.

88. Ingram M, Jacques S, Freshwater D B, Techy G B, Shelden C H, Helsper J T. Salvage immunotherapy of malignant glioma. Arch Surg. 1987; 122:1483-1486.

89. Jacobs S K, Wilson D J, Kornblith P L, Grimm E A. Interleukin-2 or autologous lymphokine-activated killer cell treatment of malignant glioma: phase I trial. Cancer Res. 1986; 46:2101-2104.

90. Jeffes E W, III, Beamer Y B, Jacques S, et al. Therapy of recurrent high-grade gliomas with surgery, autologous mitogen-activated IL-2-stimulated (MAK) killer lymphocytes, and rIL-2: II. Correlation of survival with MAK cell tumor necrosis factor production in vitro. Lymphokine Cytokine Res. 1991; 10:89-94.

91. Merchant R E, McVicar D W, Merchant L H, Young H F. Treatment of recurrent malignant glioma by repeated intracerebral injections of human recombinant interleukin-2 alone or in combination with systemic interferon-alpha. Results of a phase I clinical trial. J Neurooncol. 1992; 12:75-83.

92. Yoshida S, Takai N, Saito T, Tanaka R. [Adoptive immunotherapy in patients with malignant glioma]. Gan To Kagaku Ryoho. 1987; 14:1930-1932.

93. Davico B L, De Monte L B, Spagnoli G C, et al. Bispecific monoclonal antibody anti-CD3 x anti-tenascin: an immunotherapeutic agent for human glioma. Int J Cancer. 1995; 61:509-515.

94. Jung G, Brandl M, Eisner W, et al. Local immunotherapy of glioma patients with a combination of 2 bispecific antibody fragments and resting autologous lymphocytes: evidence for in situ t-cell activation and therapeutic efficacy. Int J Cancer. 2001; 91:225-230.

95. Pfosser A, Brandl M, Salih H, Grosse-Hovest L, Jung G. Role of target antigen in bispecific-antibody-mediated killing of human glioblastoma cells: a pre-clinical study. Int J Cancer. 1999; 80:612-616.

96. Yoshida J, Takaoka T, Mizuno M, Momota H, Okada H. Cytolysis of malignant glioma cells by lymphokine-activated killer cells combined with anti-CD3/antiglioma bifunctional antibody and tumor necrosis factor-alpha. J Surg Oncol. 1996; 62:177-182.

97. Imaizumi T, Kuramoto T, Matsunaga K, et al. Expression of the tumor-rejection antigen SART1 in brain tumors. Int J Cancer. 1999; 83:760-764.

98. Eshhar Z, Waks T, Gross G, Schindler D G. Specific activation and targeting of cytotoxic lymphocytes through chimeric single chains consisting of antibody-binding domains and the gamma or zeta subunits of the immunoglobulin and T-cell receptors. Proc Natl Acad Sci USA. 1993; 90:720-724.

99. Haynes N M, Snook M B, Trapani J A, et al. Redirecting mouse CTL against colon carcinoma: superior signaling efficacy of single-chain variable domain chimeras containing TCR-zeta vs Fc epsilon R1-gamma. J. Immunol. 2001; 166:182-187.

100. Hombach A, Heuser C, Sircar R, et al. An anti-CD30 chimeric receptor that mediates CD3-zeta-independent T-cell activation against Hodgkin's lymphoma cells in the presence of soluble CD30. Cancer Res. 1998; 58:1116-1119.

101. Hombach A, Schneider C, Sent D, et al. An entirely humanized CD3 zeta-chain signaling receptor that directs peripheral blood t cells to specific lysis of carcinoembryonic antigen-positive tumor cells. Int J Cancer. 2000; 88:115-120.

102. Hombach A, Sircar R, Heuser C, et al. Chimeric anti-TAG72 receptors with immunoglobulin constant Fc domains and gamma or zeta signalling chains. Int J Mol Med. 1998; 2:99-103.

103. Moritz D, Wels W, Mattern J, Groner B. Cytotoxic T lymphocytes with a grafted recognition specificity for ERBB2-expressing tumor cells. Proc Natl Acad Sci USA. 1994; 91:4318-4322.

104. Weijtens M E, Willemsen R A, Valerio D, Stam K, Bolhuis R L. Single chain Ig/gamma gene-redirected human T lymphocytes produce cytokines, specifically lyse tumor cells, and recycle lytic capacity. J. Immunol. 1996; 157:836-843.

105. Altenschmidt U, Klundt E, Groner B. Adoptive transfer of in vitro-targeted, activated T lymphocytes results in total tumor regression. J. Immunol. 1997; 159:5509-5515.

106. Jensen M, Tan G, Forman S, Wu A M, Raubitschek A. CD20 is a molecular target for scFvFc:zeta receptor redirected T cells: implications for cellular immunotherapy of CD20+malignancy. Biol Blood Marrow Transplant. 1998; 4:75-83.

107. Jensen M C, Clarke P, Tan G, et al. Human T lymphocyte genetic modification with naked DNA. Mol Ther. 2000; 1:49-55.

108. Minty A, Chalon P, Derocq J M, et al. Interleukin-13 is a new human lymphokine regulating inflammatory and immune responses. Nature. 1993; 362:248-250.

109. Boon T, Cerottini J C, Van den EB, van der BP, Van Pel A. Tumor antigens recognized by T lymphocytes. Annu Rev Immunol. 1994; 12:337-365.

110. Castelli C, Rivoltini L, Andreola G, Carrabba M, Renkvist N, Parmiani G. T-cell recognition of melanoma-associated antigens. J Cell Physiol. 2000; 182:323-331.

111. Chi D D, Merchant R E, Rand R, et al. Molecular detection of tumor-associated antigens shared by human cutaneous melanomas and gliomas. Am J Pathol. 1997; 150:2143-2152.

112. Boon T, Coulie P, Marchand M, Weynants P, Wolfel T, Brichard V. Genes coding for tumor rejection antigens: perspectives for specific immunotherapy. Important Adv Oncol. 1994; 53-69.

113. Cebon J, MacGregor D, Scott A, DeBoer R. Immunotherapy of melanoma: targeting defined antigens. Australas J. Dermatol. 1997; 38 Suppl 1:S66-S72.

114. Greenberg P D, Riddell S R. Tumor-specific T-cell immunity: ready for prime time? J Natl Cancer Inst. 1992; 84:1059-1061.

115. Cohen J L, Saron M F, Boyer O, et al. Preservation of graft-versus-infection effects after suicide gene therapy for prevention of graft-versus-host disease. Hum Gene Ther. 2000; 11:2473-2481.
116. Drobyski W R, Morse H C, III, Burns W H, Casper J T, Sandford G. Protection from lethal murine graft-versus-host disease without compromise of alloengraftment using transgenic donor T cells expressing a thymidine kinase suicide gene. Blood. 2001; 97:2506-2513.
117. Link C J, Jr., Traynor A, Seregina T, Burt R K. Adoptive immunotherapy for leukemia: donor lymphocytes transduced with the herpes simplex thymidine kinase gene. Cancer Treat Res. 1999; 101:369-375.
118. Spencer D M. Developments in suicide genes for preclinical and clinical applications. Curr Opin Mol Ther. 2000; 2:433-440.

---

The invention claimed is:

1. A chimeric immunoreceptor encoded by a nucleic acid sequence comprising SEQ ID NO: 15.

2. A method for treating human cancer, comprising adininistering to a human suffering from a glioma that overexpresses IL13α2 receptor a plurality of T lymphocyte cells expressing the immunoreceptor of claim 1.

3. A vector which comprises a nucleic acid sequence comprising SEQ ID NO: 15.

4. A vector which consists essentially of SEQ ID NO: 14.

* * * * *